United States Patent
Pesach et al.

(10) Patent No.: US 11,598,632 B2
(45) Date of Patent: Mar. 7, 2023

(54) PROPERTIES MEASUREMENT DEVICE

(71) Applicant: Dentlytec G.P.L. LTD., Tel-Aviv (IL)

(72) Inventors: Benny Pesach, Rosh Haayin (IL);
Amitai Reuvenny, Kfar-Saba (IL);
Dana Shemuly, Kfar-Saba (IL)

(73) Assignee: DENTLYTEC G.P.L. LTD., Tel-Aviv (IL)

( * ) Notice: Subject to any disclaimer, the term of this patent is extended or adjusted under 35 U.S.C. 154(b) by 0 days.

(21) Appl. No.: 17/050,365

(22) PCT Filed: Apr. 24, 2019

(86) PCT No.: PCT/IL2019/050464
§ 371 (c)(1),
(2) Date: Oct. 23, 2020

(87) PCT Pub. No.: WO2019/207588
PCT Pub. Date: Oct. 31, 2019

(65) Prior Publication Data
US 2021/0140763 A1    May 13, 2021

Related U.S. Application Data

(60) Provisional application No. 62/662,558, filed on Apr. 25, 2018.

(51) Int. Cl.
*G01B 11/25* (2006.01)
*H04N 13/257* (2018.01)
(Continued)

(52) U.S. Cl.
CPC ...... *G01B 11/2513* (2013.01); *A61B 1/00163* (2013.01); *A61B 1/00194* (2022.02);
(Continued)

(58) Field of Classification Search
CPC .......................... H04N 13/257; H04N 13/254
(Continued)

(56) References Cited

U.S. PATENT DOCUMENTS

| 6,252,623 B1 | 6/2001 | Lu et al. |
| 6,549,288 B1 | 4/2003 | Migdal et al. |

(Continued)

FOREIGN PATENT DOCUMENTS

| EP | 2026034 A2 | 2/2009 |
| WO | WO 2016/188939 A1 | 12/2016 |

(Continued)

OTHER PUBLICATIONS

Restriction Official Action dated Mar. 2, 2021 From the US Patent and Trademark Office Re. U.S. Appl. No. 16/343,337. (5 Pages).

(Continued)

*Primary Examiner* — Amir Shahnami
(74) *Attorney, Agent, or Firm* — Cooley LLP

(57) ABSTRACT

An intra-oral optical scanning method for intra-oral optical scanning including projecting a pattern, the pattern including at least a first area illuminated by a first color of light and a second area illuminated by a second color of light and at least one non-illuminated area onto an intra-oral feature, making a first image of the first area, the second area and the non-illuminated area differentiating between the first color of light and the second color of light in the first image of the projected pattern, and determining from the image of the non-illuminated area at least one of an ambient light level, a level of scattered light, a level of light absorption and a level of light reflected from at least one of the first area and the second area. Related apparatus and methods are also described.

37 Claims, 33 Drawing Sheets

(51) Int. Cl.
  *A61B 1/24* (2006.01)
  *H04N 13/254* (2018.01)
  *A61C 9/00* (2006.01)
  *A61B 1/00* (2006.01)
  *A61B 1/06* (2006.01)

(52) U.S. Cl.
  CPC .............. *A61B 1/06* (2013.01); *A61B 1/0605* (2022.02); *A61B 1/24* (2013.01); *A61C 9/006* (2013.01); *H04N 13/254* (2018.05); *H04N 13/257* (2018.05)

(58) Field of Classification Search
  USPC .......................................................... 348/46
  See application file for complete search history.

(56) References Cited

U.S. PATENT DOCUMENTS

| | | | |
|---|---|---|---|
| 7,494,338 | B2 | 2/2009 | Durbin et al. |
| 7,724,932 | B2 | 5/2010 | Ernst et al. |
| 9,325,966 | B2 | 4/2016 | Tin |
| 9,454,846 | B2 | 9/2016 | Pesach et al. |
| 9,593,982 | B2 | 3/2017 | Rhoads et al. |
| 10,159,542 | B2 | 12/2018 | Pesach et al. |
| 10,966,614 | B2 | 4/2021 | Pesach et al. |
| 2005/0089214 | A1 | 4/2005 | Rubbert et al. |
| 2006/0154198 | A1 | 7/2006 | Durbin et al. |
| 2006/0279820 | A1* | 12/2006 | Riley .................... G02B 7/004 359/15 |
| 2008/0063998 | A1 | 3/2008 | Liang et al. |
| 2009/0221874 | A1 | 9/2009 | Vinther et al. |
| 2010/0284589 | A1 | 11/2010 | Thiel et al. |
| 2010/0311005 | A1 | 12/2010 | Liang |
| 2011/0074932 | A1* | 3/2011 | Gharib ............... G01B 11/2545 348/50 |
| 2018/0067327 | A1* | 3/2018 | Peng ..................... G03B 33/12 |
| 2018/0106593 | A1 | 4/2018 | Arden et al. |
| 2018/0125338 | A1 | 5/2018 | Pfeiffer et al. |
| 2018/0299262 | A1* | 10/2018 | Thiel .................. A61B 1/00009 |
| 2019/0025429 | A1 | 8/2019 | Pesach et al. |
| 2019/0259205 | A1* | 8/2019 | Nissinen ............... G06T 19/006 |
| 2021/0162657 | A1* | 6/2021 | Chartrain .............. B29C 64/209 |

FOREIGN PATENT DOCUMENTS

| | | |
|---|---|---|
| WO | WO 2018/073 824 A1 | 4/2018 |
| WO | WO 2019/207588 A2 | 10/2019 |

OTHER PUBLICATIONS

Communication Pursuant to Article 94(3) dated Nov. 10, 2021 From the European Patent Office Re. Application No. 17862210.6. (5 Pages).

Notice of Allowance dated Apr. 26, 2022 together with Interview Summary dated Apr. 22, 2022 from US Patent and Trademark Office Re. U.S. Appl. No. 16/343,337. (10 pages).

Official Action dated Aug. 5, 2021 from US Patent and Trademark Office Re. U.S. Appl. No. 16/343,337. (35 Pages).

International Preliminary Report on Patentability dated May 2, 2019 From the International Bureau of WIPO Re. Application No. PCT/IL2017/051150. (9 Pages).

International Preliminary Report on Patentability dated Nov. 5, 2020 From the International Bureau of WIPO Re. Application No. PCT/IL2019/050464. (12 Pages).

International Search Report and the Written Opinion dated Nov. 11, 2019 From the International Searching Authority Re. Application No. PCT/IL2019/050464. (20 Pages).

International Search Report and the Written Opinion dated Jan. 25, 2018 From the International Searching Authority Re. Application No. PCT/IL2017/051150. (22 Pages).

Invitation to Pay Additional Fees, Communication Relating to the Results of the Partial International Search and the Provisional Opinion dated Aug. 7, 2019 From the International Searching Authority Re. Application No. PCT/IL2019/050464. (13 Pages).

Supplementary European Search Report and the European Search Opinion dated May 15, 2020 From the Emopean Patent Office Re. Application No. 17862210.6. (9 Pages).

Notice of Allowance dated Aug. 19, 2022 from U.S. Appl. No. 16/343,337.(10 Pages).

Feng et al. "Monte Carlo Simulations of Photon Migration Path Distributions in Multiple Scattering Media", Proceeding of the SPIE, 1888, Photon Migration and Imaging in Random Media and Tissues, 1888: 77-89, Sep. 14, 1993.

Fried et al. "Nature of Light Scattering in Dental Enamel and Dentin at Visible and Near-Infrared Wavelengths", Applied Optics, 34(7): 1278-1285, Mar. 1, 1995.

Lapray et al. "Multispectral Filter Arrays: Recent Advances and Practical Implementation", Sensors, 14(11): 21626-21659, Nov. 17, 2014.

Zhang et al. "Rapid Shape Acquisition Using Color Structured Light and Multi-Pass Dynamic Programming", 2002 Proceedings of the First International Symposium on 3D Data Processing and Visualization and Transmission, Padua, Italy, Jun. 19-21, 2002, 13 P., Jun. 19, 2002.

* cited by examiner

FIG. 6O
FIG. 6L
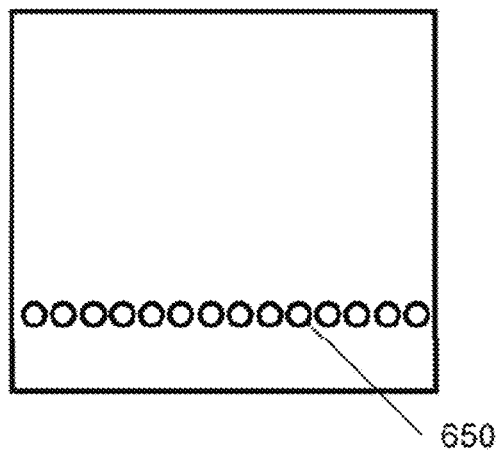
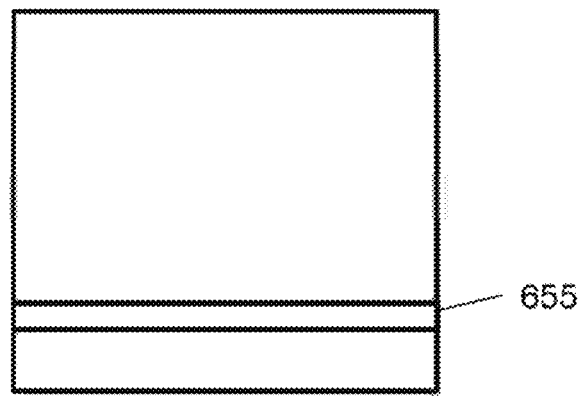
FIG. 6P
FIG. 6Q
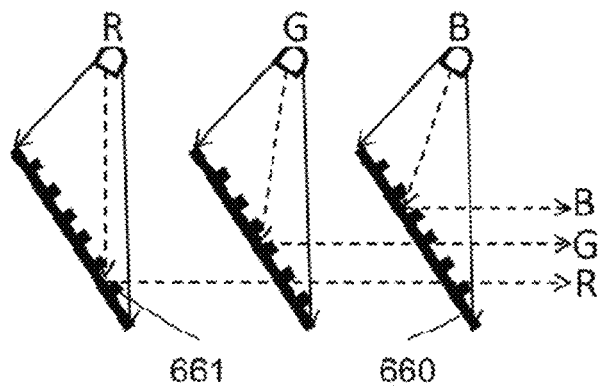
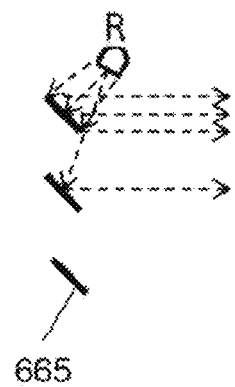

FIG. 18A

| B1 | C  | C  | C  | C  | B1 | C  |
|----|----|----|----|----|----|----|
| C  | B2 | C  | C  | C  | C  | B2 |
| C  | C  | B3 | C  | C  | C  | C  |
| C  | C  | C  | B4 | C  | C  | C  |
| C  | C  | C  | C  | B5 | C  | C  |
| B1 | C  | C  | C  | C  | B1 | C  |
| C  | B2 | C  | C  | C  | C  | B2 |

FIG. 18B

| B1 | C | B3 | C | B5 | C | B2 |
|----|---|----|---|----|---|----|
| B2 | C | B4 | C | B1 | C | B3 |
| B1 | C | B3 | C | B5 | C | B2 |
| B2 | C | B4 | C | B1 | C | B3 |
| B1 | C | B3 | C | B5 | C | B2 |
| B2 | C | B4 | C | B1 | C | B3 |
| B1 | C | B3 | C | B5 | C | B2 |

PROPERTIES MEASUREMENT DEVICE

RELATED APPLICATIONS

This application is a National Phase of PCT Patent Application No. PCT/IL2019/050464 having International filing date of Apr. 24, 2019, which claims the benefit of priority under 35 USC § 119(e) of U.S. Provisional Application No. 62/662,558, filed on Apr. 25, 2018.

The contents of the above applications are all incorporated by reference as if fully set forth herein in their entirety.

FIELD AND BACKGROUND OF THE DISCLOSURE

The present disclosure, in some embodiments thereof, relates to measurement of optical properties of a substance combined with 3D modeling, and more particularly, but not exclusively, to dental measurements and intra-oral scanning.

U.S. Pat. No. 7,724,932 B2 to Maurice et al. discloses "A method for creating three-dimensional models of intra-oral scenes and features. The intra-oral scene is illuminated by a two-dimensional array of structured illumination points, with anti-aliasing achieved by using stored two-dimensional patterns of pixels for anti-aliasing. Using a single camera to form images reduces the amount of apparatus necessary to introduce into the patient's mouth. Three-dimensional models are obtained from the single image by triangulation with a stored image of the structured illumination onto a reference surface such as a plane. Alternative methods include the use of "bar-coded" one-dimensional patterns. (Abstract).

Rapid shape acquisition using color structured light and multi-pass dynamic programming L Zhang, B Carless, SM Seitz—3D Data Processing, 2002, appears to present, "a color structured light technique for recovering object shape from one or more images. The technique works by projecting a pattern of stripes of alternating colors and matching the projected color transitions with observed edges in the image. The correspondence problem is solved using a novel, multi-pass dynamic programming algorithm that eliminates global smoothness assumptions and strict ordering constraints present in previous formulations. The resulting approach is suitable for generating both high-speed scans of moving objects when projecting a single stripe pattern and high-resolution scans of static scenes using a short sequence of time-shifted stripe patterns. In the latter case, space-time analysis is used at each sensor pixel to obtain inter-frame depth localization. Results are demonstrated for a variety of complex scenes."

U.S. Pat. No. 9,593,982 apparently discloses, "A smartphone," "adapted for use as an imaging spectrometer, by synchronized pulsing of different LED light sources as different image frames are captured by the phone's CMOS image sensor. A particular implementation employs the CIE color matching functions, and/or their orthogonally transformed functions, to enable direct chromaticity capture. A great variety of other features and arrangements are also detailed."

Lapray et al. Multispectral Filter Arrays: Recent Advances and Practical Implementation, Sensors 2014, 14(11), 21626-21659; doi:10.3390/s141121626 appears to disclose that, "Thanks to some technical progress in interference filter design based on different technologies, we can finally successfully implement the concept of multispectral filter array-based sensors. This article provides the relevant state-of-the-art for multispectral imaging systems and presents the characteristics of the elements of our multispectral sensor as a case study. The spectral characteristics are based on two different spatial arrangements that distribute eight different bandpass filters in the visible and near-infrared area of the spectrum. We demonstrate that the system is viable and evaluate its performance through sensor spectral simulation."

Other references include U.S. Pat. No. 9,454,846.

All of the above noted patent documents are incorporated herein by reference.

SUMMARY OF THE DISCLOSURE

According to an aspect of some embodiments of the disclosure, there is provided a method for structured light scanning of an intra-oral scene, comprising projecting onto the intra-oral scene a color-coded pattern comprising an arrangement of entities having edges between them; each entity comprising a different narrow band of wavelengths; and detecting the projected pattern as a plurality of pixels in an acquired image of the scene using at least two narrowband filters, wherein for each pixel of at least 95% of the pixels of an entity of interest comprising a first band of wavelengths, a contribution of light from a second band of wavelengths of an adjacent entity is less than 10%.

In some embodiments, at least 5 narrowband filters are used.

In some embodiments, at least one of the filters comprises an interference filter.

In some embodiments, the pattern entities comprise parallel stripes.

In some embodiments, the pattern comprises at least 5 different wavelength bands.

In some embodiments, the pattern comprises at least 8 different wavelength bands.

In some embodiments, the pattern comprises at least 16 different wavelength bands.

In some embodiments, the at least 5 wavelength bands are selected from the range of 400-500 nm.

In some embodiments, the method further comprises restoring the projected pattern by associating an imaged entity to a projected entity by identifying the different wavelengths.

In some embodiments, the different wavelengths are projected and/or detected simultaneously.

In some embodiments, the different wavelengths are projected and/or detected sequentially in time.

In some embodiments, detecting using the filters is effective to reduce optical crosstalk between the pattern entities, caused as a result of volume scattering of the projected light inside contents of the intra-oral scene.

According to an aspect of some embodiments of the disclosure, there is provided a scanner system for imaging an intra-oral scene comprising: an intraoral portion sized and shaped for insertion into the oral cavity, the intraoral portion including: a light source configured for projecting a color-coded pattern onto the intra-oral scene; an imager positioned to image the scene, the imager comprising at least two narrowband filters suitable for detecting at least two different wavelength bands of the pattern.

In some embodiments, at least one of the filters comprises an interference filter.

In some embodiments, the different wavelength bands are detected by different pixels of the imager.

In some embodiments, pixels of the imager are covered with interference filters that match the different wavelength bands of the pattern.

In some embodiments, at least one of the filters is tunable and is configured for detecting the different wavelength bands sequentially.

In some embodiments, the light source comprises a plurality of LEDs arrayed adjacent each other, each LED configured for emitting light at one of the different wavelength bands. In some embodiments, the light source is a wide spectrum light source, and a set of narrowband filters suitable for transmitting the selected wavelengths are illuminated by the light source for projecting the color-coded pattern onto the scene.

In some embodiments, the light source is a wide spectrum light source, and a grating that diffracts light from the wide spectrum light source forms at least one of the components for projecting the color-coded pattern onto the scene.

In some embodiments, the light source is a variable wavelength source.

In some embodiments, the imager is a hyperspectral imager.

In some embodiments, the imager is a hyperspectral imager comprising at least 8 spectral bands.

According to an aspect of some embodiments of the disclosure, there is provided a method for structured light scanning of an intra-oral scene, comprising projecting onto the intra-oral scene a color-coded pattern comprising color entities separated from each other by dark regions, wherein the dark regions are sized to reduce optical crosstalk by being large enough so as to avoid geometrical overlap between the imaged entities; detecting the projected pattern in an acquired image of the scene; and determining one or more depths in the scene.

In some embodiments, the projected pattern is imaged using a color imager comprising a Bayer filter.

In some embodiments, the color imager is an RGB (Red Blue Green) color imager.

In some embodiments, the color imager is an RGBI (Red Blue Green IR) color imager.

In some embodiments, the detecting comprises determining colors in the imaged pattern using the dark regions as reference.

In some embodiments, the pattern entities comprise parallel stripes.

In some embodiments, the pattern comprises colored stripes separated from each other by dark regions in the form of stripes.

In some embodiments, determining comprises subtracting the color obtained in a dark region from the color obtained in a stripe of interest to reduce spectral crosstalk.

In some embodiments, the dark region comprises a non-illuminated area.

In some embodiments, detecting comprises indexing the color entities of the pattern, and the dark regions define entities of the pattern which can be indexed in addition to the color entities.

According to an aspect of some embodiments of the disclosure, there is provided a method for structured light scanning of an intra-oral scene, comprising acquiring at least one image of the intra-oral scene under unstructured lighting; acquiring at least one image of the intra-oral scene under patterned lighting; and constructing a 3D model of the scene using inner-image information obtained from the image acquired under unstructured lighting and inner-image information obtained from the image acquired under the patterned lighting.

In some embodiments, the unstructured lighting comprises uniform lighting.

In some embodiments, the method comprises sequentially interchanging between the acquiring of a uniform light image and the acquiring of a patterned image.

In some embodiments, constructing comprises identifying borders of smooth patches in the scene, the borders indicative of depth discontinuities, and the smooth patches are indexed in a continuous manner.

In some embodiments, information obtained from the image acquired under unstructured lighting is used for one or more of: coloring of the reconstructed scene, assessment of a geometry of the scene, evaluation of reflection characteristics of contents of the scene, and assessment of locations prone to loss of the projected pattern entities.

In some embodiments, the patterned lighting comprises projecting, onto the intra-oral scene, a pattern including a recurrent arrangement of parallel stripes.

In some embodiments, the pattern comprises one or more anchors.

In some embodiments, the anchors are in the form of diagonals intersecting the stripes.

In some embodiments, the stripes are of various widths.

In some embodiments, the pattern comprises multiple color zones.

According to an aspect of some embodiments of the disclosure, there is provided a method for structured light scanning of an intra-oral scene, comprising projecting onto the intra-oral scene a pattern comprising a recurring arrangement of stripes, the pattern comprising one more anchors in the form of diagonals intersecting the stripes; and detecting the projected pattern in an acquired image of the scene.

In some embodiments, the method further comprises constructing a 3D model of the scene, the constructing comprising restoring the pattern in the acquired image utilizing the one or more anchors.

In some embodiments, restoring comprises indexing the anchors directly and further indexing the stripes or portions thereof in accordance with their spatial location relative to the anchors.

In some embodiments, an amount of anchors incorporated in the pattern is selected in accordance with the scene variability.

According to an aspect of some embodiments of the disclosure, there is provided a method for depth imaging using structured light, comprising: projecting onto a scene a color-coded pattern comprising an arrangement of entities; each entity comprising a different narrow band of wavelengths; imaging the projected pattern as a plurality of pixels in an acquired image of the scene, using at least first and second narrowband filters; wherein at least a first portion of the plurality of pixels is associated with the first narrowband filter and at least a second portion of the plurality of pixels is associated with the second narrowband filter; and wherein in the first portion of the plurality of pixels there is less than 10% contribution of the wavelength band transferred by the second filter; estimating the color of each pixel for associating the pixel with the projected color-coded pattern; and determining depth in the scene according to the associating.

In some embodiments, the color coded pattern comprises at least 5 narrowband wavelengths and wherein each of the pixels of the acquired image is associated with one of 5 matching narrowband filters.

In some embodiments, the pixels associated with narrowband filters are evenly distributed over an image sensor of an imager configured for acquiring the image.

According to an aspect of some embodiments of the disclosure, there is provided a system for optical scanning including an intraoral scanning sized and shaped for insertion into a human mouth including a light projector for projecting a pattern including at least a first area illuminated by a first color of light and a second area illuminated by a second color of light and at least one non-illuminated area, an image sensor configured to differentiate between the first color of light and the second color of light, and a processor programmed to determine perform any of the methods described herein.

According to an aspect of some embodiments of the disclosure, there is provided a multispectral light source for intra-oral scanning including a projecting portion configured to fit into an oral cavity, a light source, a plurality of optical components arranged on a light path between the light source and the projecting portion, and light absorbing material arranged in spaces between individual optical components of the plurality of optical components, wherein the optical components includes components selected from a group consisting of interference filters, phosphors, fluorescent nano particles, quantum dots, and AMOLEDs.

In some embodiments, further including a light pipe between the light source and at least one of the plurality of optical components.

In some embodiments, further including a light pipe between at least one of the plurality of optical components and the projecting portion.

In some embodiments, including light sources directed to a first area and a second area, separated by a dark area to which no light sources are directed.

In some embodiments, including an array of light sources including light sources with empty spaces without a light source, the light sources projecting an illuminated pattern and the empty spaces leaving dark areas in the pattern.

According to an aspect of some embodiments of the disclosure, there is provided a light source for intra-oral scanning including an array of separately controlled light sources.

According to an aspect of some embodiments of the disclosure, there is provided a method of producing a pattern of illumination in intra-oral scanning including activating one or more light sources to create light areas of a pattern and keeping some light sources inactivated to create dark areas of the pattern.

In some embodiments, the array includes light sources configured to emit more than one wavelength of light.

In some embodiments, the light source includes at least one light source selected from a group consisting of LEDs, microLEDs, quantum dots, nano-particles, AMOLEDs and VCSELs.

According to an aspect of some embodiments of the present invention there is provided an intra-oral optical scanning method for intra-oral optical scanning including projecting a pattern, the pattern including at least a first area illuminated by a first color of light and a second area illuminated by a second color of light and at least one non-illuminated area onto an intra-oral feature, making a first image of the first area, the second area and the non-illuminated area differentiating between the first color of light and the second color of light in the first image of the projected pattern, and determining from the image of the non-illuminated area at least one of an ambient light level, a level of scattered light, a level of light absorption and a level of light reflected from at least one of the first area and the second area.

According to some embodiments of the invention, further including estimating a color of the first area from the image of the first area and correcting the estimated color for at least one of the ambient light and a scattered background light.

According to some embodiments of the invention, the correcting includes subtracting an estimated value of at least one of the ambient light and a scattered background from a light level of the first area.

According to some embodiments of the invention, further including estimating a color of the first area from the first image, illuminating the first area, the second area and the non-illuminated area under the same illumination conditions, second imaging the first area, the second area and the non-illuminated area under the same illumination conditions, thereby producing a second image, and correcting the estimated color based on the second image.

According to some embodiments of the invention, further including correcting an estimated position of the first area for light scattered from below a surface the first area.

According to some embodiments of the invention, further including correction for at least one of local reflection, scattering, absorption coefficients, incidence angle of the projected light, an angle to the imager, distance to projector and distance to the imager.

According to some embodiments of the invention, further including third imaging the first area under ambient light conditions, wherein the determining a level of scattered light is based on the third imaging.

According to some embodiments of the invention, the determining of a level of scattering includes estimating at least one of a scattering and an absorption coefficient of a material of the first area.

According to some embodiments of the invention, further including making a depth map of the first area and correcting the estimated color of the first area based on at least one of a relative position of the first area with respect to an imager making at least one of the image and a relative position of the first area with respect to an illumination source.

According to some embodiments of the invention, further including segmenting an image of the first area based on measured optical properties.

According to some embodiments of the invention, further including estimating an optical property of an obscured area.

According to some embodiments of the invention, further including estimating an optical property of two subsurface areas at different depths below a surface.

According to some embodiments of the invention, further including estimating an optical property of a subsurface area.

According to some embodiments of the invention, further including measuring a fluorescence of the first area.

According to some embodiments of the invention, the fluorescence is used for estimating enamel demineralization.

According to some embodiments of the invention, estimating enamel demineralization is performed by at least one of fluorescence optical absorption and optical scattering.

According to some embodiments of the invention, further including identifying an intra-oral feature based on estimated optical properties.

According to some embodiments of the invention, further including segmenting an image of the first area based on estimated optical properties.

According to some embodiments of the invention, further including applying deep learning configured to improve at least one of the identifying and the segmenting.

According to some embodiments of the invention, the intra-oral feature is a biofilm.

According to some embodiments of the invention, the identifying is based on detecting a fluorescence.

According to some embodiments of the invention, further including displaying a 3D model that simulates at least one of measured absorption and scattering.

According to some embodiments of the invention, further including identifying a manufacturer of a restoration based on optical properties of the first area.

According to some embodiments of the invention, further including acquiring a new restoration from the manufacturer.

According to some embodiments of the invention, further including choosing a material for a restoration to match an optical property of an intraoral object.

According to some embodiments of the invention, further including choosing multiple materials for a restoration to match an optical property of a plurality of layers of an intraoral object.

According to some embodiments of the invention, further including manufacturing the restoration.

According to some embodiments of the invention, the manufacturing includes additive manufacturing.

According to some embodiments of the invention, further including collecting color information for a plurality of sections, each section illuminated by a plurality of colors, producing a model to classify an object's shade information, and using a probe to mark a desired location for collecting color data of an intra-oral feature.

According to some embodiments of the invention, using the probe includes using the probe to set a specific distance between the imager and the intra-oral feature.

According to some embodiments of the invention, using the probe includes using the probe to set a specific angle between an optic axis of the imager and the intra-oral feature.

According to some embodiments of the invention, the plurality of colors is obtained from the projected pattern.

According to some embodiments of the invention, the producing includes accounting for at least one of a distance and an angle between a light source and the imager and the each section in the each image.

According to some embodiments of the invention, the producing includes accounting for an effect of ambient light in at least one section in the each image.

According to some embodiments of the invention, further including producing an indication for a user that at least one of distance and/or angle between an Intra Oral Scanner (IOS) and a measured tooth or position over the measured tooth are at a given tolerance for shade measurement.

According to an aspect of some embodiments of the present invention there is provided an Intra-Oral-Scanner (IOS) including a stand-off component defining at least one of a distance and an angle to an imaged surface.

According to some embodiments of the invention, the stand-off component includes a probe.

According to some embodiments of the invention, the probe is shaped as a hollow tube.

According to some embodiments of the invention, the stand-off component includes a frame for placing on an intra-oral feature.

According to an aspect of some embodiments of the present invention there is provided a structured light based 3D measurement system including at least one imager, at least one pattern projector and a processing unit to determine 3D information from image information obtained by the imager of a pattern projected on scene by the pattern projector, wherein the pattern projector includes a non-circular aperture.

According to some embodiments of the invention, the projected pattern is aligned to have lower spatial frequencies at a direction of a long axis of the non-circular aperture.

According to some embodiments of the invention, the projected pattern includes a colored stripes pattern, and the direction along the stripes is aligned along the long axis of the non-circular aperture.

According to some embodiments of the invention, dimensions of the non-circular aperture are configured for providing a different effective F number along major axes of the non-circular aperture to control Depth-Of-Field (DOF) and power loss of the projected pattern.

According to some embodiments of the invention, the effective F number along a major axis of the non-circular aperture is between 2.5 and 6 and the effective F number along a minor axis of the non-circular aperture is between 0.5 and 2.5.

Unless otherwise defined, all technical and/or scientific terms used herein have the same meaning as commonly understood by one of ordinary skill in the art to which the various embodiments of the various inventions disclosed herein pertain. Although methods and materials similar or equivalent to those described herein can be used in the practice or testing of various embodiments of the disclosure, exemplary methods and/or materials are described below. In case of conflict, the patent specification, including definitions, will control. In addition, the materials, methods, and examples are illustrative only and are not intended to be necessarily limiting.

Implementation of methods and systems of the various embodiments disclosed herein can involve performing or completing selected tasks manually, automatically, or a combination thereof Moreover, according to actual instrumentation and equipment of embodiments of such disclosed methods and systems disclosed herein, several selected tasks could be implemented by hardware, by software or by firmware or by a combination thereof using an operating system.

For example, hardware for performing selected tasks according to some embodiments disclosed herein can be implemented as a chip or a circuit. As software, selected tasks according to some embodiments disclosed herein could be implemented as a plurality of software instructions being executed by a computer using any suitable operating system. In an exemplary embodiment of the disclosure, one or more tasks can be performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL
VIEWS OF THE DRAWINGS

Some embodiments of the disclosure are herein described, by way of example only, with reference to the accompanying drawings. With specific reference now to the drawings in detail, it is stressed that the particulars shown are by way of example and for purposes of illustrative discussion of the disclosed embodiments. In this regard, the description taken with the drawings makes apparent to those skilled in the art how embodiments disclosed herein may be practiced.

Figure 3:
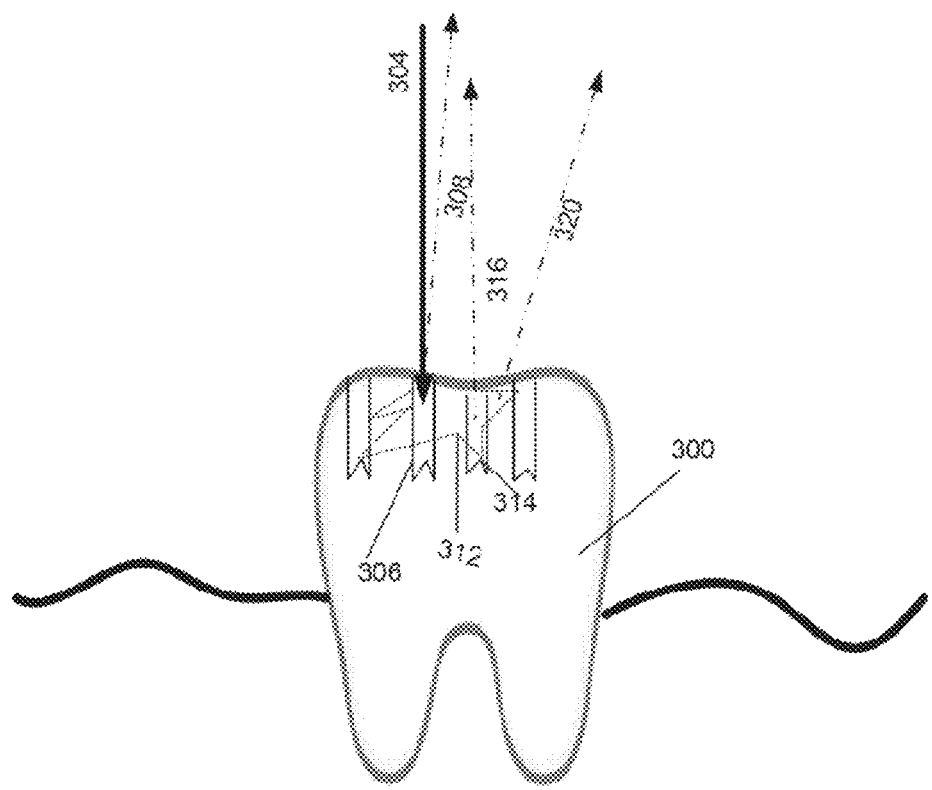
Figure 4A:
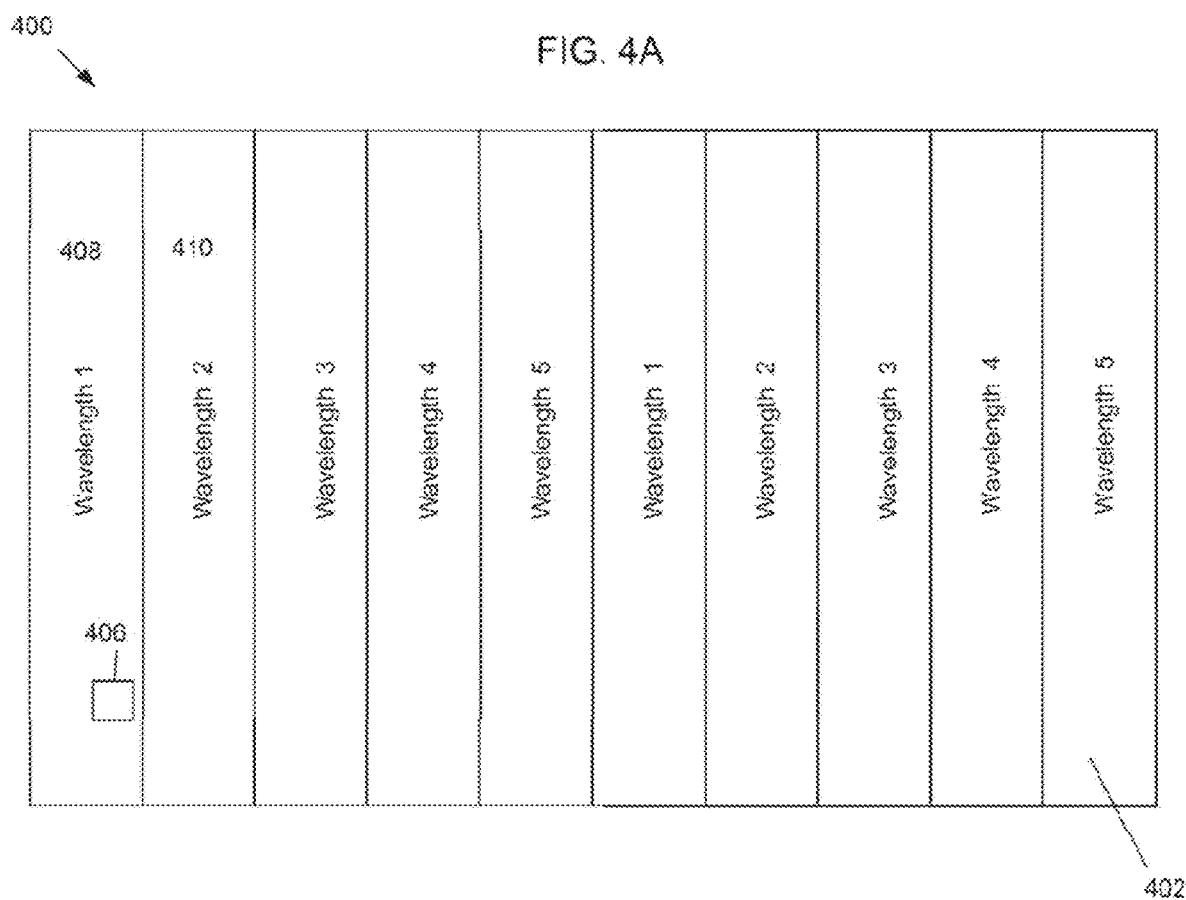
Figure 4B:
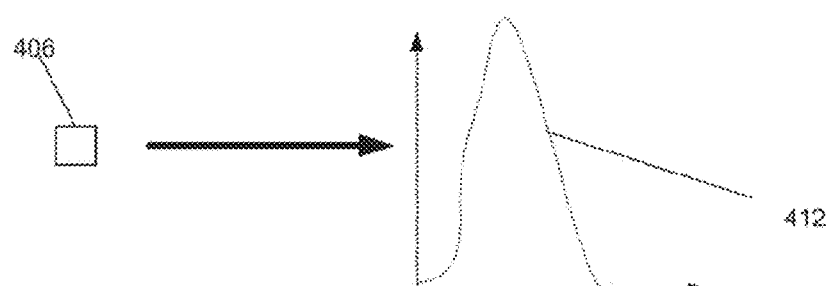
Figure 5A:
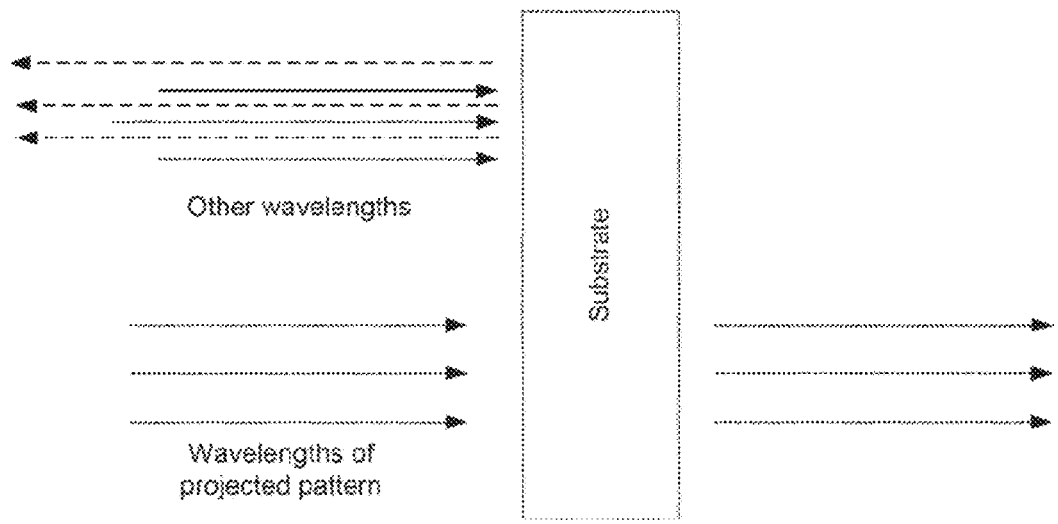
Figure 5B:
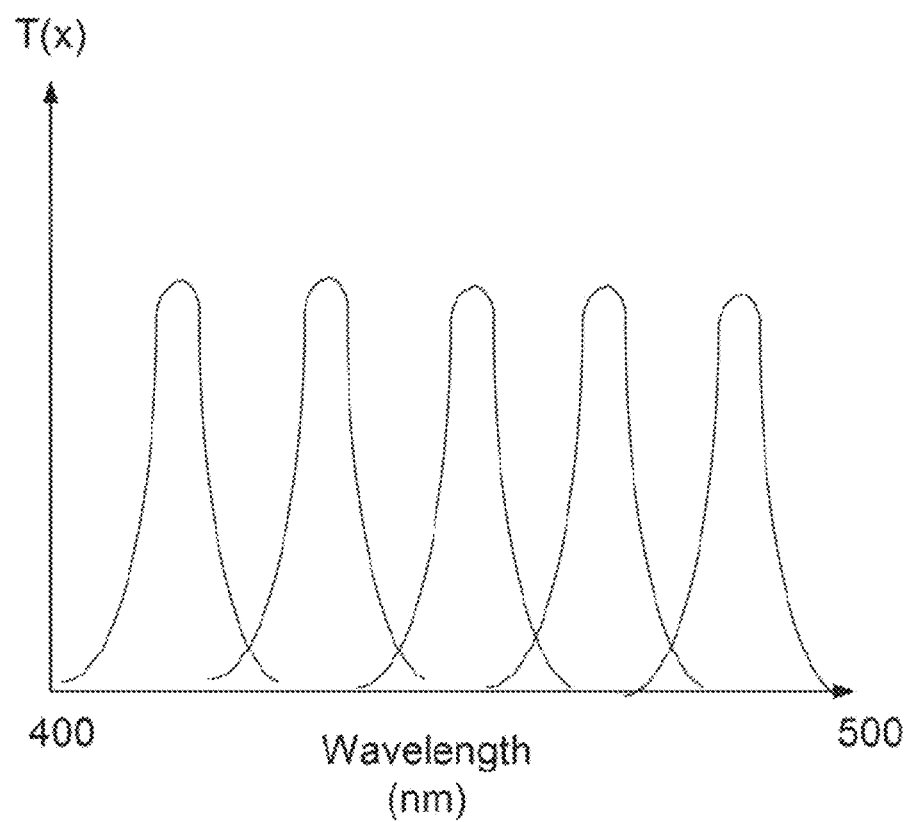
Figure 6A:
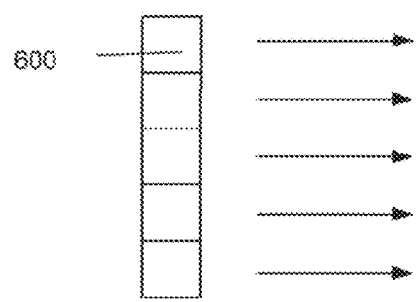
Figure 7:
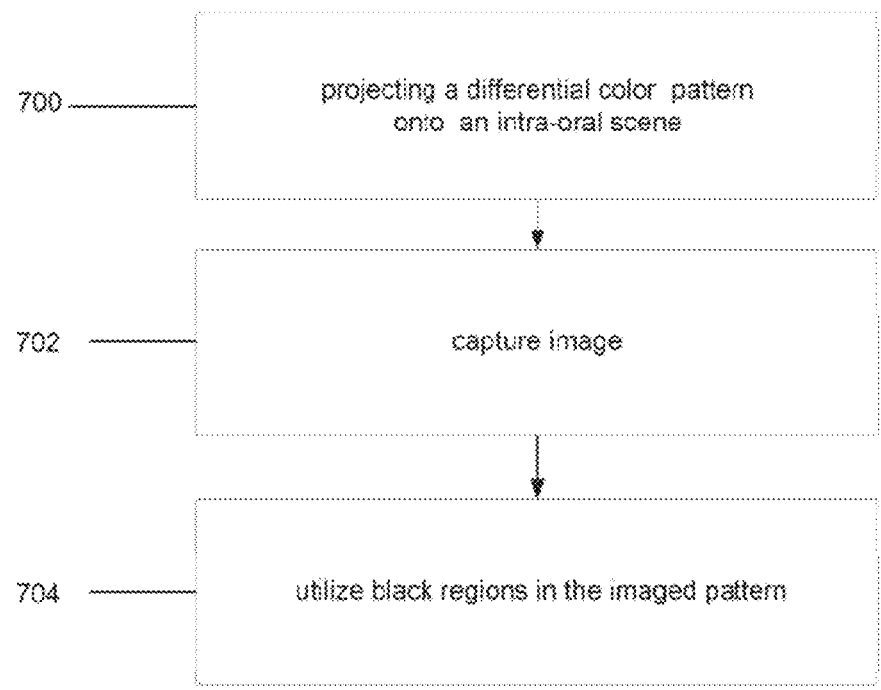
Figure 8:
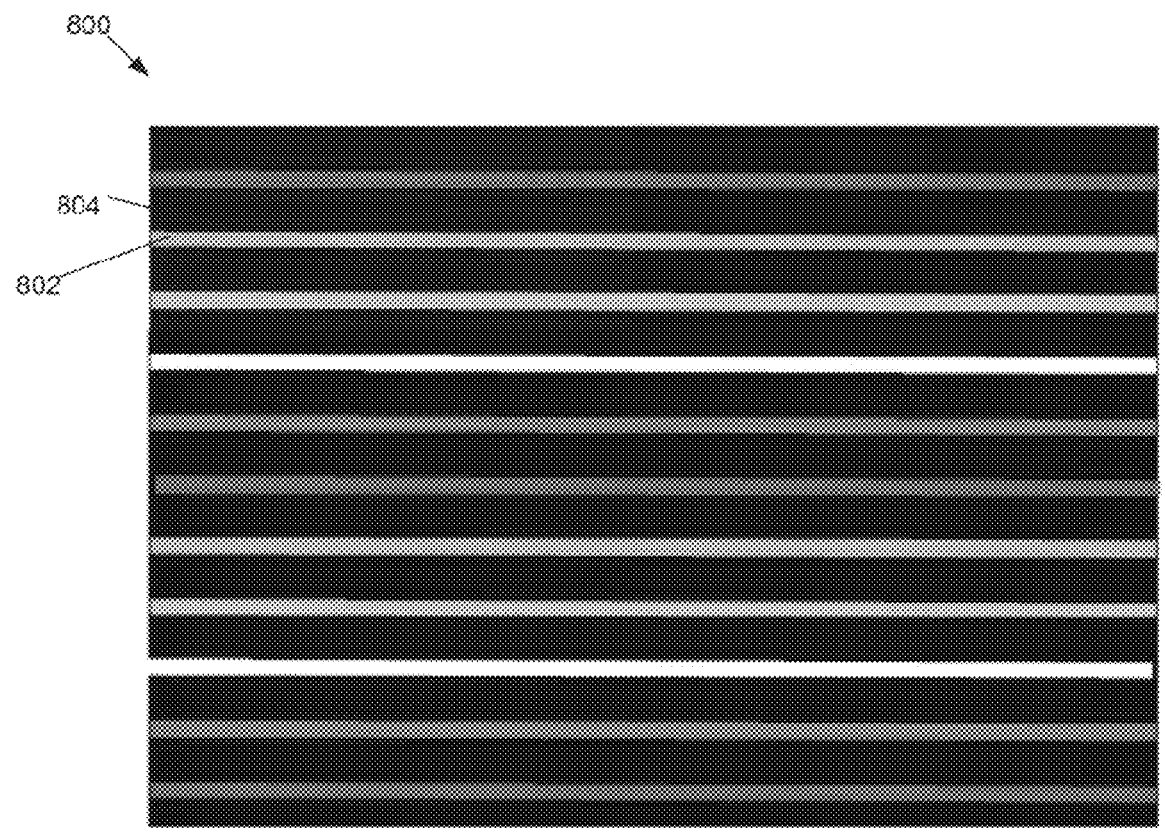
Figure 9:
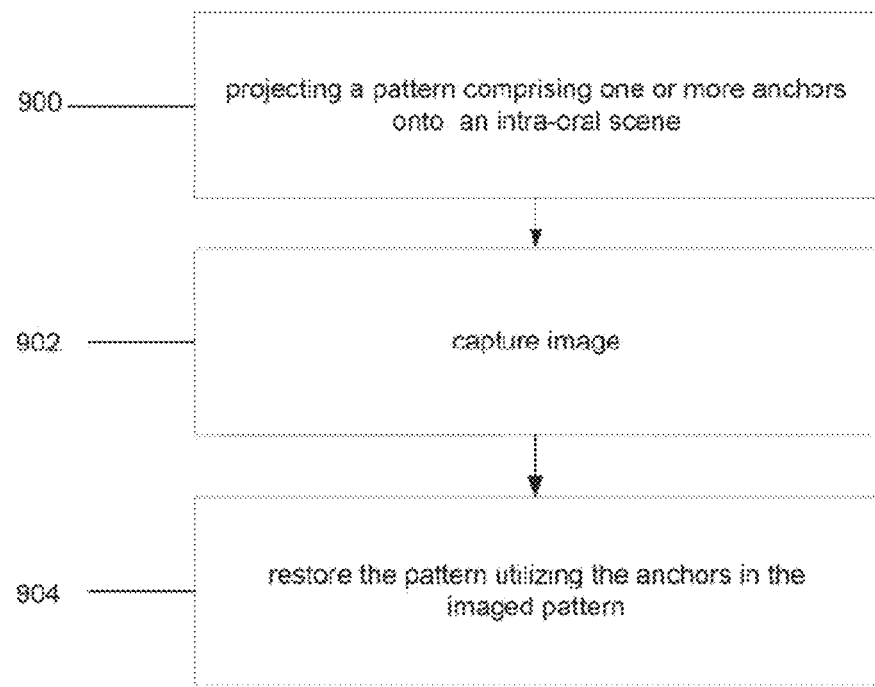
Figure 10:
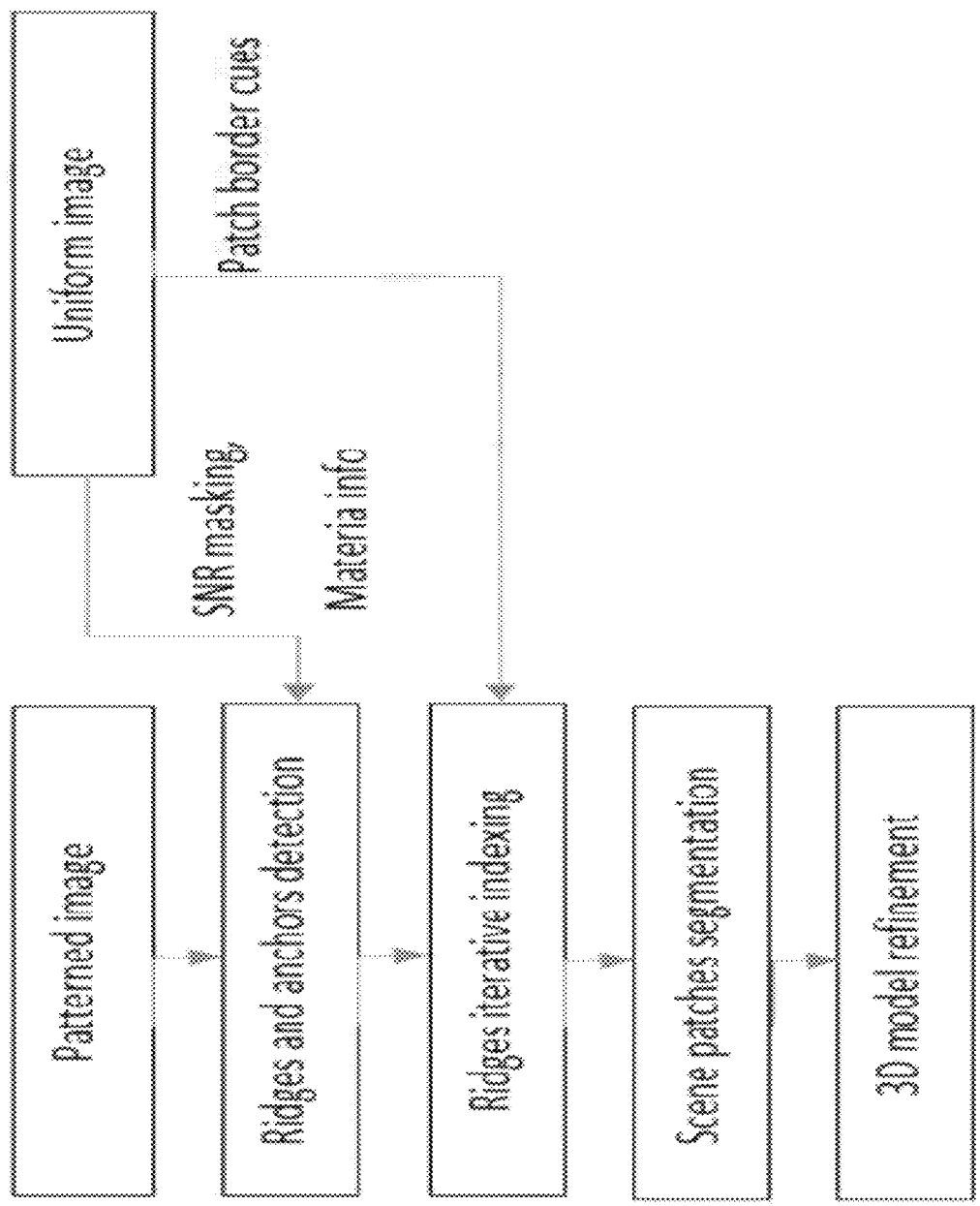
Figure 11:
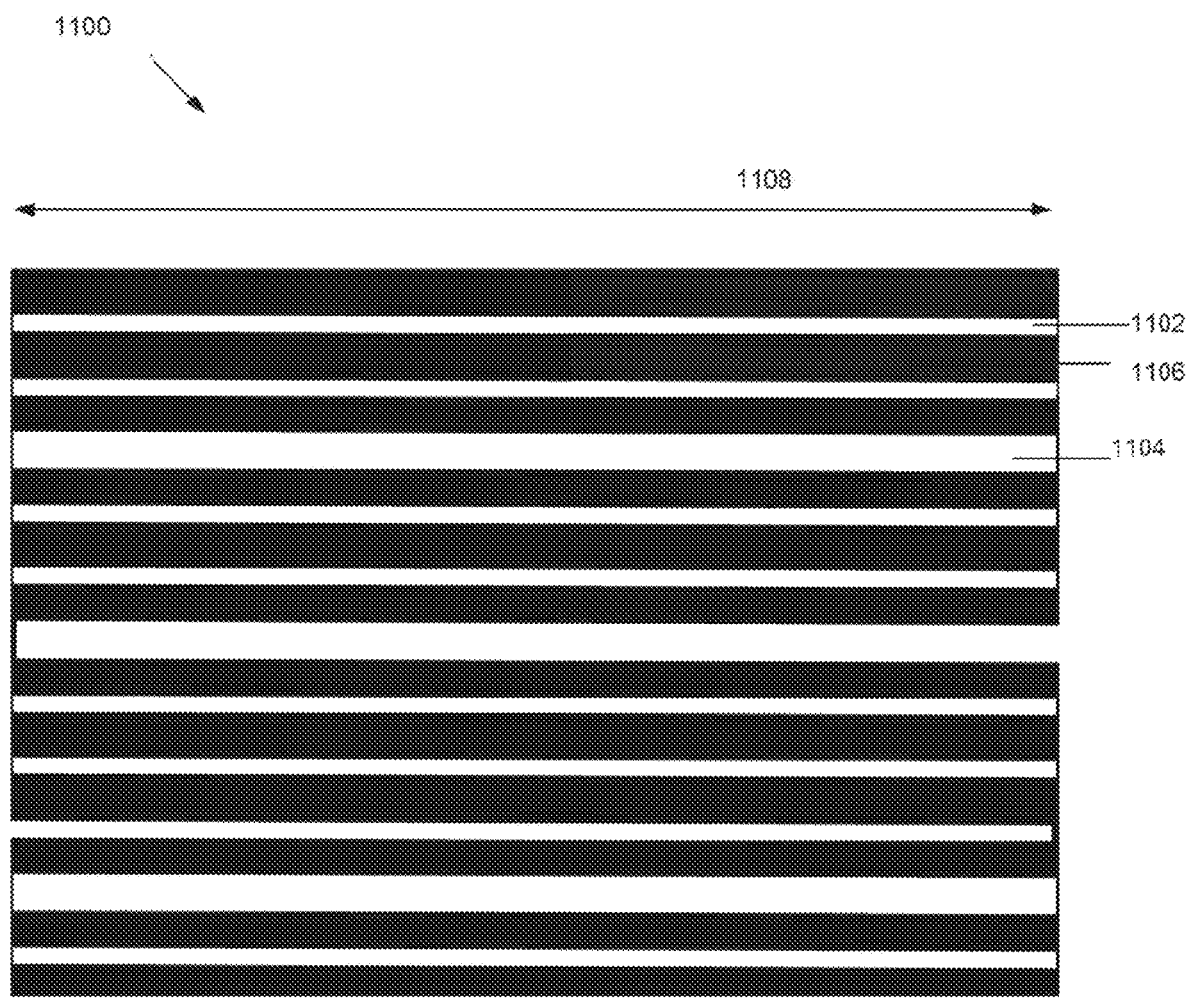
Figure 12:
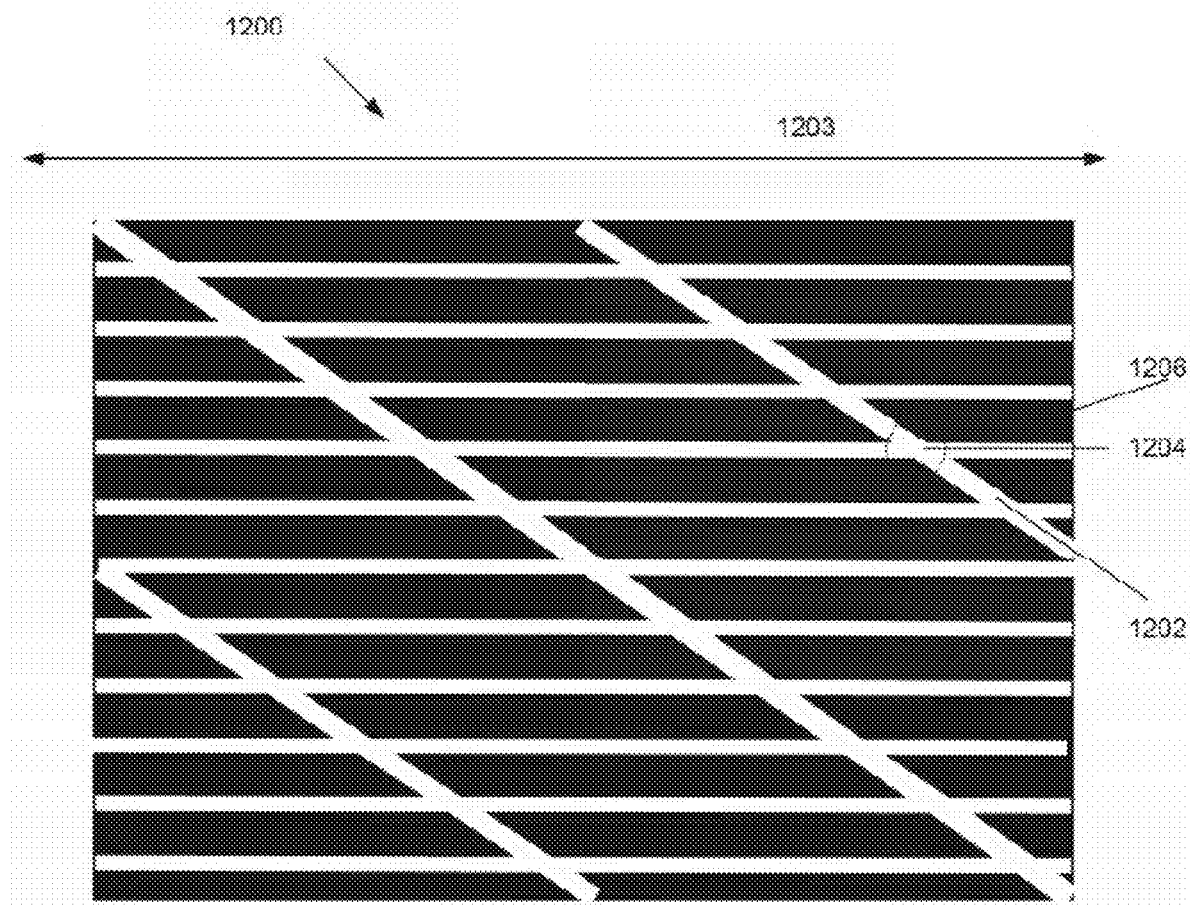
Figure 13A:
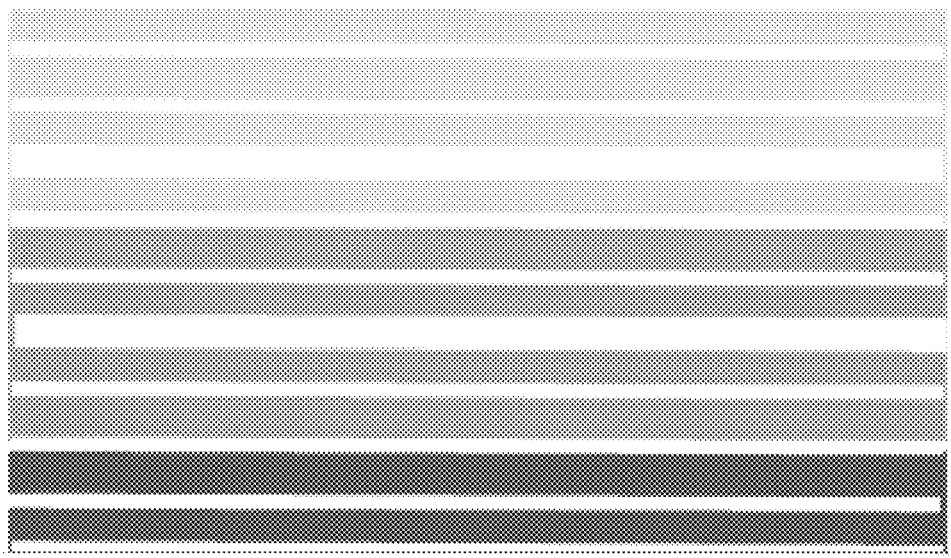
Figure 13B:
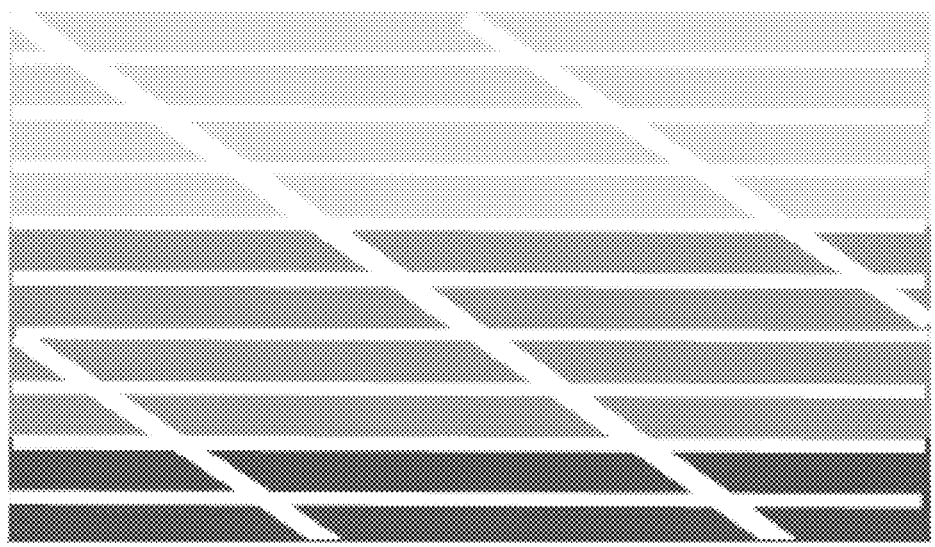
Figure 14:
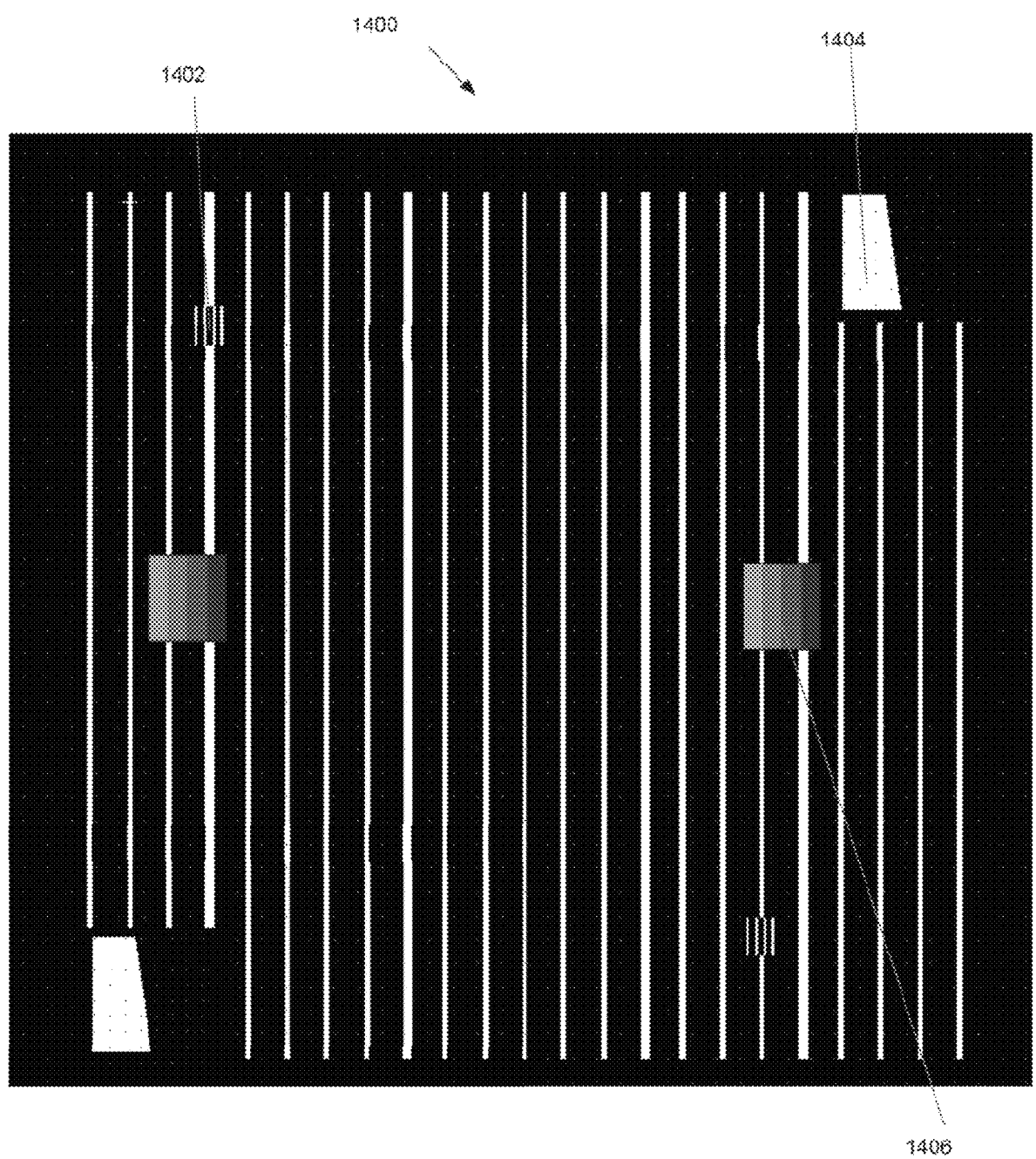
Figure 15:
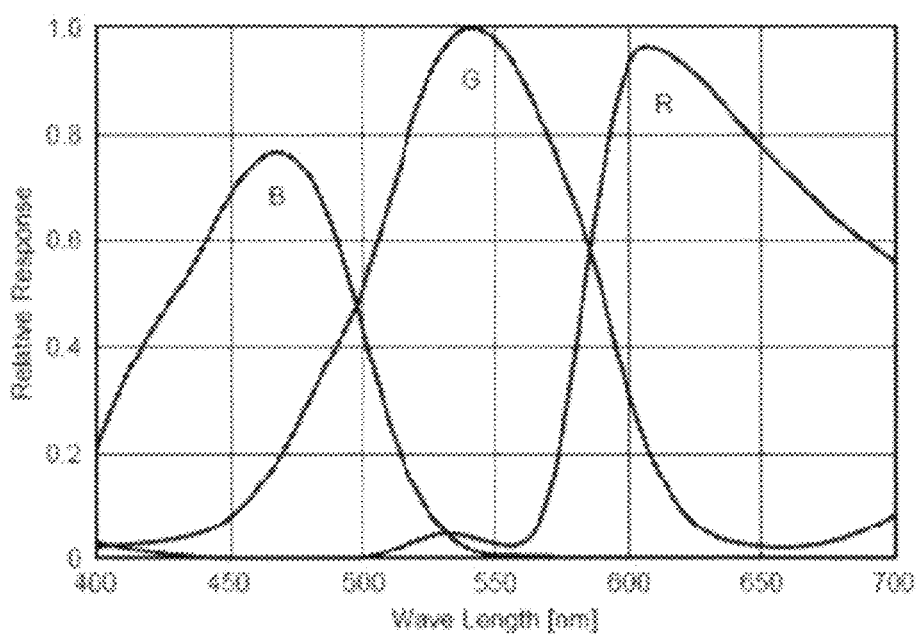
Figure 16:
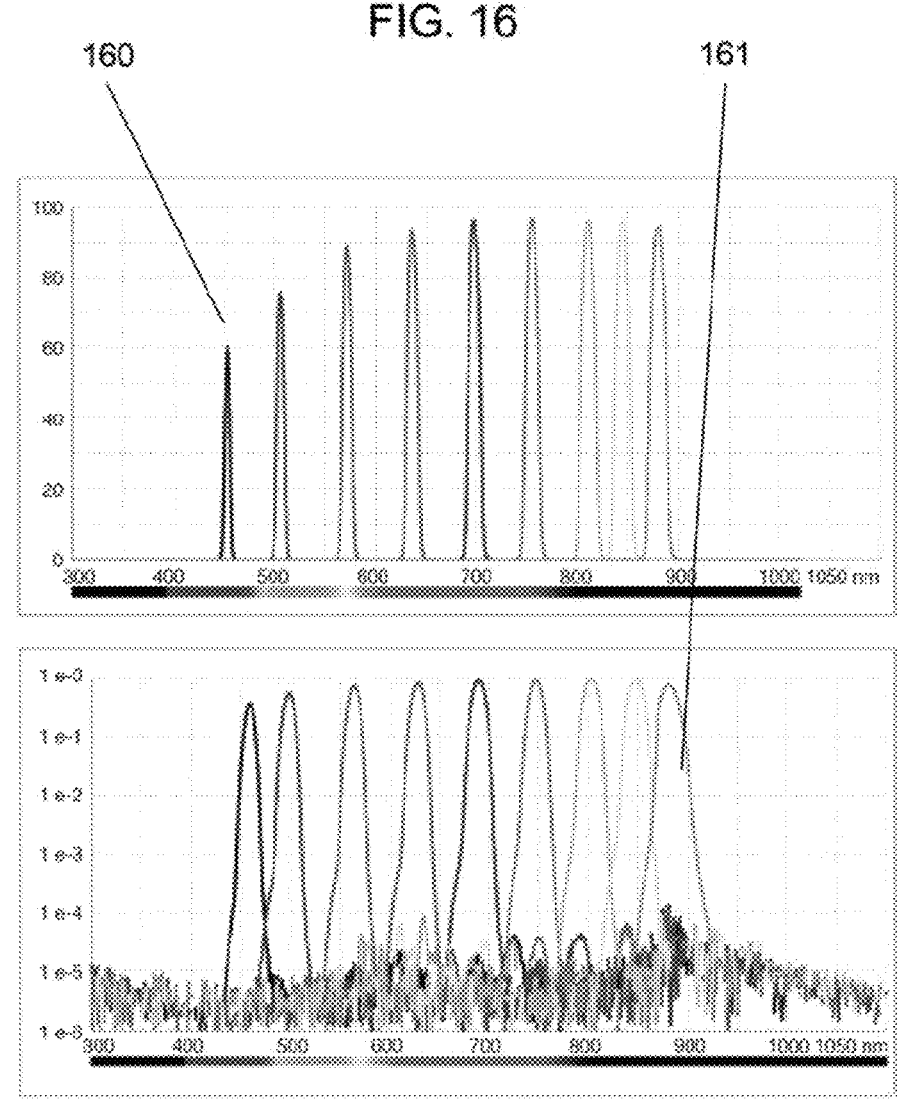
Figure 17:
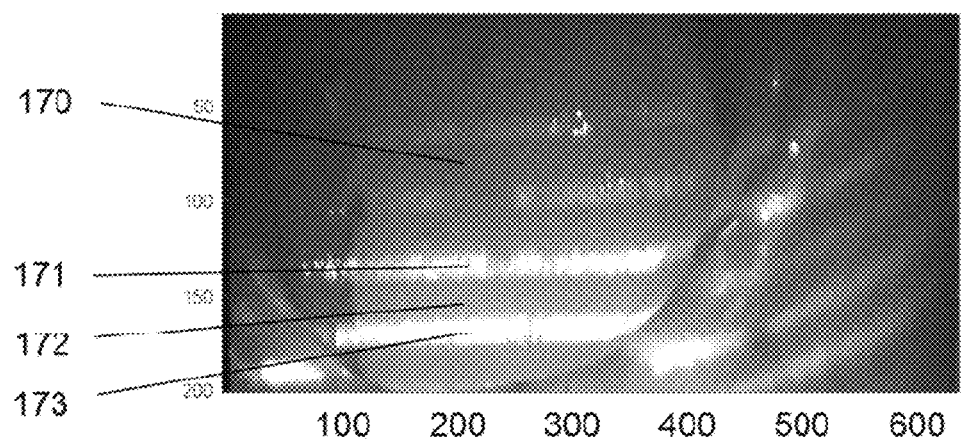
Figure 19:
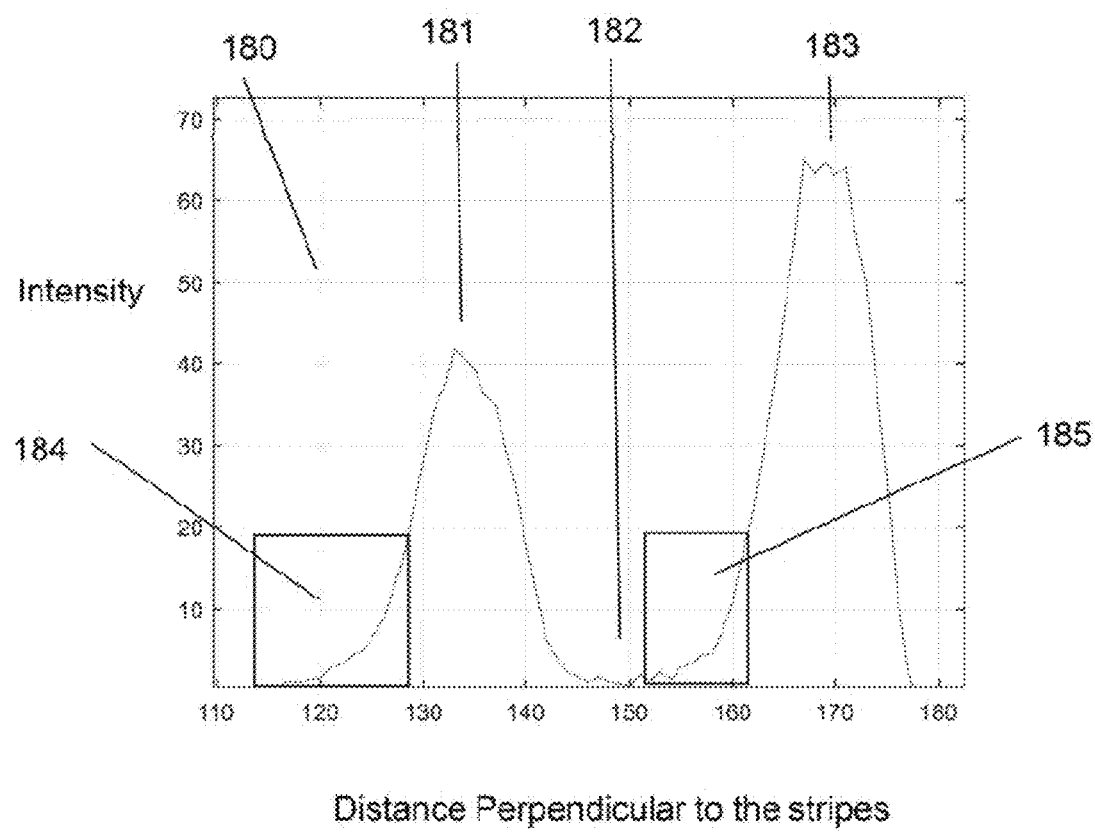
Figure 20A:
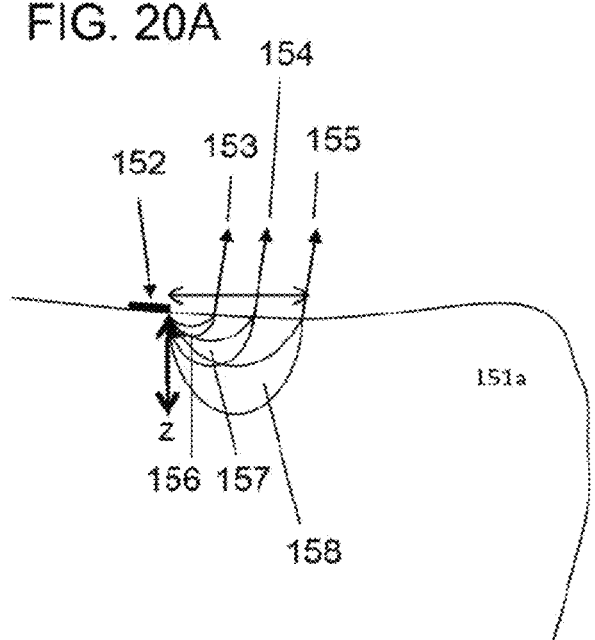
Figure 20B:
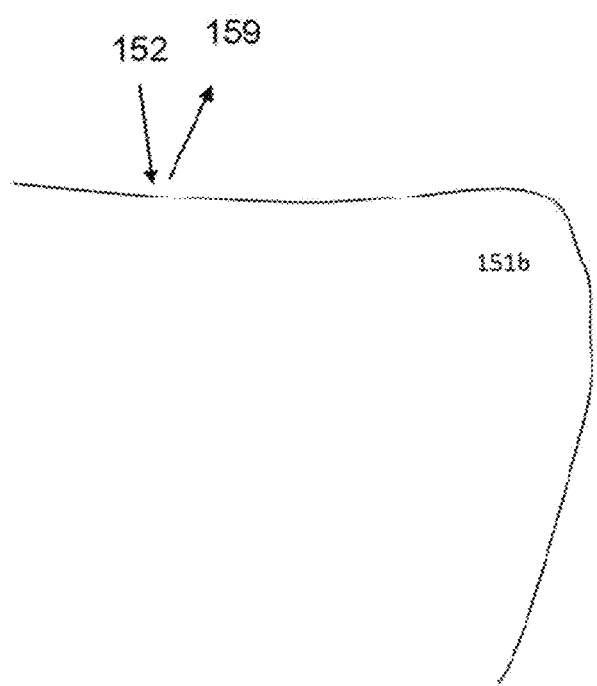
Figure 20C:
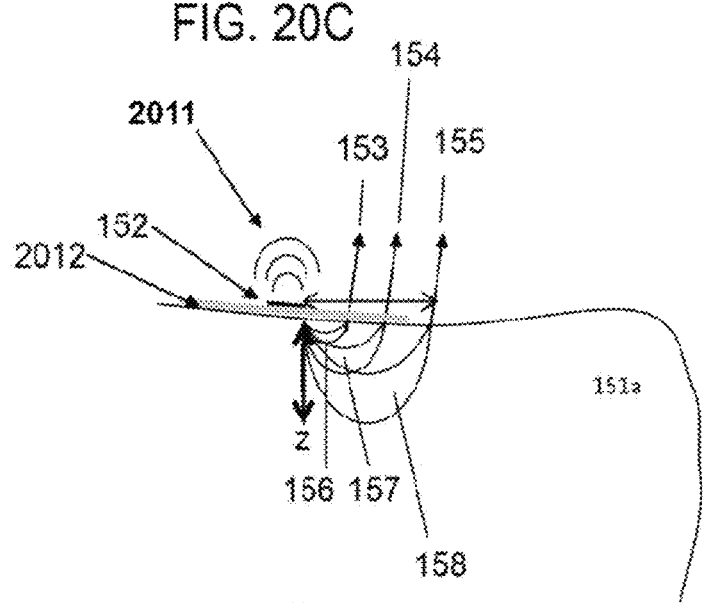
Figure 20D:
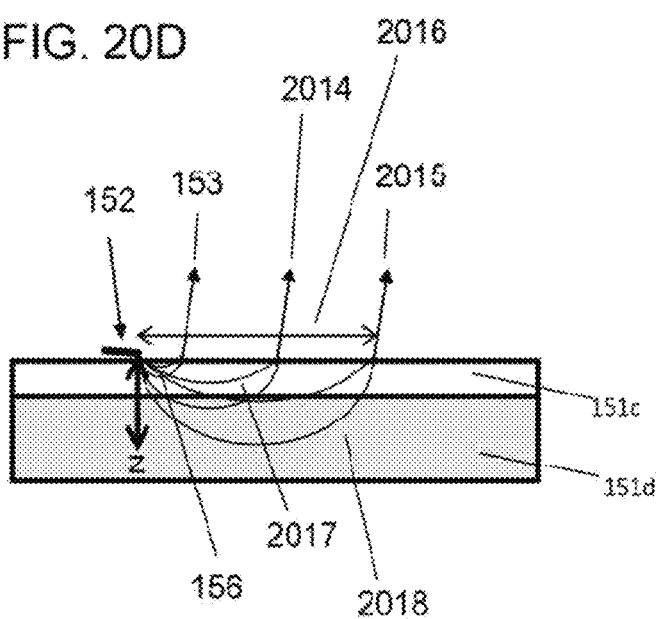
Figure 21:
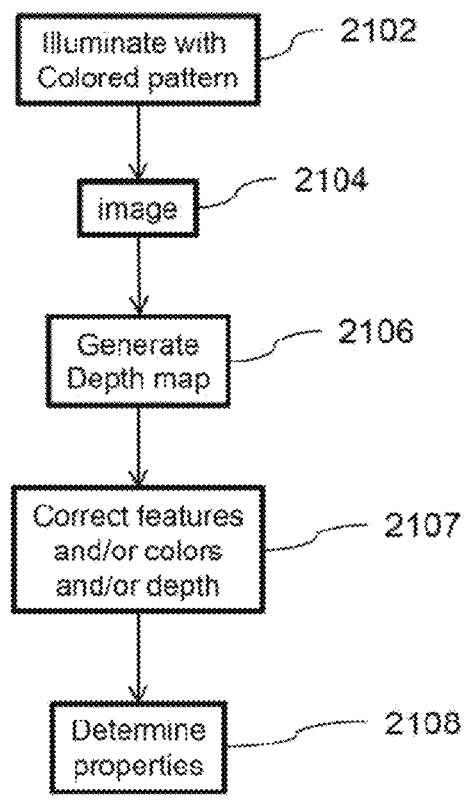
Figure 22:
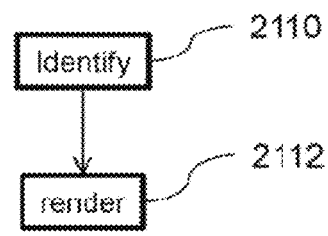
Figure 23:
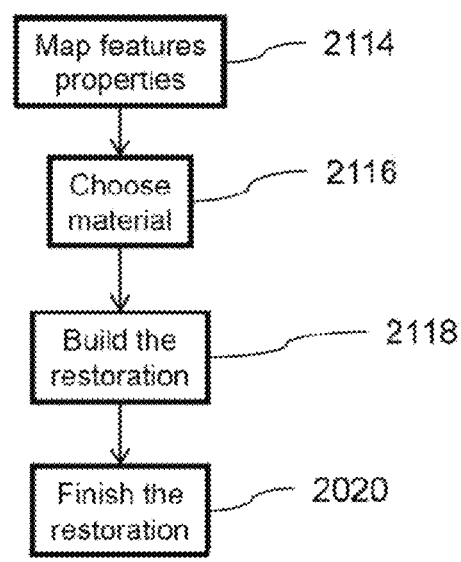
Figure 24:
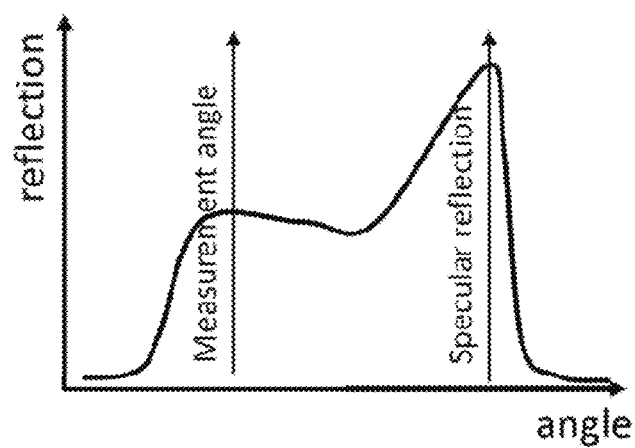
Figure 25A:
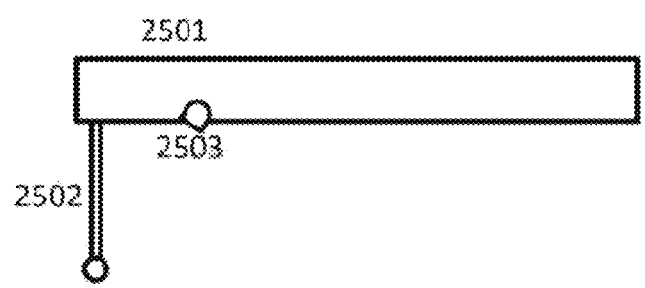
Figure 25B:
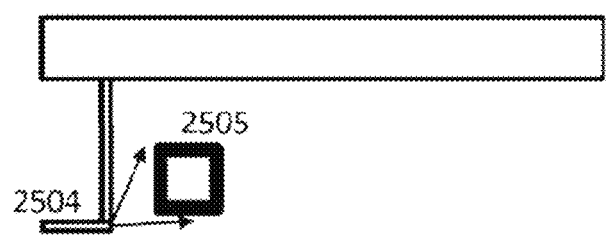
Figure 25C:
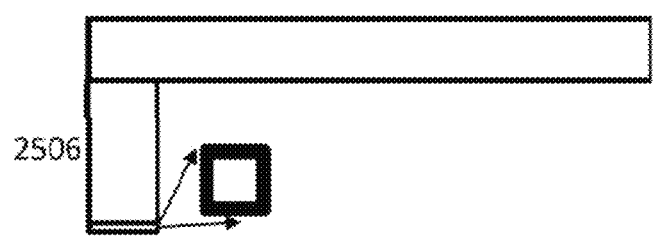
Figure 25D:
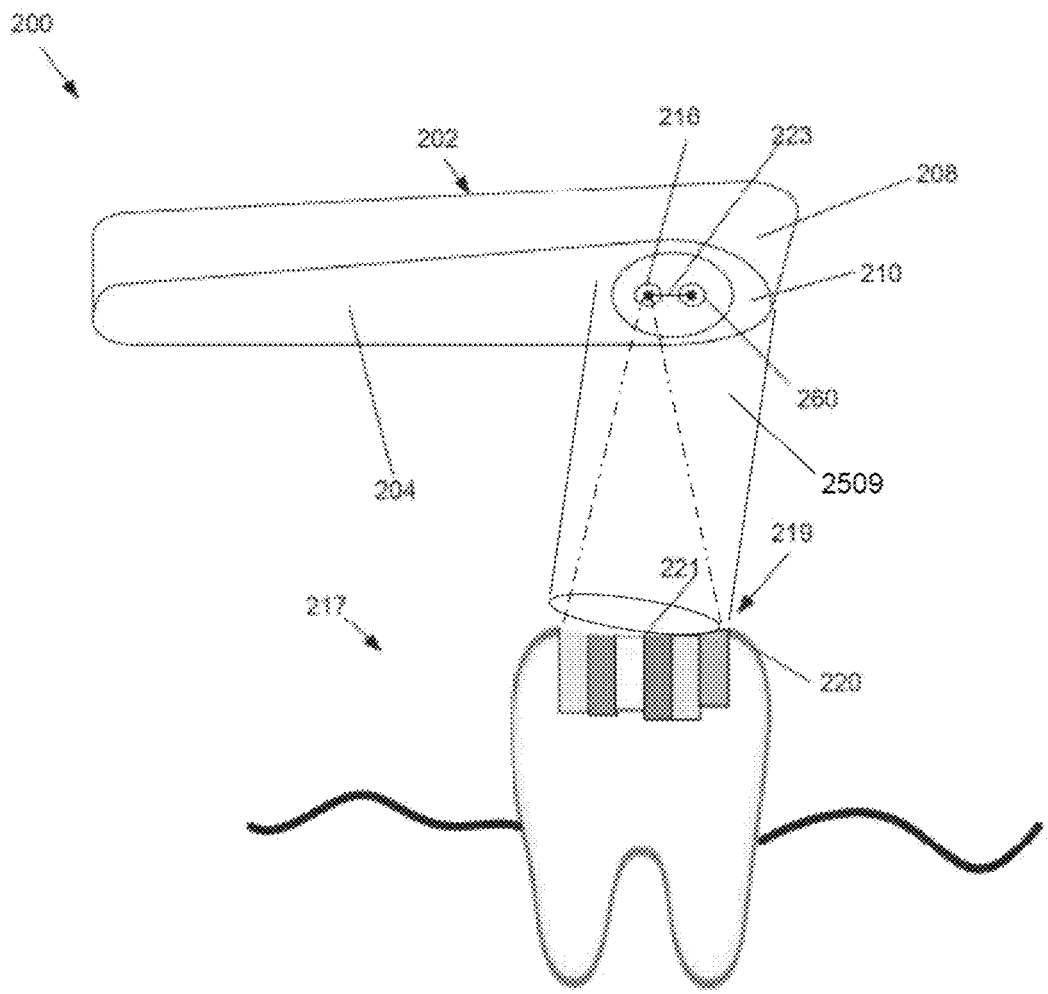
Figure 26:
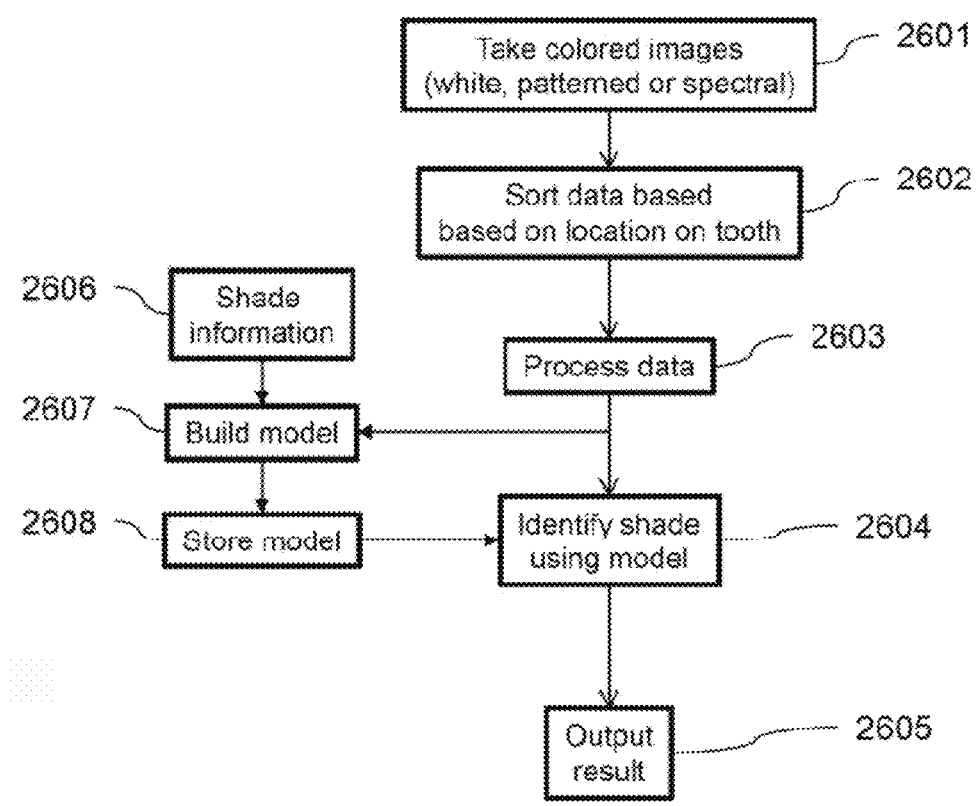
Figure 27:
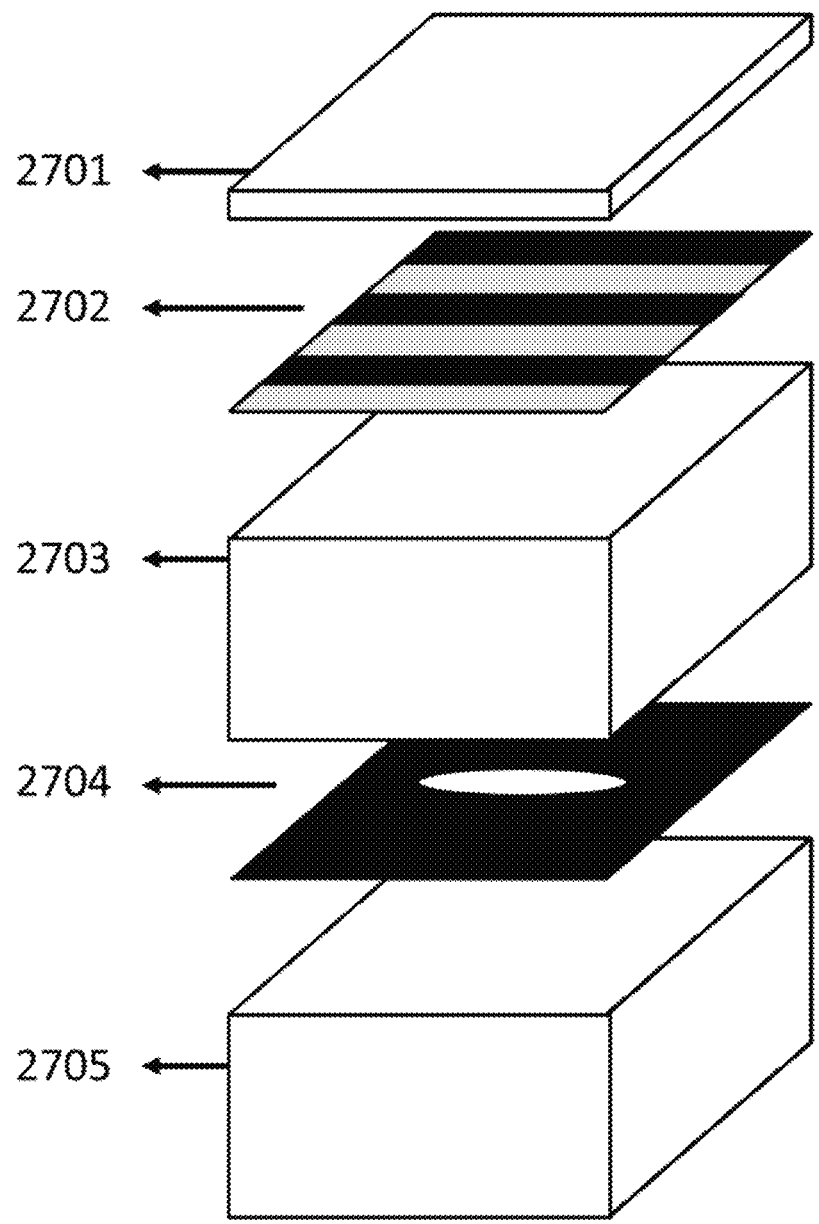

FIG. 3 schematically illustrates interaction between projected light and the tooth and/or other oral content, according to some embodiments of the disclosure;

FIGS. 4A-B are an example of a multi-wavelength pattern for projecting onto an intra oral scene (FIG. 4A), and a schematic spectral graph of an exemplary pixel of the image (FIG. 4B), according to some embodiments of the disclosure;

FIGS. 5A-B schematically illustrate transmission of filters used at detection of the pattern, according to some embodiments of the disclosure;

FIGS. 6A-Q are various configurations for projecting a multi-wavelength pattern onto an intra-oral scene, according to some embodiments of the disclosure;

FIG. 7 is a flowchart of a method for scanning an intra-oral scene using a referential color pattern, according to some embodiments;

FIG. 8 is an example of a referential color pattern, according to some embodiments of the disclosure;

FIG. 9 is a flowchart of a method for scanning an intra-oral scene using a pattern comprising one or more anchors, according to some embodiments of the disclosure;

FIG. 10 is a flowchart of a method for processing an imaged pattern, according to some embodiments of the disclosure;

FIG. 11 is an example of a monochrome pattern comprising stripes having various widths, according to some embodiments of the disclosure;

FIG. 12 is an example of a monochrome pattern comprising one or more diagonals, according to some embodiments of the disclosure;

FIGS. 13A-B are examples of patterns comprising color zones, according to some embodiments of the disclosure;

FIG. 14 is an example of a pattern comprising one or more calibration elements, according to some embodiments of the disclosure;

FIG. 15 is an exemplary illustration of color sensitivity bands of a Bayer filer (source U.S. Pat. No. 9,593,982 FIG. 2);

FIG. 16 is an exemplary illustration of narrow color bands (source Pierre-Jean Lapray et al. Multispectral Filter Arrays: Recent Advances and Practical Implementation, Sensors 2014, 14(11), 21626-21659; doi:10.3390/s141121626);

FIG. 17 illustrates an image of referential stripes pattern illuminated over a tooth in accordance with an embodiment of the present disclosure;

FIGS. 18A and 18B illustrate structures of a sensor array in accordance with embodiments of the current disclosure;

FIG. 19 illustrates a light intensity along a line crossing two projected stripes after local subtraction of background ambient and/or scattered illumination according to referential black gap center illumination in accordance with an embodiment of the current disclosure;

FIGS. 20A-D are schematic illustrations of paths of light interacting with intra-oral objects in accordance with an embodiment of the current disclosure FIG. 21 is a flowchart illustration measuring optical properties of an intra dental feature in accordance with an embodiment of the current disclosure;

FIG. 22 is a flow chart illustration of identifying intra-oral features in accordance with an embodiment of the current disclosure;

FIG. 23 is a flow chart illustration of producing an object for oral restoration in accordance with an embodiment of the current disclosure;

FIG. 24 is a schematic illustration of a BSDF (bidirectional scattering distribution function) diagram of a tooth showing angles of specular reflection in accordance with an embodiment of the current disclosure;

FIGS. 25A-C illustrate embodiments of an IOS with a standoff in accordance with embodiments of the current disclosure;

FIG. 25D is a schematic illustration of a 3D intra-oral scanner system, according to some embodiments of the disclosure;

FIG. 26 illustrates a process of measuring a shade in accordance with an embodiment of the current disclosure; and FIG. 27 is a simplified illustration of a light projector which includes a non-circular aperture according to an example embodiment of the invention.

DESCRIPTION OF SOME OF THE EMBODIMENTS

Some embodiments of the present disclosure relate to dental measurements, and more particularly, but not exclusively, to optical patterns for intra-oral scanning.

Some embodiments of the present disclosure relate to use of structured light for constructing a 3D model of the intra-oral scene. In some embodiments, scanning is performed using a hand-held intra oral scanner (IOS) configured for projecting one or more patterns onto the intra-oral scene, and imaging the scene with at least one imager.

A broad aspect of some embodiments of the present disclosure relates to reducing cross talk between structured illumination entities in dental imaging. For example spatial crosstalk and/or miss identification of projected entities may result in inaccurate measurements of structure. Optionally, spectral differentiation is used to identify projected entities and/or reduce spatial crosstalk.

In some embodiments, narrow band illumination and/or spectral imaging are used to reduce spectral crosstalk. Optionally, reducing spectral crosstalk reduces misidentification of a projected object. In some cases, misidentification of a projected object may lead to an incorrect model of the structure, geometry of an object. For example, an imager with narrow band filters may be used to reduce spectral crosstalk.

In some embodiments, crosstalk is caused by properties of the measurement device and/or the light projector and/or due to ambient light and/or due to properties of the object being imaged. In some embodiments, use of spectral differentiation may reduce one some or all of these forms of crosstalk.

An aspect of some embodiment of the current disclosure relates to projecting spectrally differentiated entities separated by dark areas onto a dental scene. Optionally, the dark areas are imaged. Optionally, a dark area is imaged. For example, measurements of light imaged in a dark area may be used to correct an effect of ambient light and/or to correct an effect of smearing on a measured light a projected entity.

An aspect of some embodiments of the present disclosure relates to choosing spectral bands that can produce accurate images on a dental surface. For example, high frequency light may be used to reduce scattering caused by translucency of teeth. For example, multiple narrow bands of light may be projected in the blue-violet bands. Narrow spectral filters are optionally used to differentiate between the narrow illumination bands.

An aspect of some embodiments of present disclosure relates to using both black and white and spectrally differentiated projected objects and/or detection bands. Optionally, black and white imaging is used to increase sensitivity. Optionally, spectral differentiation of projected objects is used to increase sensitivity and/or to reduce crosstalk.

An aspect of some embodiments of the current disclosure relates to adapting a spectral imager to imaging of a dental scene. For example, a Bayer filter imager may be configured with additional pixel sensors in high frequency (violet-blue-green bands) and/or fewer sensors in the low frequency (red) bands. Alternatively or additionally, the sensor may include a mixture of black and white pixel sensors and color sensors.

A broad aspect of some embodiments of the disclosure relates to spatial coding using a light pattern. In some embodiments, due to the plurality of tissue types, structures and/or materials (natural and/or artificially introduced materials) in the intra-oral scene, and/or due to properties of the optical elements of the IOS, the imaged pattern is smeared relative to the one that was projected. Some embodiments of the disclosure relate to identifying and separating the projected pattern entities from each other in an image. For example, the image may be used for reconstructing the pattern in a model of the scene.

In some embodiments, when choosing a light pattern that can be successfully restored, one or more restrictions such as the plurality of imaged materials, optical properties of the teeth and tissues, and/or inherent intra and/or extra-oral movement of the operator (which may limit time sequencing of the pattern with respect to the IOS's FPS rate) are taken into consideration.

An aspect of some embodiments relates to projection of a pattern onto an intra-oral scene and/or detection of the pattern that are suitable to reduce optical crosstalk between adjacent pattern entities, such as stripes. In some embodiments, crosstalk between the pattern entities is reduced by utilizing black spaces between adjacent pattern entities. Alternatively or additionally, optical crosstalk may be reduced by using spectrally differentiated projected entities and spectral differentiation, for example using an imaging spectrometer (e.g. a color camera and/or a hyperspectral camera). Optionally, the use of spectral differentiation reduces crosstalk between nearby projected entities. For example, increasing the specificity of the spectral differentiation may facilitate differentiation of projected entities with smaller black spaces and/or without the use of black spaces. For example, spectral differentiation may by increased by narrowing the width of a detected spectral band. For example in some embodiments, a hyperspectral camera may increase spectral differentiation and/or reduce spectral crosstalk compared to a Bayer filter camera.

In some embodiments, crosstalk may be reduced by wavelength coding. For example, wavelength coding may be advantageous in the case of significant smearing (e.g. as in projecting pattern over a tooth). For example, wavelength coding may be advantageous, when imaging teeth. In some embodiments, wavelength coding includes projecting a series of colored lines. For example, the colored lines be projected in a de Bruijn colored sequence. In some embodiments, light pattern projection methods and/or image acquiring methods may include techniques and/or equipment as described, for example, in "Rapid shape acquisition using color structured light and multi-pass dynamic programming" L Zhang, B Curless, SM Seitz—3D Data Processing, 2002. In some cases, optical crosstalk includes spatial crosstalk. For example, spatial crosstalk may include smearing of a light pattern over space. In some cases, spatial crosstalk may be caused as by of scattering of the projected light. For example, scattering can be caused by a tooth and/or other oral contents. For example, some light striking a translucent object may be reflected at the surface and some of the light may enter the material and be reflected from a location under this surface. The reflected light may appear as a smeared signal of mixed light from different locations. This first type of crosstalk, which can be referred to as "spatial crosstalk", may vary spatially, and be affected, for example, by one or more of: the scattering coefficients of the tissue and/or other oral content, the scanner optics modulation transfer function limitations, unwanted movement of the scanner and/or other factors.

In some cases optical crosstalk includes spectral crosstalk. For example, spectral crosstalk may be affected by one or more of: the light source spectrum, pattern transparency and/or the imager's spectral filters, and/or other factors. In some embodiments, spectral crosstalk may occur when light in one waveband is detected by a sensor measuring a different waveband. For example, spectral crosstalk may be constant. In some embodiments known, constant crosstalk is taken into consideration before and/or during processing of the imaged pattern.

In some embodiments, spatial crosstalk is reduced or eliminated by applying algorithms designed to remove the crosstalk. In some embodiments, the spectral crosstalk, which, in some cases, is of known and constant properties, is reduced or eliminated by applying image preprocessing with pre-calibrated coefficients and/or by using one spectral imager at detection. For the sake of the current disclosure, a spectral imager configured to detect and differentiate between at least two spectral bands. For example, a spectral imager may include filtered camera filtered camera (for example a conventional color imager including for pixel filters) and/or a hyperspectral imager. For example, a hyperspectral imager may include a whiskbroom scanner, a push broom scanner, an integral field spectrograph (and/or a device employing related dimensional reformatting techniques), a wedge imaging spectrometer, a Fourier transform imaging spectrometer, a computed tomography imaging spectrometer (CTIS), an image replicating imaging spectrometer (IRIS), a coded aperture snapshot spectral imager (CASSI), and/or image mapping spectrometer (IMS).

In some embodiments in which spatial crosstalk is significant, such as in the case of imaging teeth using structured light, the spatial crosstalk causes smearing of the structured light pattern. For example, spatial crosstalk may make it difficult to reconstruct the pattern and/or make it difficult to associate the image of the pattern with the projected pattern. In some embodiments, the reconstructed pattern is used to produce a depth map. In some cases, a pattern having higher density of entities is used to reach a higher resolution and/or higher accuracy of the measured depth. Smearing, for example, due to spatial crosstalk, may in some instance make it difficult to reconstruct the pattern, reduce the resolution of highly dense patterns. For example, spatial crosstalk may reduce the resolution and/or accuracy of measurements.

In some cases, in which smear or spatial crosstalk is significant, for example when pattern is illuminated on a translucent material such as a tooth, the projected stripes may spatially mix together. In case of spectral crosstalk, stripes of different wavelengths may excite the same detector. For example, the combination of spatial crosstalk and spatial crosstalk may cause projected stripes at different locations and/or wavelengths "mix." For example, lines projected at different locations and/or wavelengths may mix through the translucent teeth and/or be received together by the same sensor, making it difficult to reconstruct the color of the stripes and/or the location of the edge between the stripes.

In some embodiments, spectral differentiation may be used to reduce spatial crosstalk. For example, adjacent and/or nearby projected entities may have different spectral signatures. Light mixed between two entities may be removed by spectral methods. For example, spectral differentiation may produce combined spectral and/or spatial data in the form of a color image and/or multiple narrow band images and/or hyperspectral data cube. The resulting data is used, for example, to determine the position of each projected entity with reduced crosstalk from other entities.

In some embodiments, multi spectral imaging may be used. For example an image may be acquired with a conventional Bayer filter based color camera and/or a narrow band imager based on three, four, or five color differentiation (e.g. narrow band Red, Blue, Green (RGB) filters and/or an infrared (IR) filter and/or an ultraviolet (IR) filter In some embodiments, hyperspectral imaging may be used to reduce spectral crosstalk that may occur when an image is acquired with a multispectral imager. In some embodiments, hyperspectral imaging may break the spectrum into more than 4 and/or more than 5 and/or more than 8 and/or more than 20 different bands. Alternatively or additionally, hyperspectral imaging may break the spectrum into narrow bands. For example, narrow bands may have reduced overlap over Bayer Filter RGB imaging. For example, a convention magenta filter may allow unintended green light to leak into an image. Hyperspectral filters may include orthogonal colors and/or reduce spectral crosstalk. Optionally, a hyperspectral imager may include a camera with an interference filter. For example, there may be an interference filter on each pixel.

In some embodiments, a hyperspectral imager may be used to detect a signal. Optionally, a hyperspectral camera comprises one or more narrowband filters. Optionally, a color pattern comprising a plurality of narrowband colors is projected, and a hyperspectral camera comprising matching narrowband filters is used for acquiring the image. A potential advantage of separation between the color channels may include facilitating reconstruction of the color and/or location of each stripe. In some embodiments, the hyperspectral camera measures the intensity of each color channel at each hyperspectral pixel, and identifies the strongest color channel as the correct color, neglecting the contribution of color channels having lower intensities at the pixel. A potential advantage of using a hyperspectral camera may include facilitating estimating the colors of the projected color pattern, for example in cases in which the color is altered by spectral reflectance properties of the object, smear, spatial crosstalk, etc. Factors affecting the received color may include material type, color of the object, specular reflections, diffuse reflection, bulk scattering and absorption, translucency, local pigmentation, stain, ambient illumination, light incidence angle and/or other factors.

An aspect of some embodiments relates to using at least one narrowband filter for detection of a pattern projected onto an intra-oral scene. In some embodiments, an intra-oral scene is illuminated using a plurality of wavelengths (or a plurality of different narrow bands of wavelengths), and a plurality of narrowband filters are used for selectively receiving the plurality of wavelengths (or narrow bands) at detection.

In some cases non-uniform reflection of light, for example light returning from translucent tooth bulk portions (e.g. other than an external surface onto which the light was projected) results in smearing of adjacent pattern stripes. This smearing may lead to crosstalk between the differently colored stripes, making color reconstruction more difficult. Misidentification of color may lead to errors in identifying a relative spatial location in the pattern, which may further result in errors in constructing the 3D model. In some embodiments, by using a narrowband detector, the effect of inherent smearing and/or spatial crosstalk of the projected light by the different structures and/or materials in the intra-oral scene may be mitigated. Optionally the narrowband detector is designed to capture selected wavelengths of light and/or to reduce spectral crosstalk. Optionally reducing since spectral crosstalk may increase the system's sustainability and/or reduce processing errors. For example, a potential advantage of using a narrowband illumination coding and detectors may include increasing the system's sustainability, and/or reducing processing errors, and/or reduce crosstalk (e.g. including spectral and/or spatial crosstalk).

In some embodiments, one or more interference filters are used for detecting the pattern. Additionally or alternatively, one or more dichroic filters are used for detecting the pattern. In some embodiments, liquid crystal based filters may be used.

In some embodiments, spectral crosstalk is reduced at detection such that in any pixel of a first imaged pattern entity comprising a first wavelength (or narrow band of wavelengths) there is less than 1% less than 5% less than 10%, less than 20%, less than 30% contribution of a second wavelength (or narrow band of wavelengths) of an adjacent pattern entity. Reducing crosstalk may, in some embodiments, reduce risk of misidentifying a color, for example, pattern entity's color. For example reducing crosstalk may reduce the probability of mistakenly identifying an observed color as one of the other colors in a pattern. In some embodiments, the number and/or order of colors in a pattern is selected for reducing ambiguity. For example increasing the number of different colors in a pattern and/or decreasing the distance between different colored projections may increase the precision of determining a position of an illuminated object. Alternatively or additionally, the number of colors in a pattern may be reduced and/or the distance between differently colored locations may be increased and/or the order adjusted to reduce the risk misidentification of a color and/or mistaking one color for another color that exists in the pattern. Optionally, the number of colors, the order of colors and/or the width of bands may be adjusted according to the required depth range, the required precision, the baseline distance between the pattern projector and imager, and/or the pattern density. For example, misidentification of a color may occur as a result of spectral crosstalk. Misidentification may increase as the spectral overlap between the different spectral bands increases. For example, spectral overlap may depend on the spectral range and/or the spectral width of the different pattern colors.

In some cases, spectral misidentification may increase due to spatial overlap and/or smearing between different colored projections. For example black areas between the different colored projected entities may be utilized for differentiation of the entities. Optionally the black areas may facilitate reconstruction of a size (e.g. width for a color band) of the entities. Optionally the geometry of black areas separating entities is selected, to provide maximal coverage of the scene by the pattern entities (e.g. smaller black spaces and/or increased density of entities), and/or to facilitate crosstalk correction (for example reducing the density of entities and/or increasing the area of black spaces separating between entities).

In some embodiments, the different wavelengths are detected by different pixels of the imager (such as in a hyperspectral camera, e.g. IMEC SM4X4-470-630 CMOS), for example by covering the different pixels with interference filters that match the projected wavelengths.

In some embodiments, the different wavelengths are detected sequentially. Optionally, the different wavelengths are projected and/or detected sequentially. Optionally, a tunable filter is used for detecting the wavelengths sequentially.

An aspect of some embodiments relates to incorporating an asymmetric and/or non-circular aperture in a light projector used for illuminating the oral cavity.

In imaging systems an aperture typically affects an optic rays cone angle and/or brightness or an image. The optic rays cone angle typically determines the Depth Of Field (DOF). A narrower optic rays cone angle corresponds to a higher F-number (F#), and a larger DOF, and vice versa. In some embodiments, a non-circular aperture is optionally used in a light projector.

In some embodiments the non-circular aperture is optionally an elliptic aperture, having a major axis and a minor axis. The minor axis is associated with a narrower optic rays cone angle, a lower effective F-number, a lower DOF, and, being smaller, acts to let less light through. The major axis is associated with a wider optic rays cone angle, a lower effective F-number, a lower DOF, and, being larger, acts to let more light through.

In some embodiments, the projector projects a pattern of stripes.

In some embodiments the pattern of stripes is aligned so that a direction along the stripes is parallel to a direction of the major axis. As mentioned above, the direction of the major axis is associated with a lower effective F-number and a lower DOF, however, even if the pattern of the stripes is defocused, or smeared, along the direction of the stripes, this does not make a significant difference in the pattern, since the stripes are optionally uniform along their length, so the smearing does not affect the pattern. In such a case, the direction of the minor axis is associated with a higher effective F-number and a larger DOF, which is desirable in the direction across the stripes. A synergistic effect is that the pattern being projected benefits from the higher effective F-number and a larger DOF associated with the minor axis in the direction which benefits from image focus, and benefits from receiving more light, thereby a brighter image, than would be associated with a circular aperture having a diameter equal to the minor axis.

In some embodiments, the pattern comprises a plurality of wavelengths or narrow wavelength bands (e.g. at least 5, at least 7, at least 15 or intermediate, higher or lower number). Optionally, the wavelengths are selected from a narrow spectral band. In some embodiments, projection of the narrow wavelength bands is implemented using interference filters applied to each pixel. In some embodiments, the wavelength range is selected according to available projection and imager technology (e.g. a range may be selected to fit a sensor for example 400-850 nm may fit a Si CMOS sensitivity). Alternatively or additionally, the range may be chosen according to properties of illuminated object (for example 400-700 nm may fit the visible range and/or provides higher contrast over the teeth). In some embodiments, the wavelength range is selected to increase contrast with the scanned teeth, for example a wavelength range selected from the shorter visible wavelength range (for example between 400-500 nm, 380-450 nm, and or 470-550 nm or intermediate, larger or smaller ranges). Additionally or alternatively, shorter wavelengths may be used, for example wavelengths of the ultraviolet range (e.g. shorter than 400 nm) are used.

A potential advantage of a pattern comprising a plurality of short wavelengths (or wavelength bands) selected from a relatively narrow spectral band may include lowering smearing of the intraoral features, improving color detection owing to the reduced crosstalk between wavelength channels. Another potential advantage may include reduced sensitivity for ambient light, contributing to a more accurate color identification. Accurate color identification may be effective to reduce ambiguities, which can cause errors in pattern restoration and/or errors in detection of depth variations in the scene.

Optionally, if the pattern comprises longer wavelengths (including for example non-blue colors for which there may be lower contrast and/or larger smear over the tooth), the pattern entities (e.g. stripes) are selected to be wider than those that would be used for the shorter wavelengths (purple-blue color range).

Various projection configurations and/or methods may be implemented for projecting the wavelength-coded pattern. For example, in some embodiments, a plurality of light sources (such as a plurality of LEDS or lasers) each configured for emitting light at a selected wavelength are arranged adjacent each other. Additionally or alternatively, a set of filters suitable for transmitting the selected wavelengths is attached to a light source (e.g. LED) for projecting the pattern onto the scene. Additionally or alternatively, a set of filters suitable for transmitting the selected wavelengths is attached to a transparent substance illuminated by a light source having a wider spectrum. Additionally or alternatively, a grating that diffracts light from a light source having a wider spectrum is used. Additionally or alternatively, a variable wavelength source such as a variable wavelength laser is used with a scanning mirror (e.g. MEMS mirror). Additionally or alternatively, a variable wavelength filter such as a variable interference filter is used for altering the transmitted wavelengths. Additionally or alternatively, the transmitted wavelength is changed in accordance with the varying wavelengths that are received in the sensor. Additionally or alternatively, the transmitted wavelength is modified according to the rolling movement of the sensor shutter, in a way that the camera detects different wavelengths in different areas of the scene as the shutter is moved over the scene.

An aspect of some embodiments relates to reducing crosstalk between imaged pattern entities by utilizing one or more separating regions in the pattern. In some embodiments, the separating regions comprise non-illuminated regions, defining dark regions between the pattern entities. In some embodiments, the dark regions enable separation of the pattern entities following scattering and/or smearing.

In some embodiments, a referential color pattern is projected onto the intra-oral scene. In some embodiments, the referential color pattern comprises colored entities and separation regions between entities of different colors. In an example, a referential color pattern comprises an arrangement of black and colored stripes arranged such that a black stripe separates between two colored stripes. Alternatively to a non-illuminated area, the separating region comprises a color which is not transmitted by a filter used at detection. Alternatively, frames with uniform lighting are acquired between frames with patterned lighting for extraction of color reflection properties of the scene. Additionally or alternatively, frames with uniform lighting are used for obtaining 3D information regarding matching features in the scene.

In some embodiments, the dark regions are large enough to avoid a geometrical overlap between imaged pattern entities. For example, in a pattern comprising dark regions in the form of stripes, the dark stripes are selected to be wide enough so as to ensure that for imaged pixels of at least a portion of the dark stripe (e.g. a vertical center thereof) a contribution of light from the colored entities is substantially nonexistent. Alternatively, a contribution of light from the colored entities exists, but other features (e.g. anchors) allow for identifying the dark region as such.

In some embodiments, detection of the referential pattern comprises subtracting the imaged color obtained in the black stripes situated at opposing sides of the colored stripe from the colored stripe, to reconstruct the colored stripe. Potential advantages of using the referential pattern may include reducing or preventing spectral crosstalk between the different stripes which may occur when the pattern light is scattered through the teeth, tissues and/or other oral contents. Scattering and/or smearing of the pattern entities may occur as a result of the different types of materials and/or structures in the intra-oral scene, for example teeth, fluids (e.g. saliva, blood), gum, artificial prostheses, treatment and/or food residuals, natural defects (e.g. cavities) and/or other. Smearing of the image can result also from the limited depth of field (DOF) of the projector and the camera optics, scanner movement during the image and/or projector exposure time and also from the object local plane slope. The smearing may be increased when the imaged surface is at a high angle to the sensor and/or when the focus of the sensor is reduced, for example due to parts of the surface being out of the preferred focus range of a sensor. For example, black areas may be increased to counteract increased smearing.

In some embodiments, one or more image processing algorithms such as spatial filtering, adaptive histogram equalization, local thresholding, non-maximum suppression, and/or other algorithms are applied to an imaged pattern that comprises dark regions for enhancement of the stripe's contrast, color, assessment of ridge location and/or other characteristics.

Use of dark separation regions may be especially advantageous when processing areas in which a distance between the stripes decreases, for example in areas exhibiting steep angles towards the imager.

An aspect of some embodiments relates to incorporation of one or more anchors in a pattern projected onto an intra-oral scene, by introducing irregularities in a structured light pattern. In some embodiments, the pattern comprises a monochromatic uniformly recurrent arrangement of stripes. In some embodiments, irregularities are introduced into the pattern instead of or in addition to multi-color information.

In some embodiments, the anchors are spread in the field of view to facilitate restoring the pattern from the acquired image. In some embodiments, restoring comprises indexing the imaged stripes of the pattern, by tracing each imaged stripe back to its matching counterpart in the known projected pattern. In some embodiments, the anchors are indexed directly, while the stripes are indexed according to their spatial location relative to the anchors. In particular, a structure of the stripe may be used for statistical analysis of relative location of the various points forming the stripe to the anchors. A potential advantage of using a structure of the stripe for analyzing location may include high sustainability to indexing errors caused by errors in evaluating a distance to the anchors, caused by stripe loss in the imaged scene. Stripe loss may be caused by the scene geometry, shadows in the scene, tooth defects, operator movement and/or other factors or combinations thereof.

In some embodiments, the amount of anchors incorporated in a pattern is selected in accordance with the scene variability, for example, if the scene comprises a relatively small amount of smooth patches (a smooth patch being defined as a region having no depth discontinuities), a reduced amount of anchors (e.g. as compared to a scene with a higher number of smooth patches) can be used. For example, a recurrent stripe pattern can be used, with an anchor spread selected to ensure that at least one anchor is situated upon a smooth patch. Once that anchor is indexed, the stripe portions situated within the same smooth patch allow for expanding of the indexing to additional detected points of the pattern.

In some embodiments, the anchors are in the form of diagonals intersecting the stripes, forming a plurality of junctions (between the stripes and the diagonal) that can be used as anchors. In some embodiments, anchors are provided in the form of two or more color zones. Other examples of anchors may include variations between the stripes, such as variations in width, spacing, shape, angle, color and/or other variations or combinations thereof. Other variations may include in-stripe variations, for example a stripe width that changes along the stripe, missing portions along the stripe, and/or other in-stripe variations. In some embodiments, anchors (e.g. in the form of stripe variations) are located, for each stripe, at a different horizontal position relative to variations of one or more adjacent stripes, to facilitate identifying the stripes.

An aspect of some embodiments relates to scanning an intra-oral scene using unstructured lighting and patterned lighting. Optionally, the unstructured lighting comprises uniform lighting.

Additionally or alternatively, the unstructured lighting comprises lighting in which no predefined pattern is projected.

In some embodiments, information obtained by imaging the scene using unstructured lighting facilitates restoring the pattern from an image obtained under patterned lighting, or vice versa. Some embodiments comprise interchanging between an unstructured lighting frame and a patterned frame. In some embodiments, information obtained by imaging the scene using unstructured lighting facilitates restoring the pattern from an image obtained under patterned lighting. For example, an image obtained under unstructured lighting can be used for collecting and/or completing information about the intra oral scene, for classifying the imaged content.

Another possible usage of unstructured lighting is detecting cues of, depth discontinuities in the scene, which define the borders of the smooth patches. In another example, the image obtained under unstructured lighting is used for natural coloring of the scene. In another example, the image obtained under unstructured lighting is used for evaluating reflection characteristics of the different materials and/or structures in the scene. In some embodiment, the unstructured lighting is white. Alternatively or additionally, reflection characteristics of the different materials and/or structures in the scene are evaluated at the different spectral regions and/or multiple spectral regions, for example RGB.

In some embodiments, areas in the scene that are prone to projected stripes loss are detected. Optionally, signal-to-noise evaluation methods are applied to the unstructured light image and/or patterned image to mask these areas. In some embodiments, contrast enhancement techniques are applied upon the combination of patterned and unstructured light images.

In some embodiments, the transmission power (of either structured and/or unstructured light) is modified during scanning. In an example, the power is adjusted after one or more images are acquired and it can be estimated whether higher or lower power is needed. Optionally, the estimation is performed according to the signal to noise ratio and/or according to the saturation level of the received color.

In some embodiments, pre-defined power levels are used; additionally or alternatively, the power levels are dynamically adjusted during scanning, e.g. based on the acquired images. Optionally, power levels are set in accordance with the wavelength ranges used and/or selected per different areas in the field of view.

It is noted that a "wavelength" as referred to herein may include a single wavelength or a range of wavelengths, such as a narrow band of wavelengths. A "color" as referred to herein may contain a single wavelength, a narrow band of wavelengths or a mixture of wavelengths.

An aspect of some embodiments of the current disclosure relates to measurement of the optical properties of intraoral features. For example, measured properties may include color, shade, scattering, and/or absorption. For example, intraoral features may include a tooth, an inlay, a crown, a gum, a tongue, a carie and/or another intraoral feature. For example, properties that affect the aesthetic appearance of a restored feature and/or a dental prosthesis may be measured. Optionally a pattern of multicolor light is projected on an object and/or light reflect and/or scattered and/or absorbed and/or produced by the feature are measured.

In some embodiments, corrections may be made for example for ambient light, geometrical effects and/or optical effects. Corrections may be made to detected color and/or geometry. A processor is optionally supplied to compute corrections and/or model a feature to derive properties of the feature based on the measured optical properties. Optionally a processor may use set algorithms, known correlations and/or artificial intelligence to recognize features and/or properties.

An aspect of some embodiments of the current disclosure relates to automated generation of objects for dental restoration. For examples, objects for dental restoration may include a filling, an inlay, a crown, a prosthetic and/or an implant. For example, optical properties may be measure, corrected and/or modeled. The measurement and/or modeling results are optionally used to choose materials for the restoration. Optionally the restoration may be spatially heterogeneous. For example, a restoration may have optical properties that change along a surface and/or with depth. In some embodiments, a material for the restoration is chosen according to known optical properties of the material. Optionally the restoration is made automatically for example using additive production.

An aspect of some embodiments of the current disclosure relates to diagnosis of dental conditions based on optical properties. In some embodiments measured optical properties and/or measure geometry are correlated to known conditions. Alternatively or additionally, a model of an intra-oral feature is produced from an intra-oral scan. Optionally, the model is analyzed (for example using automatic algorithms and/or artificial intelligence), to determine the presence of pathologies.

An aspect of some embodiments of the current disclosure relates to identification of dental features based on optical properties.

An aspect of some embodiments of the current disclosure relates to a pattern projector for an IOS. In some embodiments a pattern projector will be designed for increased efficiency by decreasing lighting sources directed toward a dark area of a pattern. For example, along with and/or instead of blocking light directed at a dark portion of a pattern, light sources directed to that part of the pattern may be turned off and/or spaces may be defined to which light emitters are not directed. For example, a projector may have an emitter array including emitters and spaces that are free of emitters. Alternatively or additionally, an emitter array may be configured for controlled activation of a portion of the emitters. For example, some emitters directed toward an illuminated region of the pattern may be active while emitters directed at a non-illuminated region may remain inactivated. For example, the array may include LED's, quantum dots, nano-particles, AMOLED's and/or VCSEL's. Optionally the emitters are mounted on a non-emitting substrate.

An aspect of some embodiments of the current disclosure relates to an IOS having a stand-off that defines and/or measures a distance and/or direction to an imaged object. For example, an IOS may include a physical standoff (for example an elongated object such as dental probe) that touches an imaged object at a defined distance. Optionally the probe may have a directed surface that is matched to the surface of the object. For example, the directed surface may be placed against a surface being measured and/or define an angular relation between the IOS and the surface. Alternatively or additionally, an IOS may have a sensor that detects when a desired distance and/or angle is reached. For example, the IOS may inform the user and/or automatically take an image when desired position is reached.

Figure 1:
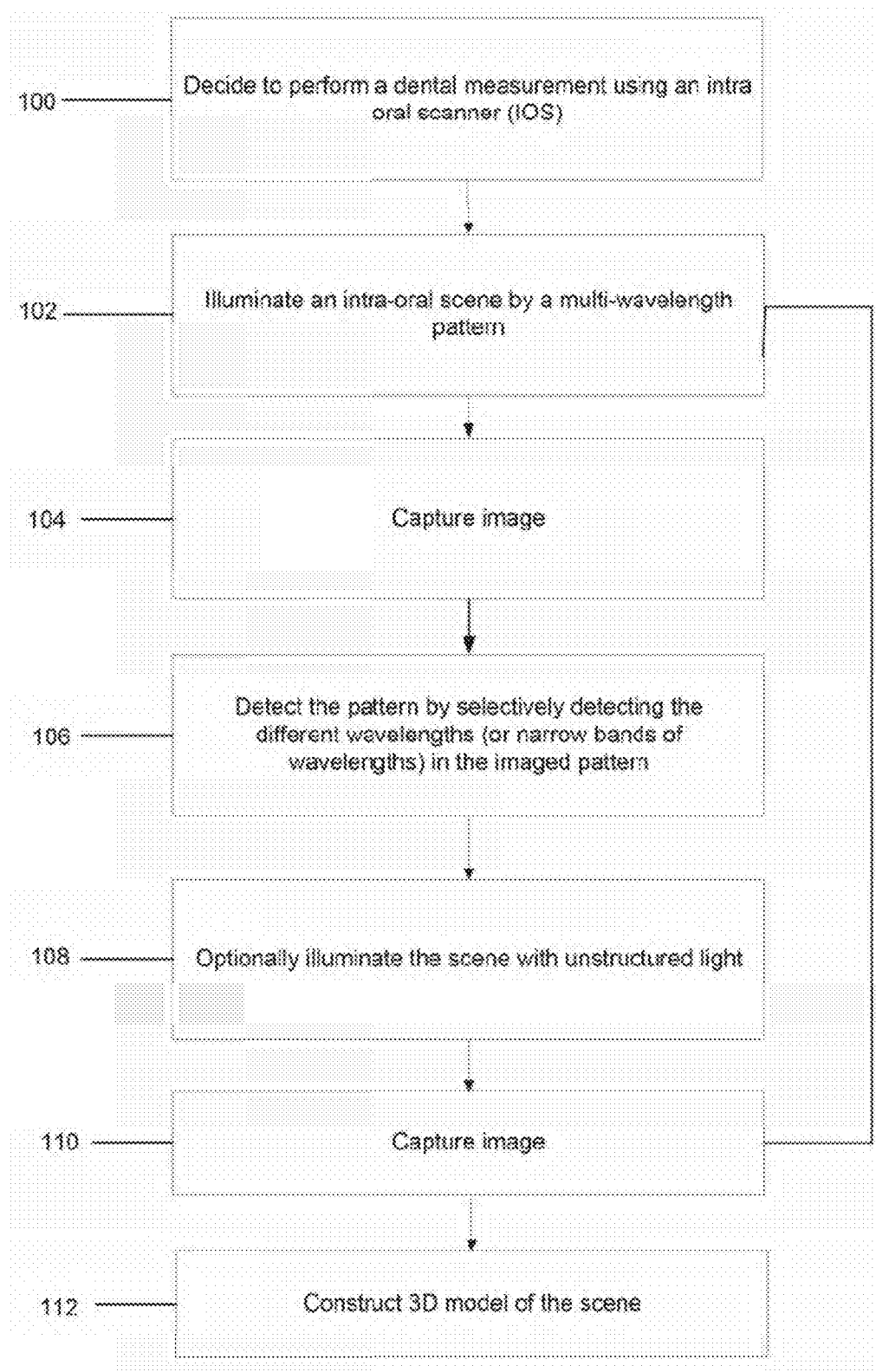
FIG. 1 is a flowchart of a method for scanning an intra-oral scene by projecting a multi-wavelength pattern and separating the different wavelengths upon detection of the pattern, according to some embodiments of the disclosure.

Referring now to the drawings, FIG. 1 is a flowchart of a method for scanning an intra-oral scene by projecting a multi-wavelength pattern and separating the different wavelengths upon detection of the pattern, according to some embodiments of the disclosure.

In some embodiments, a dentist and/or other clinical personnel decide to perform a dental measurement using an intra oral scanner (IOS) 100. In some embodiments, measurement is performed for further construction of a dental prosthetic such as a crown, bridge and/or other dental structures. In some embodiments, a 3D measurement of a portion of a tooth, a full tooth, a plurality of teeth and/or partial or full dental arch is acquired. Optionally, for example for construction of a prosthetic that extends below the gum stripe, measurement below the gum stripe is carried out. In some embodiments, a measurement of a non-visible area such as a subgingival area is obtained.

In some embodiments, the intra-oral scene is illuminated by a multi-wavelength pattern 102. In some embodiments, the pattern comprises a recurrent arrangement of entities, for example a recurrent sequence of stripes. In some embodiments, one or more stripes of the pattern are each comprised of a narrow band of wavelengths. Optionally, the FWHM of such narrow band is 1 nm, 5 nm, 10 nm or intermediate, longer or shorter widths. In some embodiments, one or more stripes of the pattern are absent of light, defining black regions in the pattern.

In some embodiments, the projected pattern comprises at least 2 wavelengths, at least at least 5 wavelengths, at least 7 wavelengths, at least 10 wavelengths, at least 20 wavelengths or intermediate, larger or smaller number.

In some embodiments, an image of the illuminated scene is captured 104 using a light collector such as a camera and/or imager of the IOS.

In some embodiments, the imager is configured for selectively detecting the plurality of wavelengths in the pattern 106. In some embodiments, the imager comprises a filter suitable for transferring wavelengths of interest. In some embodiments, the wavelengths transferred by the filter are selected in accordance with the different wavelengths of the projected pattern and/or selected in accordance with the imaged area. In some embodiments, the filter is configured to transfer two or more wavelengths that are selected in accordance with their relative spatial location on the pattern, for example configured to transfer at least one wavelength from an upper region of the pattern and at least one wavelength from a lower region of the pattern.

In some embodiments, the received signals are filtered by an interference filter, a dichroic filter, a liquid crystal filter and/or other filter designed for transmitting selected wavelengths of the pattern and blocking others.

In some embodiments, only a single pattern is projected throughout the scanning process. Optionally, only power settings and/or filter settings (of a transmitting and/or receiving filter) are modified throughout the scanning process, while the pattern remains constant. A straightforward advantage of using a single pattern may include reducing processing errors which may occur as a result of movement of the system in between subsequent frames. Another potential advantage of projecting and detecting a single pattern may include simplifying use. Another potential advantage may include providing for an IOS having a relatively small form factor due to a simple projector structure, for example as compared to an IOS that projects multiple patterns. A small form factor scanner for example as described herein may be especially advantageous for accessing hard to reach areas in the mouth, for example for obtaining a measurement of a tooth close to or at the gum stripe, where a steep angle between the tooth wall and the scanner may be present.

Alternatively, a plurality of patterns such as 2, 3, 5, 7 or intermediate or larger number of patterns is projected.

Optionally, the intra-oral scene is illuminated with unstructured lighting 108, e.g. uniform lighting, and the unstructured light image is then captured 110. In some embodiments, the scene is illuminated by an interchanging sequence of unstructured lighting and patterned lighting and/or any other sequence of unstructured lighting and pattern lighting (for example, 1 frame of unstructured lighting followed by 2 frames of patterned lighting, 1 frame of unstructured lighting followed by 3 frames of patterned lighting, 2 frames of unstructured lighting followed by 1 frame of patterned lighting and/or other combinations). Optionally, information gathered from the unstructured light image is used for constructing the 3D model of the scene. Optionally, information gathered from the unstructured light image provides cues for restoring a pattern, for example indications of areas prone to stripe loss.

In some embodiments, a 3D model of the scene is constructed 112. In some embodiments, the model is constructed by restoring the projected pattern. In some embodiments, restoring includes a calculation based on a shift of the projected pattern entities when striking surfaces of the scene, the shift being parallel to the baseline connecting the centers of the projector and the optical aperture of the camera.

Pattern distortion may be affected by one or more of the varying surface shape of the scene, the plurality of structures in the scene (e.g. teeth, gum, prosthetics), the plurality of materials in the scene and their different reflective properties (e.g. dentin, enamel, artificial fillings, soft tissue, saliva), and/or other factors.

In some cases, the projected pattern entities are smeared, for example by the contents of the intra oral scene such as teeth, gums and/or other tissue. Smearing may induce optical crosstalk between the imaged pattern entities.

In some embodiments, selective detection of the different wavelengths in the pattern is effective to reduce the spatial crosstalk. Optionally, filtering is performed to reduce crosstalk.

In some embodiments, as mentioned hereinabove, information from one or more images of the scene obtained under unstructured lighting (e.g. uniform lighting) is used for constructing the 3D model. Optionally, information from unstructured light images is used for reconstructing the imaged pattern. In some embodiments, the unstructured light image is used for natural coloring of the model. Additionally or alternatively, reflection properties of objects in the scene and/or reflection properties at different locations in the scene are exploited from the unstructured light image. Additionally or alternatively, geometry cues of the scene (e.g. depth information, such as locations of depth discontinuities) are extracted from the unstructured light image. In some embodiments, pixel by pixel analysis, global analysis, and/or other processing methods are applied to the unstructured light image to extract the information. In some embodiments, information obtained from the unstructured light image is used for removing local spectral reflectance effect and/or local color of the target.

In some embodiments, unstructured lighting and patterned lighting are projected simultaneously, for example via two channels. A potential advantage of projecting both light schemes simultaneously may include reducing effects of scanner movement, such as due to user hand movement, on the acquired images.

Figure 2:
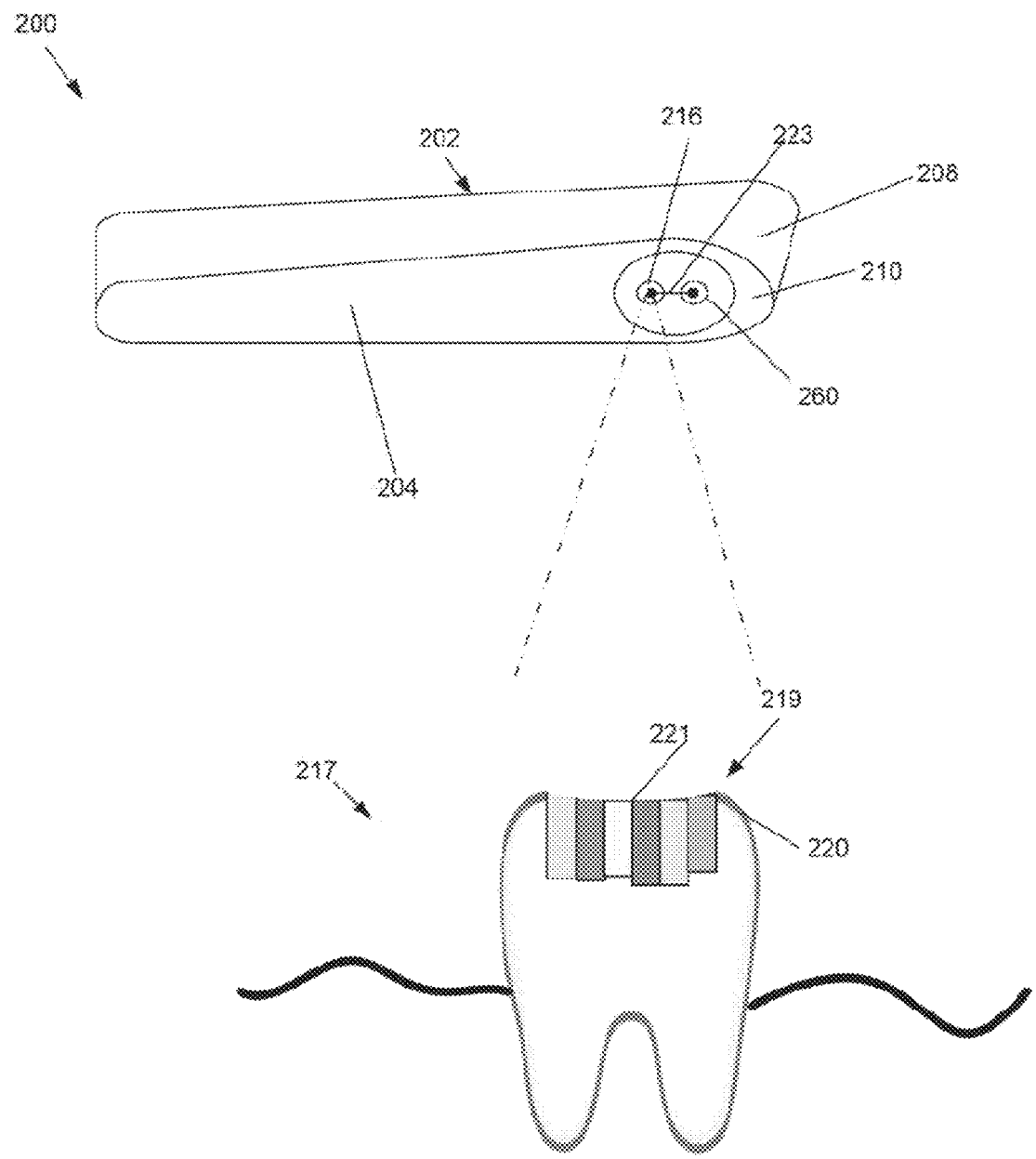
FIG. 2 is a schematic illustration of a 3D intra-oral scanner system, according to some embodiments of the disclosure.

FIG. 2 is a schematic illustration of a 3D intra-oral scanner system, according to some embodiments of the disclosure.

In some embodiments, IOS system 200 comprises an IOS 202, shaped and/or sized for insertion into the mouth for scanning an intra-oral scene 217.

In some embodiments, IOS 202 includes a hand piece 204 and a head portion 208. In some embodiments, an oral-facing surface 210 of head portion 208 includes a light emitter, pattern projector 216, and an optical aperture of a camera or imager 260.

In some embodiments pattern projector 216 may include any suitable light source, such as a light-emitting diode (LED), a laser, such as edge emitter or VCSEL etc. Pattern projector 216 optionally includes beam shaping optics, such as a lens, for example to use the light source light efficiently. In some embodiments, optical fibers with a remote light source may be used.

In some embodiments, pattern projector 216 and/or a different light projector is configured for projecting a pattern 219 onto the chosen surface, for example onto a surface of tooth 220. In some embodiments, pattern 219 comprises an arrangement of recurrent parallel stripes 221. In some embodiments, each stripe 221 is composed of a different wavelength or wavelength range. Optionally, the pattern is composed of a total of 3 wavelengths, 5 wavelengths, 7 wavelengths, 10 wavelengths, 20 wavelengths or intermediate, larger or smaller number of wavelengths or narrow wavelength bands. In some embodiments, pattern projector 216 comprises a plurality of interchanging sub-sources, for example a light source suitable for projecting patterned lighting and a light source suitable for projecting uniform lighting.

In some embodiments, wavelengths of the pattern are selected from the visible wavelength range. Optionally, the wavelengths are selected from the lower end of the visible range, for example between 400-500 nm, or intermediate, higher or lower ranges (for example between 400-500 nm, between 380-420 nm, between 460-550 nm, between 350-450 nm). A potential advantage of selecting wavelengths from the lower end of the visible range may include maximizing contrast when scanning teeth, for example as mentioned herein above. Also, wavelengths of the lower end of the visible range may be easily observed on the gingiva. Additionally or alternatively, the pattern includes a combination of wavelengths from the visible range and other regions of the electromagnetic spectrum, e.g. wavelengths of the IR range and/or UV range.

In some embodiments, stripes 221 are generally perpendicular to line 223 (further referred to herein as "baseline") which extends between an optical aperture of pattern projector 216 and an optical aperture of the imager 260. Additionally or alternatively, one or more stripes 221 are at an angle to line 223, for example an angle of 5 degrees, 10 degrees, 20 degrees, 30 degrees or intermediate, larger of smaller angles.

In some embodiments, the IOS comprises one or more folding mirrors positioned to redefine the baseline by forming virtual aperture locations.

In some embodiments, imager 260 comprises one or more filters for selectively detecting the different wavelengths of pattern 219. Optionally, the filters are narrowband filters.

In some embodiments, the filters are configured to detect different wavelengths at different areas of the scene.

In some embodiments, filter properties are modified during scanning (e.g. using mechanical and/or electrical means), for example so that the filter transfers a wavelength or a set of wavelengths different from a currently transferred set of wavelengths.

In some embodiments, the different wavelengths are detected by different pixels of the imager, for example by covering the pixels of the imager with interference filters that match the projected wavelengths, for instance as in a hyperspectral camera.

In some embodiments, the plurality of wavelengths is projected and/or detected sequentially over time. Optionally, sequential detection is achieved using a scanning interference filter and/or other tunable filter.

FIG. 3 schematically illustrates interaction between projected light and objects in the intra-oral scene, such as teeth and/or gums.

In some embodiments, tooth 300 is illuminated by an IOS for example as described hereinabove) and/or using other light-projecting modality with a multi-color stripe pattern. In some embodiments, at least some of the projected light photons (indicated by arrow 304) that illuminate a stripe such as stripe 306 are reflected back from the tooth (as indicated by arrow 308) and received by the IOS. Additionally or alternatively, at least some of the projected light photons undergo scattering 312 by the tooth and are at least partially absorbed in the tooth and/or are travel a certain depth into the tissue and/or are reflected from tooth portions different from the tooth portion onto which the stripe was projected. For example, light photons (indicated by arrow 316) may be returned from a location of an adjacent stripe 314, where they may interfere with back-reflected photons of stripe 314 which is colored differently than stripe 306, thus reducing the probability of correctly identifying the color of stripe 314. Additionally or alternatively, light photons (indicated by arrow 320) return from an in-between stripe location. Optionally, these scattered light photons returning from a non-illuminated, in-between stripe location are used during detection as a reference for correctly identifying the color of stripe 314.

In some embodiments, the color of the non-illuminated regions (e.g. a non-illuminated region alongside a colored stripe) is used during image processing for determining the projected color of the stripe. An exemplary method for determining the stripe color comprises subtracting the color received at the non-illuminated regions from the colored stripe. A potentially more accurate example is subtraction of weighted average of the not illuminated region, wherein weights are set, for instance, according to the distance from illuminated regions. Optionally, processing is performed for each color channel separately (e.g. for each of the RGB channels). Another exemplary method comprises estimating a scattering factor of the local material (e.g. tooth or gums) and removing the scattering accordingly, for instance using linear relation coefficients that depend on the scattering factor of the material. Optionally, the contribution of ambient illumination is taken into consideration as well. Another exemplary method comprises using a local spatial filter to subtract background color obtained using the non-illuminated regions.

In some embodiments, the intensity of light returned from different locations of tooth 300 may decrease as the distance between the location from which the light is returned and the point of incidence of the projected light with the tooth increases. Another factor which may affect the intensity of the returning light may include the reflection coefficient of a material and/or composition of materials from which the light is returned. The factor by which the intensity is reduced may depend on material composition, surface and/or volume features of the tooth. In some embodiments, one or more materials in the scene are identified according to their reflection factor.

In some embodiments, an estimated scattering coefficient and/or reflection coefficient is used for improving the accuracy of 3D model. Optionally, improved accuracy may be achieved by compensating the translucency induced patterns shift in the image.

FIG. 4A is an example of a multi-wavelength pattern for projecting onto an intra oral scene, according to some embodiments, and FIG. 4B schematically illustrates a spectral graph of an exemplary pixel of the image, according to some embodiments.

In some embodiments, pattern 400 comprises an arrangement of colored stripes 402. In some embodiments, each colored stripe contains a narrowband wavelength range. In some cases, narrowing the spectral bandwidth of pattern entities (especially of adjacent and/or neighboring entities) may reduce spectral crosstalk. In some embodiments, narrowband pattern projection is combined with narrowband pattern detection (e.g. hyperspectral camera. In some embodiments, combination of narrowband projection and detection with low spectral crosstalk between pattern features may further reduce crosstalk and/or improve accuracy of reconstructed projected pattern features colors and/or locations. Reducing crosstalk may facilitate accurate reconstruction from a strongly smeared image (i.e. spatial smear). For example, reducing crosstalk may facilitate more accurate measurement of a projected pattern on translucent teeth and/or crowns. Reducing crosstalk may facilitate accurate reconstruction of spatial patterns smeared by the limited depth of field (e.g. defocus) of short working distance high resolution optical systems and/or by a combination of the above factors.

In some embodiments, the total number of wavelengths in the pattern is, for example, at least 2 wavelengths, at least 5 wavelengths (for example as shown herein), at least 7 wavelengths, at least 16 wavelengths, at least 25 wavelengths or intermediate, larger or smaller number.

In some embodiments, detection of pattern 400 by the IOS comprises filtering the received light, selectively transmitting the predetermined wavelengths of the pattern (e.g. wavelengths 1-5) and reflecting and/or absorbing others. Optionally, a tunable filter is used, enabling adjustment of the selected wavelengths.

In some embodiments, filtering of the received signals at detection of the imaged pattern is effective to reduce spectral crosstalk such that at an exemplary pixel 406 of a stripe of interest (in this example, stripe 408 of wavelength 1) there is no significant contribution of an adjacent stripe (in this example, stripe 410 of wavelength 2) and/or of more distant stripes. For example as shown in FIG. 4B, in the spectra graph of pixel 406, due to the use of interference filters for the different channels, the contribution of wavelength 2 to the amplitude 412 of pixel 406 would be smaller than 20%, 10%, 5% or intermediate, larger or smaller values. In some embodiments, wavelength bands of adjacent entities are selected to include wavelengths that are relatively far apart from each other on the spectral range. Such arrangement may further reduce spectral crosstalk between the entities.

FIGS. 5A-B schematically illustrate transmission of filters used at detection of the pattern, according to some embodiments of the disclosure.

In some embodiments, the IOS imager comprises one or more filters suitable for transmitting selected wavelengths and/or wavelength ranges of interest, for example as commonly used in hyperspectral cameras. FIG. 5A schematically illustrates passing of selected wavelengths, and blockage (e.g. by reflection) of wavelengths that are not of interest. FIG. 5B schematically illustrates transmission efficiency of the filters used at detection, in this example including 5 different narrowband filters configured for transmitting 5 selected wavelengths, for example wavelengths between 400 and 500 nm on the same graph.

In some embodiments, a filter is configured to dynamically transfer a selected wavelength at times that are synced with projection of the specific wavelength.

In some embodiments, different pixels of the imager comprise different filters, for example such that a fraction of the pixels of the imager (e.g. ⅓, ⅕, ⅛ or intermediate, larger or smaller fraction) will receive a specific wavelength out of the plurality of wavelengths. For example, ⅕ of the pixels of the imager are configured to receive a single wavelength out of a total of 5 different wavelengths.

In some embodiments, pixels configured to capture a specific wavelength also capture a small amount of one or more other wavelengths. Optionally, such capturing method provides for producing a high dynamic range (HDR) image.

In some embodiments, a spectral band will be selected due to a property of interaction between the band and an intra oral object. For example, the five bands of FIG. 5B are all in the high frequency violet-blue-green visible spectrum. These bands may be scattered less by teeth as compared to lower frequency bands (for example red and/or yellow bands).

In some embodiments, narrow spectral bands are selected with very small overlap. For example, the spectral bands in FIG. 5B have pass bands of less than 10 nm and/or transition bands of less than 10 nm. Optionally there is very little overlap between bands, for example overlap between bands in FIG. 5B is restricted to the stop band of the color bands. For example the sensitivity of overlapping (spectral cross talk) is at most 1/10 the sensitivity to the pass band of the filter.

In some embodiments, the sensitivity of a sensor is increased by increasing the width of a passband. Optionally the specificity of the sensor may be increased by decreasing the width of the pass band. Optionally cross talk may be decreased by decreasing the overlap of bands, for example by decreasing the combined width of the pass band and the transition band.

FIGS. 6A-F are various configurations for projecting a multi-wavelength pattern onto an intra-oral scene (shown at a side view), according to some embodiments.

In some embodiments, projection of the wavelength coded pattern comprises using a plurality of light sources, each configured to illuminate the scene with one of the wavelengths of the pattern. For example, as shown in FIG. 6A, a plurality of LEDs 600 are arrayed adjacent each other. Optionally, LEDs used for display technologies such as AMOLEDs are used. In some embodiments, independently operable LEDs are arranged in a dense matrix. Optionally, AMOLEDs formed as thin elongated blocks are used.

Figure 6D:
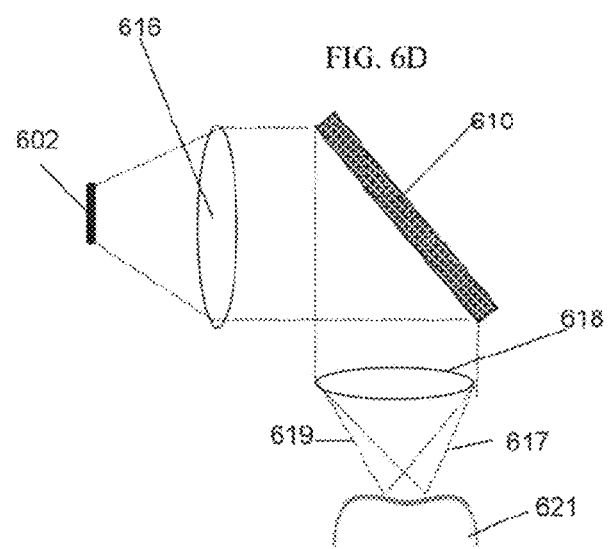
Figure 6C:
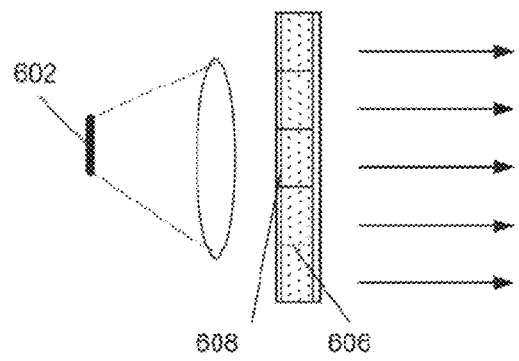
Figure 6E:
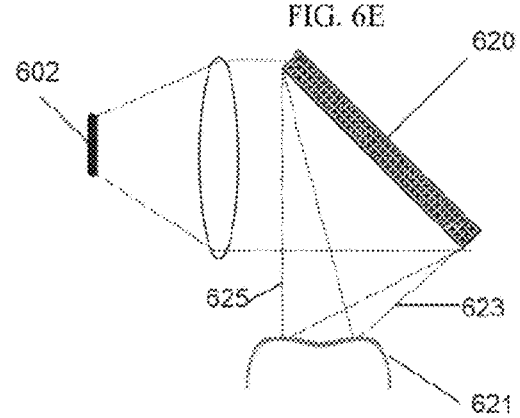
Figure 6F:
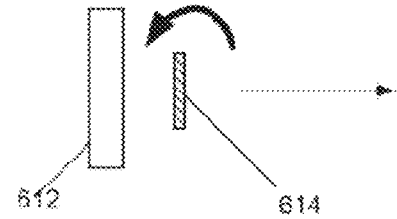
Figure 6B:
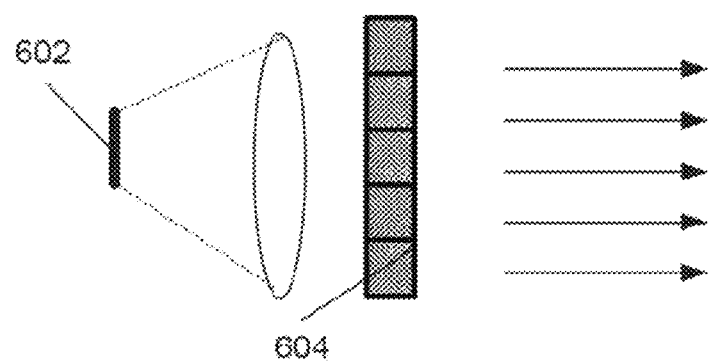

Additionally or alternatively, for example as shown in FIG. 6B, a light source 602 having a wider spectrum is used in conjunction with one or more filters 604. Optionally, for example as shown in FIG. 6C, a set of interference filters 606 attached to a transparent substance 608 is illuminated by light source 602 having a wider spectrum. In some embodiments, said plurality of filters are not adjacent with light absorbing areas in between to produce said black referential areas in the projected pattern. In some embodiments, said light absorbing areas in between are produced by adding a transparent blocking mask (e.g. chrome coated glass) on top of the said filters substrate or by attaching an adjacent mask to a lower resolution color filters pattern. An optional advantage of such embodiments that high resolution chrome masks (e.g. <1 um resolution) can be produced at relative low cost and can provide the needed resolution while the color filters, which are more difficult to be produced with high resolution, can be produced at lower resolution and the combination will still have high resolution.

Additionally or alternatively, for example as shown in FIG. 6D, a grating 610 that diffracts light from a light source 602 having a wider spectrum is used for projecting the pattern. In some embodiments, a first lens 616 is configured to collimate the light projected by light source 602. In some embodiments, a second lens 618 is positioned to direct the different wavelengths such as wavelengths 617 and 619 leaving grating 610 onto the different locations of the intra-oral surface, such as onto a surface of tooth 621.

Additionally or alternatively, for example as shown in FIG. 6E, a diffractive optical element 620 is positioned to diffract the light projected by light source 602 and optionally to direct the different wavelengths such as wavelengths 623 and 625 towards the intra-oral surface, such as onto a surface of tooth 621. Diffractive optical element 620 may be configured to produce the effect of one or more lenses and a grating.

Additionally or alternatively, for example as shown in FIG. 6F, a variable wavelength source 612 is used. For example, a tunable laser is used with a 1D scanning mirror

614 (such as a MEMS mirror). Additionally or alternatively, other optical components suitable for directing or re-directing light are used.

Additionally or alternatively, a wide spectrum light source is used with a scanning mirror (and/or other light re-directing component) to redirect light to a dynamically changing filter. Other color projection configuration may include a glass cover having the different colors, for example in the form of stripes and/or squares. Optionally, colors that highly contrast the tooth are used (such as blue and/or purple). Optionally, the glass cover is attached to a light source such as a LED, along with micro lenses.

In some embodiments a light projector includes a mask. For example, the mask is used to give a geometric form to an illumination entity. Additionally or alternatively, a filter is combined with a monochrome mask (e.g. chrome on glass). For example, a high resolution mask may be combined with a low resolution color filter (e.g. diachronic filter, photographic transparency, low resolution interference pattern) to produce high resolution color entities.

FIG. 7 is a flowchart of a method for scanning an intra-oral scene using a referential color pattern, according to some embodiments.

In some embodiments, a referential color pattern is projected onto the intra-oral scene 700. In some embodiments, the referential color pattern comprises colored entities such as stripes, wherein two colored stripes are separated from each other by a separating region such as a black region. Optionally, the separating region is in the form of a stripe. In some embodiments, the separating region is a non-illuminated region. Such configuration may be advantageous when the number of wavelength bands of the imager is limited and crosstalk between the different bands is significant, for example when an RGB imager with a Bayer filter for sensing the patterned light is used.

Alternatively, the separating region is illuminated with a wavelength substantially different from the wavelengths of interest of the pattern, so that at detection the differently colored separating region can act as reference.

In an example, a first stripe comprises a blue color; a second adjacent stripe comprises a green color; and a separating region between these stripes is black. In another example the separating region between stripes is illuminated with radiation that is easily differentiated from the stripes. For example, a separated region may be illuminated with NIR wavelength radiation. Optionally, the illumination in the dark area may be used to image the "dark area", with little or negligible effect on the detection of an optical entity. For example, dark areas may be imaged in NIR without significant crosstalk affecting stripes in the visible range. Alternatively, the separating region comprises a color of a substantially different wavelength, a plurality of different wavelengths or wide spectrum light.

In some embodiments, the image of the pattern-illuminated scene is captured 702, for example using an imager such as described hereinabove. In some embodiments, the captured image is processed to restore the pattern.

Some embodiments comprise utilizing the black regions in the imaged pattern 704 for restoring the pattern and/or for reducing crosstalk. Optionally, color reconstruction is performed by subtracting measurement of the light that returns from what was projected as black regions located at opposing sides of the colored stripe of interest, from measurements of the colored stripe of interest. A potential advantage of using the non-illuminated stripes of the pattern may include robust color reconstruction of the color stripes, which is less or not affected by optical smear and/or scattering, as the black regions act to separate between the neighboring colors and provides for removal of background scattered light, such as of light scattered within the tooth In some embodiments, detection of the referential pattern is performed using an RGB Bayer filter. Alternatively, a filter suitable for transferring a different number of wavelengths (e.g. 5, 7, 10, or intermediate, larger or smaller number of wavelengths) is used for detection. Optionally, a tunable filter is used.

In some embodiments, additional local and/or global preprocessing of the pattern is applied, for example for enhancing the pattern stripes.

FIG. 8 is an example of a referential pattern 800, according to some embodiments. In some embodiments, pattern 800 comprises at least 3 or at least 7 different colors or intermediate, larger or smaller number of colors. For example, pseudo random sequence of different colors is used. In some embodiments, pattern 800 is arranged such that each colored stripe 802 is located intermediate two black regions 804, extending parallel to the colored stripe. (The colored stripes are shown in this figure in grayscale but it is noted that various colors (e.g. red, green, blue, purple, yellow) and/or combinations thereof can be used).

In some embodiments, pattern 800 comprises at least 3, at least 5, at least 7, at least 10, different colors or intermediate, larger or smaller number of colors. In this example, a recurring sequence of 5 different colors is used. (The colored stripes are shown in this figure in grayscale but it is noted that various colors (e.g. red, green, blue, purple, yellow) and/or combinations thereof can be used). In some embodiments, a pseudo-random sequence (for example of 7 colors) is used. In some embodiments, pattern 800 is arranged such that each colored stripe 802 is located intermediate two black regions 804, extending parallel to the colored stripe. For example, pseudo random sequence of different colors is used. In some embodiments, pattern 800 is may have different geometrical patterns of illuminated areas and/or dark areas. Optionally, some illuminated areas may be separated by dark regions of varying sizes and/or shapes. Alternatively and/or additionally, some illuminated areas may be adjacent to one another. For example, where illuminated areas can be accurately separated by other aspects (e.g. spectral differentiation), smaller or no intervening dark areas are used.

Optionally, the width of the black region is selected to be large enough to enable color separation in the detected image, after the projected pattern was smeared by the surface of the tooth and/or by other intra-oral contents. Optionally, the width of the black region is selected to be large enough to enable geometrical separation between neighboring colored stripes, especially when the projected pattern is reflected back from a steep area in the scene which may effectively reduce the distance between the colored lines in the detected image.

In some embodiments, a width of a black region (e.g. stripe) is selected to be 0.5, 1, 2, 3, 5, or intermediate, larger or smaller times a width of the colored stripe. Optionally, the width of the black region is selected to be large enough to enable color separation in the detected image, after the projected pattern was smeared by the surface of the tooth and/or by other intra-oral contents. Optionally, the width of the black region is selected to be large enough to enable geometrical separation between neighboring colored stripes, especially when the projected pattern is reflected back from a steep area in the scene which may effectively reduce the distance between the colored lines in the detected image.

In some embodiments, a thickness of the black stripe is selected to produce 0.3, 1, 5, 10, 30, 100 or intermediate, higher or lower number of pixels on the detector when the pattern is projected on a surface located a known distance from the imager. In some embodiments, a width of the black stripes and/or colored stripes varies between stripes. In some embodiments, the sequence of the colors is selected to maximize the distance between the colors in the color space of the detector.

For example, if the detector is an RGB detector and the colors are selected from the Red Green and Blue colors a color comprising Red and Green would be placed near a color comprising Blue only so the distance in the color space will be maximal, such as between (1,1,0) and (0,0,1).

In some embodiments, by using a predefined color sequence, the color of a detected stripe can be determined according to the known color of one or more adjacent stripes.

In some embodiments, the colors and/or the sequence of the colors is selected to be suitable for use with color spaces other than the RGB cube color space, such as HSL, HSV, CMY, CMYK and/or other color spaces.

In some embodiments color identification of illuminated pattern is done using algorithms of deep learning. The deep learning algorithms can learn to identify the pattern colors by learning many solved patterns and use for instance semantic segmentation.

In some embodiments color identification of illuminated pattern is done using algorithms of machine learning. The machine learning algorithms can learn to identify the pattern colors by learning many solved patterns and use for instance semantic segmentation.

FIG. 9 is a flowchart of a method for scanning an intra-oral scene using a pattern comprising one or more anchors, according to some embodiments.

In some embodiments, a pattern comprising one or more anchors is projected onto an intra-oral scene 900. In some embodiments, anchoring is implemented by variations between the pattern entities, for example in a stripe based pattern anchors may be realized by one or more variations in stripe width, alignment, color, missing portions, and/or other variations suitable to provide unequivocal indexing of the anchor during restoring of the pattern. In some embodiments, two or more types of anchors (e.g. variations in stripe width and missing portions) are combined in a single pattern. In some embodiments, additional anchors such as circles and/or short lines are incorporated in the pattern.

In some embodiments, anchoring is implemented by single stripe color decoding or by batch processing of a sequence of stripes. Optionally, when color coding is used, global indexing by stripe counting and/or order restriction may be performed during processing to further reduce errors in pattern restoration.

In some embodiments, the image is captured 902 and is then processed to restore the pattern, utilizing the one or anchors that were incorporated in the pattern 904.

A potential advantage of using anchors may include simplifying restoring of the pattern. Optionally, counting votes gathered from the various anchors distributed in the pattern are statistically integrated in the stripe indexing process, potentially reducing counting errors. Counting errors may be caused, for example, by stripe loss due to the scene geometry, shadows in the scene, tooth defects and/or other factors affecting the stripe shape, continuousness and/or alignment; stripe reconstruction failure and/or false detection of stripes may be caused for example by the different materials in the scene (e.g. teeth and gingiva), specular reflections from fluids in the scene (e.g. blood, saliva) and natural and/or cast shadows in the scene.

Another potential advantage of using anchors may include reducing ambiguity, which may be caused as a result of one or more of: errors in pattern restoration, and/or depth discontinuities in the scene.

In some embodiments, the amount of anchors incorporated in the pattern is selected in accordance with the amount of smooth patches in the scene. A smooth patch may include a region with no or only a small amount of depth discontinuities. Optionally, due to the relatively small amount of smooth patches in the intra-oral scene, a relatively small amount of anchors may be sufficient for restoring the pattern while maintaining stripe counting errors under a pre-defined threshold.

In some embodiments, the spread of anchors is selected taking into account the general structure of the imaged area as dictated by the optical characteristics of the image. For example, if an image of a full tooth takes up about ⅙ of field of view, at least one anchor should be present in each ⅙ portion (e.g. square portion) of the projected pattern.

In some embodiments, a projected stripe is split into segments over the smooth patches. Optionally, this discontinuity is detected by algorithmic processing and taken into consideration during indexing, so as to reduce erroneous flowing of the indexing outside of a smooth patch. In some embodiments, the amount, location and/or structure of anchors is selected to be sufficient for maintaining indexing errors under a predetermined threshold, for example under a threshold of 95%, 90%, 80% or intermediate, higher or lower detection percentages. The detection percentage may be defined as the percentage of pixels of the detected stripes that were indexed correctly.

In some embodiments, between 10-30 anchors, 5-10 anchors, 1-50 anchors or intermediate, larger or smaller amount of anchors are incorporated in a pattern.

In some embodiments, use of anchors having different signatures may provide for reducing ambiguity. Optionally, the amount of anchors having different signatures is selected to be small enough so as to facilitate restoration of the anchors. In some embodiments, in which a scene comprises only a few smooth patches, iterative region growing and confidence thresholding can be applied upon the pattern entities.

In some embodiments, anchors of various types and/or combinations of anchors are used. For example, a pair of anchors of a first type (e.g. missing portions in the stripes) is positioned near a pair of anchors of a second type (e.g. between 30 to 45 degrees and/or between 45 to 60 degrees and/or between 60 to 90 degrees). A potential advantage of pairing anchors of a certain type and/or combining anchors of various types may resolve anchor ambiguity and thereby improve detection and reducing of indexing errors.

FIG. 10 is a flowchart of a method for processing an imaged pattern, according to some embodiments of the disclosure.

In some embodiments, processing of the patterned image comprises detecting ridges and/or anchors in the pattern. A "ridge" as referred to herein may include a central long axis of a stripe; additionally or alternatively, the implied ridge can be evaluated as the center of the separating stripe, i.e. the line connecting the points which are the farthest from the "light" ridges mentioned beforehand in parallel to the stripes color change direction.

In some embodiments, detection of the ridges and/or anchors is performed using information obtained from an image that was acquired under uniform lighting. Optionally, one or more boundaries in the scene are determined using the uniform light image. For example, depth discontinuities in the scene and/or other areas prone to projected stripe loss are detected using the uniform light image. Optionally, smooth patches or borders thereof are assessed using the uniform light image. In some embodiments, assessment of smooth patches and/or their boundaries is carried out using constant parametrized segmentation, adaptive segmentation, multi-color edge detection and/or other techniques.

In some embodiments, detection of patch boundaries splits the scene into a plurality of entities, thereby potentially reducing indexing "overflow" which may occur when different pattern entities such as stripes are erroneously detected as being connected to each other. In some embodiments, once smooth patches are identified, detection and indexing of the stripes may be achieved according to the anchors of each smooth patch, under the assumption that the smooth patch does not comprise any missing stripes or parts of a stripe.

In some embodiments, in which the pattern comprises recurring entities such as stripes with dark regions between the stripes (e.g. in a referential pattern as described hereinabove), the dark regions may carry cues of stripe discontinuities. For example, if the darkest spot of a vertical line between two ridges of neighboring stripes is off-centered (i.e. is not equally distant from the two ridges), the deviation from the center may be correlative to a depth change in the scene. Additionally or alternatively, the center between two lines that follow some percentage of the maximum of the projected line, for example 10, 30, 50% or intermediate, larger or smaller value is used.

In some embodiments, ridges of the dark regions serve as pattern entities as well. Optionally, by integrating two spread functions of neighboring light stripes, the dark region ridge can be identified according to the lowest point of the function.

In some embodiments, the imaged sustainability of the dark regions to the variety of imaged materials is different from that of the light stripes. Optionally, integrating count of dark regions' ridges into the stripe indexing process may reduce the likelihood of indexing errors. In some embodiments, assessing a width of a dark region is performed to identify whether a light stripe or portion thereof is missing.

In some embodiments, iterative indexing of the ridges provides for segmenting the scene into smooth patches. In an example, a monotonic increment of the indexing along a column combined with connectivity of the ridges parallel to rows defines separate patches. In some embodiments, following the indexing process, each ridge is given a number based on its location with respect to one or more anchors. If no errors have occurred, the order of numbers given to the ridges (per each smooth patch) should be monotonic. If such order is not maintained, either an error has occurred and/or a smooth patch boundary was reached.

A potential advantage of dividing the imaged scene into independent patches may include increasing a degree of precision of the 3D model of the scene. In some embodiments, separation into patches may help maintain precision requirements during construction of the model at areas adjacent patch border lines, especially following processes such as outlier removal processes and/or resampling processes and/or smoothing processes.

In some embodiments, the detected patch boundaries are taken into account during refinement of the 3D model, for example so that smoothing of the model is performed without smoothing across the boundaries, (since they are indicative of a shifting depth in the scene). FIG. 11 is an example of a monochrome pattern 1100 comprising stripes having various widths, according to some embodiments of the disclosure.

In some embodiments, the pattern comprises stripes having at least two different widths, 3 different widths, 5 different widths or intermediate, larger or smaller number. In some embodiments, a constant width factor is introduced. In the example shown herein, pattern 1100 comprises 3 entities: a stripe 1102 of a first width, a wider stripe 1104 and a dark region or spacing 1106. Optionally, indexed portions of, for example, the wide stripe 1104 and/or narrow stripe 1102 and/or combination thereof are used as anchors for stripe counting, in one or both directions along the baseline 1108 (i.e. the line extending between imager's optical aperture and the projecting light source), for columns that contain the indexed portion.

In some embodiments, a width of the black regions is selected so as to "compensate" for the varying widths of the stripes, for example so that the distances between stripe centers remain constant.

A potential of using a monochrome pattern for example as described herein may include simplifying projection, reducing power requirements and/or reducing the effective modulation transfer function of the imager. These may provide for an imager of a small form factor.

FIG. 12 is an example of a monochrome pattern 1200 comprising one or more diagonals, according to some embodiments of the disclosure.

In some embodiments, one or more diagonals 1202 are incorporated in the pattern. In some embodiments, diagonal 1202 crosses at least two stripes of the pattern, producing junctions 1204 with a crossed stripe. On each of the stripes, the junction is formed at a horizontal location which is different than junction location of the same diagonal with other stripes. In some embodiments, the horizontal location contributes to indexing of the stripes, since the horizontal location in a reflected stripe remains similar to the one that was projected. In some embodiments, detection of junctions in a certain sector of rows and columns in the acquired image can be traced to a specific diagonal and the stripe it crosses, thereby limiting the number of possibilities and resolving ambiguity between the different diagonals.

In some embodiments, the number of diagonals is selected according to possible vertical movement of the reflected stripes as the stripes are returned from various depths in the scene. Additionally or alternatively, the number of diagonals is selected to be sufficient to maintain indexing errors under a predefined threshold.

In some embodiments, an angle between the diagonal and the baseline is between 10-80 degrees, such as 30 degrees, 45 degrees, 50 degrees, 60 degrees or intermediate, larger or smaller angles. In some embodiments, the angle is selected in accordance with a distance between stripes and/or in accordance with stripe width, for example so that a horizontal distance between two adjacent junctions will be above a predefined threshold for accurately identifying the junctions.

In some embodiments, a geometrical position of the diagonals in the pattern is selected so that one or more diagonals would be located at a predefined region in the received image when the pattern is returned from a surface at a known distance, e.g. returned from approximately a middle of the depth of the focus range. In an example, a diagonal is positioned in the pattern so that it extends from an upper left corner of the image to the bottom right corner of the image.

In some embodiments, the diagonal lines are surrounded by dark area when they cross the horizontal stripe. The dark area can be similar in thickness to the dark area between the stripes or smaller or larger. A potential advantage of a dark area at the crossing may include facilitating detection of the diagonals.

In some embodiments, spacing between adjacent diagonals is selected to be sufficient to reduce a likelihood of the imaged diagonals intersecting each other.

In some embodiments, additional signatures are incorporated to facilitate detection and/or reduce ambiguities in diagonal detection.

FIGS. 13A-B are examples of patterns comprising multiple color zones, according to some embodiments of the disclosure.

In some embodiments, stripes of the pattern are divided into multiple color zones, such as 2, 3, 4, 6, 8, color zones or intermediate, larger or smaller number. Optionally, each color zone comprises one or more stripes. In the examples shown herein, the patterns comprise 3 grayscale color zones.

In some embodiments, multiple color zones are utilized in color patterns as well.

In some embodiments, for example as shown in FIG. 13B, two or more coding strategies may be combined in a single pattern. For example, multiple color zones are used in a pattern comprising to diagonals. In such combination, multiple color zones may be efficient to reduce ambiguity between the various diagonals in the pattern.

In some embodiments, color is incorporated in various components of the pattern, such as within one or more stripes; within areas between white stripes; within diagonals, wide stripes, and/or other anchors; within junctions; and/or other pattern components or combinations thereof. In an example, a wide stripe comprises colored stripes adjacent it. Optionally, stripes above and below the wide stripe are different in color. Optionally, different wide stripes are surrounded by stripes of different colors, to allow for differentiating between the wide stripes. In some embodiments, a color sequence is selected to obtain a large distance in the color space between spatially close colors. The color space may include RGB, HSV, CMY, CMYK and/or other color spaces.

FIG. 14 is an example of a pattern 1400 comprising one or more calibration elements, according to some embodiments. In some embodiments, a calibration element comprises one or more shapes, colors, and/or other entities configured to facilitate quantifying the optical characteristics of the scene and/or of the optical characteristics of the scanner, such as focus and/or reflection direction and/or color. Exemplary calibration elements include one or more of: fine lines set at varying distances from each other 1402; a checkered board arrangement; a block having a slanted edge 1404, and/or other elements suitable to facilitate optical calibration, such as calibrate the MTF of the optical system for example using MTF measurements known in the art. Optionally, a calibration element comprises entities of different colors, for example grayscale entities as shown in element 1406, which can be used to calibrate, for instance, LED power or exposure.

In some embodiments, positioning of the calibration elements is selected so that at least one calibration element is visible in the imager's field of view as the depth changes and the imager captures different areas of the projected pattern. In some embodiments, the calibration elements are removed from the detected image using image processing techniques.

It is noted that scanning patterns incorporating combinations of coding schemes for example as described hereinabove are also contemplated by this application. For example, a color coded pattern may include stripes of various widths; a color coded pattern may include diagonals; a color coded pattern may include a probe window; a monochrome pattern may include stripes of various widths and diagonals; and/or other combinations.

In some embodiments, a referential pattern is used for accurate extraction of illuminated objects (e.g. tooth, inlays, crowns, gums, tongue, carry, gloves or other intraoral features) and/or geometry. Optionally, the referential pattern includes multiple projected entities. Optionally, at least some of the projected entities have a different spectral footprint.

In some embodiments, the following process is performed:

Illuminate object with a referential pattern

Take an image

Optionally an image is made of the objects illuminated by the referential pattern Optionally one or more spectral images are made of the objects illuminated by the referential pattern and/or two or more spectral bands are differentiated Optionally take also an ambient image (e.g. without pattern illumination)

Optionally take also an image with uniform illumination

Optionally take also an image with uniform white illumination

Correct pattern features colors for example by

Optionally using non illuminated areas in said referential pattern.

Optionally differentiating projected entities based on their spectral footprint

Optionally using uniform illumination image and/or ambient image as described herein above.

Compute a depth map of the surface of one or more illuminated objects

FIG. 15 is an exemplary illustration of color sensitivity bands of a Bayer filer (source U.S. Pat. No. 9,593,982 FIG. 2). In some cases the sensitivity bands of a Bayer filter may be wide. For example, the pass band may range between 25 to 50 nm. For example, the transition band may range between 40 to 100 nm. The sensitivity in the overlap between bands may be as high as 50% of the sensitivity in the pass band.

In some embodiments, a hyperspectral camera with bands such as schematically shown at FIG. 5B can include a set of narrowband filters over the range 400-500 nm or over the visible range 400-700 nm, or visible and IR range 400-850 nm or another spectral range. In some embodiments, narrow color bands may have a passband width FWHM (Full Width Half Max) ranging between 80 to 15 nm and/or 40 to 10 nm and/or 20 to 5 nm and/or less than 5 nm. For example narrow color bands may have a transition band width ranging between 50 to 25 nm and/or from 25 to 15 nm and/or 15 to 10 nm and/or 10 to 5 nm and/or less than 5 nm. Optionally, a sensor array may be focused in long wavelength light for example ranging between 500 to 600 nm and/or between 600 to 700 nm.

In some embodiments, crosstalk may be reduced by selecting an order of bands. For example, the spectral signature of neighboring projected entities may be selected to have reduced spectral cross talk. For example, entity colors may be chosen to create large spatial distance between entities that are close in the frequency domain. For example a stripe stripes may be ordered with a center of their band range at staggered rather than in strictly increasing or decreasing order. For example, the order of range centers may be 550, 400, 600, 450, 650, 500, 700, 550. For example this gives a minimal 150 nm difference and even distribution. If the bands where ordered on strict increasing or decreasing would have a distance of 50 nm neighboring bands.

FIG. 16 illustrates additional options of narrowband filters with different levels of spectral crosstalk in accordance with an embodiment of the current disclosure. In some embodiments, decreasing the band width and/or the overlap between bands, for example as illustrated by bands 160, decrease the crosstalk between different bands. In some cases, decreasing the band width decreases also the transmitted light and the detection SNR. Increasing the band width, for example as illustrated by bands 161 may in some cases increase the detection SNR. Increasing the bandwidth may also increase spectral crosstalk and/or may reduce the chance of error in identification of the correct projected structure.

FIG. 17 illustrates an image of referential stripes pattern illuminated over a tooth in accordance with an embodiment of the present disclosure. For example, the image of FIG. 17 is monochromatic. Alternatively or additionally, spectral features, for example color images may be captured as well. For example, as described before, after obtaining the depth map of tooth 170, the image is corrected locally for the known PSF of the optical system (e.g. referential pattern projector and imager). Tooth 170 is optionally illuminated by stripes 171 (green) and 173 (blue) with a referential black gap 172 in-between. In FIG. 16, the effect of scattering can be seen in that black gap 172 is illuminated by light that migrate through tooth 170 from other stripes.

Ambient Estimation

In some embodiments, the ambient illumination is estimated by taking an image without any illumination (e.g. pattern or uniform illumination). Optionally, an image of a referential pattern may be corrected by subtracting the effect of the ambient light. For example, after subtracting the effect of ambient illumination, the corrected image may be used for identification of said referential pattern colors and/or for depth mapping.

In some embodiments stripe colors are estimated by dividing the image of the pattern illumination by image of uniform white illumination. In some embodiments stripe colors is to estimated by dividing the image of pattern illumination after ambient subtraction by image of uniform white illumination. For example, the division may help reduce confounding effects on the depth mapping due to local variations in the color of tissue.

FIGS. 18A and 18B illustrate structures of a sensor array in accordance with embodiments of the current disclosure. In some embodiments, a sensor array (for example a CMOS) will be used to capture an image. Alternatively or additionally, an image can be captured by scanning a scene. In some embodiment, use of a sensor array has an advantage of producing the image of multiple colors and/or multiple locations simultaneously. For example, the senor array may reduce problems due to movement and/or changes in lighting over time. For example, simultaneously producing a multi-color image may make it easier to relate between features seen with different sensors.

In some embodiments a sensor array will include spectral sensors (marked B1-B5 in FIG. 18A) and/or wide band sensors (for example a monochrome sensor sensitive to the entire visible spectrum (e.g. without a filter)) marked C in FIG. 18A. For example, there may be a large number of high sensitivity large band filters to capture the geometry of projected entities. Optionally, a smaller number of color filtered sensors are used for spectral differentiate of the projected entities. In some embodiments the colored pixels may be covered with narrowband filters, such as interference filters. The wideband sensors may have higher sensitivity since the color filter absorbs some of the light. Additionally or alternatively, the wideband sensors may sense all the projected colored features (e.g. all the lines in a colored lines pattern). For example, the wideband sensors may be used to provide higher accuracy in locating the feature in the image (e.g. locating a line in accuracy of 1/10 pixel). Optionally higher accuracy 2D images are used to produce higher depth accuracy. In some embodiments, the pattern of sensors on a sensor array and/or the order of scanning of a scanning sensor may be adjusted to improve imaging of the pattern of the projected entities. For example, for a projected pattern of horizontal lines (for example as illustrated in FIG. 17) the sensors in a sensor array may be arranged perpendicular to the stripes (e.g. in vertical columns of similar sensors as illustrated in FIG. 18B). For example, this may give good resolution of the position of the lines in each spectral band and/or enable good depth accuracy. Alternatively or additionally, the lines of sensors in the array may be another angle (e.g. diagonal) with respect to the lines on the pattern and may provide better sampling of the measured space while the 3D scanner is scanned over the object. Alternatively or additionally a column of sensors may include multiple colors.

In some embodiments, the mix of sensor may be adjusted according to the range of colors to be measured. For example, using the 3 colors of RGB Bayer filter over a CMOS, to detect a pattern that is focused in the violet-blue-green range the sensors mix may include an increased number of blue filters. For example for a blue pattern, the blue pixels may have improved sensitivity over green pixels and/or the red pixels may have the lower sensitivity then the green. Optionally the sensor will include increased blue and green sensors (pixels) and decreased red pixels (for example the red pixels may be useful for imaging specular areas). For instance the Bayer pattern (CFA—Color Filter Array) can be GBBR instead of the common RGB which is B G G R. In some embodiments the contrast of the blue spectrum of the projected lines is better. For example an increased number of blue pixels in the filter array may provide better accuracy of locating the projected pattern (e.g. lines) and/or better depth accuracy.

Optical Properties

In some embodiments, a referential pattern is used for bulk optical properties extraction of an illuminated object (e.g. tooth, inlays, crowns, gums, tongue, carry or other intraoral features). Alternatively or additionally, a referential pattern is used for extraction of subsurface properties and/or surface properties and/or point properties. For example optical properties of subsurface features, areas and/or layers optical properties (i.e. not the outer surface) may be measured and/or estimated. The measured properties may be used, for example to facilitate accurate esthetic restoration.

In some embodiments, the following process may include some or all of the following actions:

Illuminate object with a referential pattern

Take an image of the object illuminated with the referential pattern

Optionally take a further image of the object, for example:
an image under ambient illumination (e.g. without pattern illumination)
an image under uniform illumination
an image under white illumination Optionally correct pattern features and/or colors. For example, corrections may be based on data from different illumination schemes. For example, corrections to illuminated areas in a pattern may be based on data from non-illuminated areas the pattern. Alternatively or additionally, corrections may be based on images made under ambient light, uniform light and/or white illumination.

Optionally, generate a depth map of illuminated object

For a plurality of areas in the image (e.g. areas with relatively uniform properties and/or limited depth variation, for instance depth variation <5 mm) do some or all of the following optional processes:

determine local depth estimate optics (e.g. projector and imager) local PSF (point spread function) using calibration information Deconvolve with PSF function (i.e. remove the effect of optics defocus)

resolve the amount of light scattered through the illuminated object vs. distance from illuminated feature and illuminated feature wavelength (for example as explained for the exemplary stripes illumination of FIG. 17 below).

compute a measure of scattering for example $\mu_s$, $\mu_a$ (reduced scattering and absorption coefficients). Optionally the scattering coefficient will be computed as a function of depth from surface, location on object and/or illumination wavelength Optionally, gather optical properties information for multiple illuminated locations on the object depth map (e.g. 3D model) during scan Optionally integrate gathered optical properties information over a 3D model optionally including non-measure areas (e.g. by interpolation and/or extrapolation). For example, a 3D model may be constructed which allows estimation of optical properties vs. wavelength and/or depth within the tooth or the tissue for each location on 3D model Optionally, render the object in 3D. For example, rendering may employ known systems for example, NVIDIA and/or GameWorks, Translucency Rendering, in order to show the dentist or the patient the realistic 3D model of the tooth In some embodiments, the optical properties may be used to choose a material to use in the CAM machine. For example multi-layer Zirconia or the relevant material may be used for milling in each area of the model. For example, materials may be shaped using additive manufacturing which include several layers of the tooth with different optical properties. For instance, 5 layers, with thickness of 0.1 mm, each one has different color and scattering coefficient. For example a look up table may be used to correlate optical properties, materials and/or measurements.

In some embodiments, intra-oral features may be illuminated with a referential pattern. For example as illustrated FIG. 17 illustrates a pattern 800 including 7 different colors. Optionally the colors are presented in a pseudo random sequence. For example, in pattern 800 each colored stripe 802 is third the width of each black region 804.

Measuring Optical Properties

FIG. 20A is a schematic illustration of paths of light passing through a tooth 151a. Optionally, a tooth 151a is illuminated with a striped pattern. For example the pattern includes a stripe 152, schematically shown as a black line on an upper surface of tooth 151a. In some embodiments photons may be reflected from tooth surface and/or scattered and/or absorbed. Without being limited to a theoretical framework, calculations may be based on an approximation, for example one possible approximation is that a photon migrating through strongly scattering media, such as tissue or teeth that enters the media at some point and is measured at another point, may follow a banana shaped volume distribution in the media. The theoretical construct and some calculations for this approximation is described for instance in Feng S. et al. "Monte Carlo simulation of photon migration path distributions in multiple scattering media" Proc SPIE vol. 1888, (1993). The optical properties (absorption and scattering) of the tissue are optionally extracted from the number of photons which are measured at each distance from the illuminated stripe 152. Additionally or alternatively, measurement of light at different distances from the illumination stripe provides information on the optical properties vs. depth from the tooth surface.

The effective penetration depth of each "banana" can be expressed as $$z \sim d*2 - 1.5$$

where d is the illuminated point measured distance, as shown schematically for example in FIG. 20A for illuminated strip 152 and measuring at point 155 with distance d, the effective "banana shape" photon path distribution 158 gets to effective penetration depth z.

FIG. 20B is a schematic illustration of light reflecting from a Titanium restoration 151b. Some materials are highly opaque and/or have minimal scattering. For example, restoration 151b, the light scattered through the medium is negligible. The Titanium can be recognized for example by the lack of significant scattering from dark areas and/or from reflected light 159 (e.g. its color and/or intensity). For example, a metal restoration may be recognized by it color and/or its low level of scattering in dark areas. Another example which can be recognized is demineralization of the tooth enamel. that is optionally detected by color change to a whiter shade or a low scattering of photons inside that area compared to scattering of photons in case of healthy enamel.

FIG. 20C is a schematic illustration of a tooth having a biofilm 2012 (e.g. plaque) coating. In some embodiments, a biofilm will not change much the scattering at depth. In some embodiments the biofilm will change the reflectivity of the surface of the tooth (for example reducing reflectivity and/or darkening the shade) and/or block (obscure) a portion of the scattered light. Alternatively or additionally, the film will cause fluorescence 2011 in a frequency other than the frequency of the applied light 152. Optionally the presence of a biofilm and/or another fluorescing feature may be determined by detecting that returning light is at a different frequency than the applied light 152. For example, demineralization of the tooth enamel can be detected in this manner, by detecting that returning light is at a different frequency than the applied light 152. Optionally, the fluorescence will be combined with other changes for example change in reflectance and/or obscuring scattered light.

FIG. 20D is a schematic illustration of light scattered from a heterogeneous feature, for example a restoration with an outer colored layer and an inner support layer and/or a tooth with a layer of enamel over a deeper layer and/or a tooth with a layer of plaque over a layer of enamel. In some embodiments, reflectance and/or scattering 153 near the surface will be characteristic of the surface layer 151c. In some embodiments, scattering (e.g. scattered light 2014 and/or 2015) away from the applied pattern 152 will include characteristics of the deeper area 151d. For example, in exemplary embodiment of FIG. 20D the deeper area 151d has a higher transparence than the surface layer 151c. In some cases, that high transparency lower area 151d will cause the light scattered from the deeper layer (e.g. 2017, 2018) to spread 2016 further from the light pattern 152 than in a homogeneous media and/or for light to be seen further away from the location of the light pattern 152 (for example as illustrated in light 2014 and 2015).

In some embodiments, different colors and/or the difference in properties for different wavelengths may differentiate between features (e.g. gums, teeth, restorations) and/or between healthy areas and/or unhealthy areas (for example by detecting the presence of a biofilm and/or a change in geometry (for example reduction of bone mass).

An exemplary image of a pattern of referential stripes illuminated over a tooth is show in FIG. 17. FIG. 17 illustrates a monochrome image. In some embodiments, the image may include conventional color and/or hyper spectral color data. Optionally, a depth map of tooth 170 is acquired. In some embodiments, the image is corrected locally for PSF. For example, the PSF of the optical system (e.g. referential pattern projector and/or imager) may be known.

In some embodiments, the referential black gap 172 is illuminated by light that migrates through tooth 170 from the illuminated stripes 173 and/or 171. For example, stripe 171 may be of a first color (e.g. green) and stripe 173 may be a second color (e.g. blue) with an optional referential black gap 172 in-between. A profile of gray level intensity is illustrated in FIG. 19. Optionally, profile may be locally averaged parallel to the stripe direction (for example from horizontal coordinates 100 to 200 of FIG. 17). In some embodiments, averaging along the stripe improves the SNR and/or reduces the effect of dirt and/or stains on small areas of the tooth 170. In some embodiments, an estimate of background scattered illumination is made. For example, the estimate may be based on a referential illumination value. For example the referential value may be the illumination in the center of the black gap.

Graph 180 is an illustration of the light intensity in the exemplary image of a pattern of a tooth 171 illustrated in FIG. 17. Gray level intensity of stripes 171 and 173 are illustrated as peaks 181 and 183 respectively and referential black gap 172 as valley 182. The decay profile of green stripe 171, as shown at window 184 is wider than the decay profile of blue stripe 173 shown in window 185. For example this may be because blue has reduced scattering $\mu_s{'}$ that is larger and/or the blue absorption $\mu_a$ that is higher. From analyzing all decay profiles such as 184 and 185 for all the referential patterns images $\mu_s{'}$ and $\mu_a$ can be found over all the scanned teeth vs. depth from surface, location on object and illumination wavelength.

In some embodiments, a supplementary object may be used during dental scanning. For example, a probe may be used for example for subgingival measurements. In some embodiments, the supplementary object may cast a shadow over a portion of a tooth, for example by blocking the patterned light and/or constant light. Optionally a shadow is used in the same was as a black region 804 (for example as described above) and/or is used to identify and/or correct identified optical properties. In some embodiments, the shadow is perpendicular to a projected black region. For example, based on different direction black regions changes of optical properties are identified in different directions (for example up and down using the black regions and right and left using the elongate body shadow). In some embodiments, the shadow might be wider than the projected black regions. For example, the larger black region may allow imaging from a larger distance than for smaller regions. For example, images with a larger black region may be used to identify a higher effective penetration depth z.

In some embodiments, an image may be used to identify spectral diffuse reflectance R. For example, an image of a referential pattern may be analyzed. For examples peaks such as 181 and 183 provides the spectral diffuse reflectance $R_\lambda$ (i.e. color) of each location illuminated by referential stripes pattern. Measured properties, for example diffusive reflectance may be corrected for the scattered light, for example by subtracting the estimated intensity of scattering. Optionally, estimation of scatter may be based on measurements made in the black referential gaps. Measured properties, for example diffusive reflectance may be corrected for the ambient illumination for example by subtracting the estimated intensity of the ambient light.

In some embodiments, an image may be used to determine a local florescence of a tooth. Optionally, an image of a referential pattern is used also for gathering local florescence of the tooth. Florescence may be interpreted to identify the presence of organic materials and/or tooth decay. The florescence is obtained, for example, by measuring the amount of light emitted at a different wavelength than the light projected onto a dental feature (e.g. a tooth). For example, light at higher wavelengths emitted from a blue illuminated area, such as strip 173 in FIG. 17. To get accurate estimation of the concentration of the material that emits the florescence (e.g. plaque) light, the effects of ambient and/or absorption and/or scattering and/or distance and/or angle of both the absorbed and the emitted light can be compensated, for example, as described herein above.

In some embodiments, the scattering coefficient $\mu_s$ and\or the anisotropy g are used instead or together with the reduced scattering coefficient $\mu_s{'}$ or other optical properties or coefficients used for better description of the tooth.

The local $\mu_s{'}, \mu_a, R_\lambda$, florescence and any additional needed optical properties are gathered for each illuminated location on object depth map (e.g. 3D model) during the tooth scan. Some of the optical properties are also related to deeper layers (e.g. measured with dipper 'bananas') of the tooth are added at the correct depth location in the 3D model. All the gathered optical properties information over the 3D model are integrated to provide optical properties vs. wavelength and layer depth (i.e. depth below the surface) for each location on 3D model. In some embodiments all the gathered optical properties information over all 3D model is integrated to provide optical properties vs. wavelength in a 3D voxel representation of intraoral scene, e.g. each location within the teeth and gums is represented by a voxel. In some embodiments, said voxel size is 10 um or 50 um or 100 um smaller or larger. Each voxel can include information on the local optical properties or any other local properties.

FIG. 21 is a flowchart illustration measuring optical properties of an intra oral feature in accordance with an embodiment of the current disclosure. In some embodiments, a multi-color pattern is projected 2102 onto the feature. For example, patterns may include lines of different colors and/or black lines and/or other forms. Different locations may be imaged with the same colors and/or one location may be imaged using different colors for example as described herein above and below. One or more images 2104 are optionally made of the feature with the pattern. For example, images may be made of the object with the colored pattern. In some embodiments, individual lines and/or parts of a projected pattern will be identified in the image, for example this may increase the accuracy and/or precision of the model resulting from the image. Alternatively or additionally, images may be made of the object under an alternative light source, for example ambient light and/or a multiple patterns and/or uniform light.

In some embodiments, a depth map of the feature may be generated 2106. Optionally, during generation of the depth map, the colors of the pattern objects will be identified and used to improve the differentiation of different patter objects and/or the mapping of position. Optionally the data may be corrected 2107. For example, an imaged may corrected 2107 based on the structural model, and/or integrated data from objects under different lighting may be used to correct an image. For example, corrections may include corrections in the color of an object based on the distance of an object from a light source and/or based on an angle of the object with relation to the light source and/or the angle of the object to the imager. Alternatively or additionally, corrections may be based on an effect of background light and/or scattered light for example, by comparing measurements made under different lighting conditions (for example illuminated regions vs. dark regions and/or regions illuminated under one color of vs. the region illuminated with another color). For example, the position of a surface may be adjusted to account for light scattered from behind the surface. Based on the corrected image data, various properties may be determined at various parts of the image. For example, optical properties and/or their 3D distribution may be determined including color, translucency, scattering, reflectance, and refractance. Corrections 2106 may include various image enhancements and/or model corrections as described for example herein below.

Identifying Intra-Oral Objects

FIG. 22 is a flow chart illustration of identifying intra-oral features in accordance with an embodiment of the current disclosure. In some embodiments, measured optical properties are used to identify 2110 an intra-oral feature. For example, an identified feature may be segmented from other features and/or objects. For example, a feature may include an object (e.g. a tooth, a filling, a biofilm, a cavity, an area where gums have receded, an area of bone loss) and/or materials (e.g. organic material, enamel, living tissue) and/or geometric element (e.g. a ridge, a hole, a boundary).

Optionally the feature may be on a visible surface. Alternatively or additionally an obscured feature may be identified 2110 below a surface of a dental object (e.g. a tooth) and obscured by another object (e.g. blood, glare). For example data about optical properties at different wavelengths and/or spectroscopic data about optical properties at different locations and/or at different depths underneath the tooth surface may be used to infer material properties. For instance, material properties inferred from optical measurements may be used to identify 2110 restorations materials, dentin, enamel, decay etc. Other properties include detecting changes to dental materials due to medical conditions, tooth maintenance and/or natural changes. For instance, identifying demineralization or decalcification of tooth enamel. In some embodiments, a processor will be used to determine 2008 properties and/or identify features. For example, a fixed algorithm may be used to segment an image and/or identify features. In some embodiments, artificial intelligence for example including deep learning may be used. Optionally, objects identified 2110 and/or properties determined 2008 will be rendered 2112 to a user. For example, rendering may include displaying an obscured feature will with interfering objects left out and/or displaying a cross section of an object and/or highlighting certain features. Segmentation and identification for example as described herein below. For example, dental pathologies may be identified 2110 and/or signs of pathologies may be highlighted during rendering 2112.

Tooth Segmentation and Classification

In some embodiments, to classify objects in the image, for instance tooth or gums, color (such as RGB) images are collected from patterned images. Optionally, images are made of the objects using a referential pattern, for example lines pattern as described herein above. In some embodiments, known locations of the teeth and gums are used to build a model. The color data is optionally sorted according to its location in the image with respect to the lines on the image. Data is optionally processed. For example, the locations of the illuminated lines are identified and the position of each line center is marked, as well as the position of the center of the area between each two lines—the "dark lines". Optionally color data is collected for each illuminated line and for each dark line. For example, the illuminated lines may provide measurements of the spectral reflection for each color in the pattern. The information that the dark lines optionally provides optical properties obtained from light that was scattered thorough the tooth or the tissue (for example tooth and/or gums) from the illuminated lines to the dark area in between the lines.

In some embodiments, for each pattern object (for example illuminated and/or dark lines) a model is built based on the known data to separate the teeth from the gum. This model can use, for example, RGB data, HSV data (derived from the RGB data) and/or another color format, and/or a combination of several color formats at once. The model may be built from the entirety of the data, from data from only on the dark lines, only on the illuminated lines, and/or for each line separately. The model may use one or more of classification algorithms, such as k-nearest neighbors, a classification tree, using some other advanced algorithm, such as, but not limited to, neural network or deep learning. In some embodiments, the model is built on a classification for example, on RGB and location such that for each possible RGB and location combination a classification is given. In some embodiments, this facilitates a quick rendering of classification. In some embodiments, from the model shades or each area and/or feature are identified. Optionally, the model obtained may be saved for later scans with similar referential pattern, colors and spacing.

Optionally the results are output. Optionally, the classification enables exporting separate 3D models for teeth and for gums. For example, separate gingiva scan can be exported to one file and a prepared-teeth-only scan can be exported to a different file Producing Objects for Dental Restoration FIG. 23 is a flow chart illustration of producing an object for oral restoration in accordance with an embodiment of the current disclosure. In some embodiments, measured optical properties of an intraoral object (e.g. a tooth) are mapped 2114 and/or used to produce an esthetically matched dental restoration. For example, properties and/or features may be measured and/or inferred (for example, including identifying features and/or determining properties as described herein above and below). Optionally properties and/or features may be used to identify the manufacturer of an existing restoration material. For example, one may choose 2116 to use the same material and or manufacturer for a new restoration. Information about available materials may be used to choose a matching material for new treatment and/or restoration. For example, the optical properties information of a tooth may be measured near a location where it is planned to add a restorative object (for example a filling and/or a crown and/or an implant). For example the optical measurements may be used in order to create the restoration to be as close as possible to a nearby tooth.

In some embodiments, obtained measurements are used for estimating a property and/or location of an obscured object. For example, an object may be obscured by tissue, blood and/or other fluids. In some embodiments, a 3D distribution of optical properties is obtained. For example, the 3D distribution of optical properties may be used to generate a 3D model and/or for estimating the location of the obscured object. For example, optical measurements may be used to determine a location of a tooth wall location below a layer of blood. Alternatively or additionally optical measurements may be used to determine a location of a subgingival finish line covered by gums.

In some embodiments, obtained optical properties are used for segmentation of a 3D model to teeth and gums. For example, the segmentation may be used for displaying to the user a particular object and/or kind of tissue. Optionally, a 3D model of an object (for example a tooth) may be displayed including obscured portions without obscuring tissue. In some embodiments, segmentation of the 3D model is used to identify areas where the external appearance obscures internal structures. For example, this may use to identify conditions that are causing the structures to be obscured. For example, bleeding may be identified by identifying tooth areas which are covered by blooding. For example, areas of bleeding may be indicated to the user. In some embodiments, obtained optical properties are used for segmentation of the 3D model to identify natural teeth and/or added objects such as restorations and/or fillings. The different sections and/or objects may be shown to a user on 3D model. In some embodiments, obtained optical properties are used for identifying thickness of areas and/or layers of the tooth, which may be in some cases shown as a 3D model to the user. For example, local enamel layer thickness on top of dentin may be shown. Another example, local crown thickness on top of tooth or metal cap may be shown to the user. Another example decay layer thickness on top of tooth may be shown. Another example a decay layer beneath a crown may be shown.

In some embodiments, obtained optical properties are used to detect a prepared tooth (for example when preparing a crown) that will have a different outer layer than a normal tooth. This segmentation may help the 3D scanning algorithms with the restoration. For example, understanding the position and/or geometry of the prepared tooth will help the algorithm to project the probe tip on the prepared tooth while the dentist is scanning around the prepared tooth with an elongate body (e.g. a probe) that can be used also for subgingival measurements.

In some embodiments, obtained optical properties are used to compensate on errors in the detection of the lines that create the depth map for example, to get more accurate depth. For example, an image of a projected line on an inlay may present the center of the line in a different place than the center of the line that is projected on enamel, even if they are on the same depth, because of difference in the scattering properties. In some embodiments, the compensation is also dependent on the projection angle with regard to the tooth that is obtained from the depth map and camera position estimation.

In some embodiment a chosen material will be used to build 2118 a restoration. For example, computer aided manufacturing CAM may be employed. For example multilayer Zirconia or the relevant material may be acquired with desired properties for different areas of the restoration.

Alternatively or additionally, a paste having custom properties may be mixed for use in a filling.

For example, materials may be shaped using additive manufacturing.

Optionally after building the restoration it may be finished 2020 for example by milling and/or surface treatment and/or by connection to a mounting structure.

Image Enhancement

In some embodiments, the ambient illumination is estimated. For example, an effect of ambient illumination may be estimated based on an image may be taken without additional illumination (e.g. pattern or uniform illumination). Optionally, non-illuminated images may be made periodically. Images made under special illumination (for example with a reference pattern illumination and/or uniform illumination) may be corrected by subtracting the estimated effect of the ambient illumination.

In some embodiments, pattern colors are enhanced and/or estimated by dividing an image of pattern illumination by image of uniform white illumination. For example, the intensity of each pixel may be divided by the intensity of the pixel in the white illumination image. The optionally division may remove some of the effect of the material optical properties, such as color, optical reflectance, absorption etc. to get the color of the projected pattern. Optionally, division is performed after correcting an image. For example, stripe colors are estimated by dividing image of pattern illumination after correction of ambient light by a uniform white illumination after correction for ambient light.

In some embodiments, the ambient illumination is estimated by using a reference object. For example a white diffuse target may be mounted on the IOS, such that it covers a portion of at least one camera FOV. From the image of the target and the known target properties and angle, the total illumination can be measured target location. Optionally, the strength and direction of the applied illumination at the target location is known (and/or negligible) and/or the ambient illumination at the target location can be estimated based on known calibration and/or the difference between the measured illumination and the known applied illumination. Optionally multiple targets are supplied at different angles and/or locations. The ambient illumination and/or calibration for the imager and/or applied illumination may be estimated for various surfaces in an image from the measured target images. For example, interpolation and/or extrapolation may be applied to find the effect of ambient light at different locations in the image. In some embodiments, also an image of the object and/or the diffusive target 3D model are used for better estimation of ambient effect on the whole FOV using measured light. In some embodiments, also the object and/or the diffusive target optical properties obtained for example as described before and/or are used for better estimation of ambient effect on the whole object using measured target.

In some embodiments, the ambient illumination direction is estimated from images on one or more reference surfaces have different directions. For example, one or more reference surfaces may be mounted on the IOS in the FOV having portions of the surface facing different directions. The difference between the ambient effect on the reference surfaces pointed in different directions and/or the differences between different references at different locations can be used to estimate the illumination direction and/or non-uniformity in illumination.

In some embodiments, said target or targets are located on an elongate body that can be used also for subgingival measurements as describe for example in U.S. Pat. No. 9,454,846. Using a reference in different distance from the scanner cameras can also contribute to the estimation of the 3D vector or vectors that the ambient light is coming from.

In some embodiments, a hyper spectral imager is used to capture special color bands in an image. For example a hyper spectral CMOS imager may be used. Optionally the hyper spectral imager is used to image light in a narrow band of wavelengths. For example a hyper spectral imager may be used to capture images of a tooth or another intraoral object in multiple wavelength bands. For example, the tooth optical properties may be characterized in Red Blue and/or Green and/or in other wavelengths for example including Yellow, Cyan and/or Magenta for example. In some embodiments, hyper spectral images are used to detect non-linear reflections and/or fluorescence. One or more of the hyper spectral bands may be in the range of the reflected wavelength. In some embodiments, the optical properties for each wavelength can be measured using white illumination and hyper spectral detection to identify optical properties in each band.

In some embodiments, one or more image processing algorithms such as spatial filtering, adaptive histogram equalization, local thresholding, non-maximum suppression, and/or other algorithms are applied to an imaged pattern. For example, image processing may be applied to enhance pattern contrast, color, assessment of ridge location and/or other characteristics a region that includes light and dark patterns.

Use of dark separation regions may be adjusted according to the geometric and/or optical properties of an imaged region. For example, when processing areas in which a distance between the stripes decreases, for example in areas exhibiting steep angles towards the imager, processing may account for the higher probability of a crosstalk and interference.

In some embodiments, wavelengths of the pattern are selected from the visible wavelength range. Optionally, the wavelengths are selected from the lower end of the visible range, for example between 400-500 nm, or intermediate, higher or lower ranges. A potential advantage of selecting wavelengths from the lower end of the visible range may include maximizing contrast when scanning teeth. Also, wavelengths of the lower end of the visible range may be easily observed on the gingiva. Additionally or alternatively, the pattern includes a combination of wavelengths from the visible range and other regions of the electromagnetic spectrum, e.g. wavelengths of the IR range and/or UV range. In some embodiments an IR (Infra-Red) range and/or a NIR (Near-Infra-Red) range can also be used for trans-illumination of teeth, potentially providing more data that potentially helps identification of different materials and different situations of materials. By way of a non-limiting example, demineralization of tooth enamel can be detected using a NIR line or stripe in the pattern and detection of scattering of the NIR photons from healthy enamel as different from scattering of NIR photons from demineralized enamel.

In some embodiments, more than one pattern projector, of more than one imager, are optionally used. Such use potentially increases accuracy of detected optical parameters. By way of a non-limiting example, using two projectors, using 4 projectors, using 6 projectors, or using a higher number or an intermediate number of projectors.

In some embodiments the more-than-one projectors optionally project on a same area of the teeth. Such projection using several projectors can potentially reduce measurement errors, by way of a non-limiting example by using averaging of the values that are calculated for each projector.

In some embodiments, more than one imager is used to image in the oral cavity. By way of a non-limiting example, two imagers, four imagers, or a higher or an intermediate number of imagers are optionally used.

In some embodiments the more-than-one imagers optionally image a same area of the teeth, or an at least partially-overlapping area of the teeth. Such imaging using several imagers can potentially reduces measurement errors, by way of a non-limiting example by averaging of the values that are calculated based on images from each imager.

In some embodiments, changes in a projected pattern, for example different wavelengths or different wavelength ranges in one or more projector, are optionally used.

In some embodiments, a same area of the teeth is optionally illuminated with different wavelengths, different colors. Images of the same area are optionally captured at different wavelengths. Different wavelength potentially penetrate to different depths within a tooth, potentially traverse different paths within a tooth. In some embodiments the images captured of the same area at the different wavelengths are optionally compared, optionally enabling determining materials comprised within the tooth.

Using different wavelengths on the same area of the teeth potentially enables a deeper inspection of the area, because a track that photons at one wavelength travels inside the teeth, as described with reference to FIG. 20A-D, is potentially different than a track of photons of a second wavelength travels inside the teeth.

Different wavelengths photons have different absorption and scattering coefficients in a specific volume or layer of the teeth. An optical path inside a tooth depends on a wavelength, and is determined by the above-mentioned properties.

Potentially, different wavelengths come out from the teeth at different locations. A distance that each optic path at each wavelength passes inside the teeth potentially enables determining and/or understanding materials and/or layer structure inside the teeth that affect different wavelengths differently.

In some embodiments, an amount of light which passed via a specific set of paths from a given light-incidence location to a light-emergence location, at a given wavelength provides the optical properties associated with a wavelength of the light. In some embodiments absorption and scattering spectra are captured, and materials composing the volume or layer of tooth through which the light passed are optionally determined. In some embodiments the material is optionally determined by comparing to known absorption and/or scattering spectra.

In some embodiments optical properties of an illuminated are optionally measured and/or calculated as described in above-mentioned article by Feng S. et al. titled "Monte Carlo simulation of photon migration path distributions in multiple scattering media" published in Proc SPIE vol. 1888, (1993).

In some embodiments the optical properties of dental enamel and/or dentin are optionally measured at wavelengths such as 450, 543, 632, 780, 850 and 1053 nm, optionally as described by Fried D. et. al. in an article titled "Nature of light scattering in dental enamel and dentin at visible and near-infrared wavelengths", published in Applied Optics, Vol. 34, Issue 7, pp. 1278-1285 (1995).

In some embodiments, different color filters are optionally used in an optical path prior to an imager's pixels, potentially providing additional information that potentially increases measurement accuracy.

In some embodiments, different color Bayer filters, are optionally used on the imager's pixels, potentially providing additional information that potentially increases measurement accuracy.

In some embodiments, geometrical changes in the projector or imager placement with regard to the teeth potentially increase measurement accuracy. By way of a non-limiting example, an angle that one imager sees the reflected pattern from the teeth is optionally different from an angle that a second, adjacent imager sees the same projector pattern reflected from the same teeth.

In some embodiments, a same imager optionally captures patterns reflecting from teeth that come from two different projectors, each projector projecting with a different angle on the teeth. In such cases a specular reflection that depends on a specific angle between a light source, a surface and a location of an imager are potentially captured when one of the projectors is active, potentially enabling differentiating between the specular reflection and non-specular reflection light. In some embodiments a projector is made active by determining that it does not produce specular reflection in an imaged captured by an imager.

In some embodiments, one projector optionally projects light or a light pattern on teeth and two or more imagers are aimed at the teeth. Images captured by the two or more imagers are optionally compared, potentially detecting if one of the images includes specular reflection. In some embodiments, an image is used, for further calculations, which does not include specular reflection.

As described above, in case of different wavelengths, a length and depth of the track that a photon passes inside the teeth potentially depends on an angle at which the photon impinges upon the tooth surface when entering the tooth. Different angles of impinging light potentially cause different tracks inside the teeth, and potentially produce different data for a same area of the teeth. The different angles potentially enable obtaining more data, potentially resulting in better measurements.

Correcting 3D Location Estimation Based on Optical Properties

In some embodiments, obtained local tooth optical properties such as $\mu_s'$, $\mu_a$, n (reduced scattering, absorption coefficients and index of refraction) are used for correcting a 3D model. For example, a 3D location may be corrected by compensating for a translucency induced patterns shift in the image. In some embodiments, on a translucent object (for example a tooth) the position of a pattern in an image (e.g. the center of a stripe in an image of a striped pattern) may be affected that is reflected and/or scattered below the tooth surface. Thus, the location of the imaged light may not correspond with the surface of the imaged object. For example when there is a non-zero angle between the illumination (e.g. projector optical axis) and the imaged photons trajectory (e.g. the camera optical axis) imaging the scattered photons of a given pattern (e.g. a stripe) from below the tooth surface, this may induce a shift in the stripe image compared to a stripe image that would have been reflected from surface reflection (e.g. white paper). For example, the direction of the local tooth surface relative to the projected light and the camera may influence the image shift. For example, the index of refraction may influence the image shift.

This induced shift may cause error in the estimated location of a surface of an IOS assuming that light is reflected from the surface of an object. The induced shift depends on said local optical properties and/or local surface angle. The correction of this error depends on accurate estimation of local optical properties. Optionally the induced shift is compensated in each location in the image. For example this may improve the depth accuracy of a resulting 3D model.

In some embodiments, a color of a pattern element may be selected and projected to be resistant to scattering. For example, a pattern may include shades of blue and/or violet that are less affected by scattering. Optionally, narrow bandwidths of light are used for example a pattern element may be limited to a light within a band of width less than 10 nm and/or between 10 to 50 nm and/or between 50 to 100 nm and/or between 100 to 500 nm. Optionally a narrow bandwidth sensor is used. For example the sensor may be able to differentiate between narrow bands of light having similar frequencies. For example, a sensor may sense three different bands within the blue/violet portion of the spectrum. For example the separation of the centers of two bands may be less than 10 nm and/or between 10 to 40 nm and/or between 40 to 100 nm and/or between 100 to 200 nm.

In some embodiments, a sensor may include narrow and wide range sensing bands. For example, a narrow band may be used to reduce to crosstalk and/or interference. Alternatively or additionally, the sensor may include a wide band. For example wide band receiver may to capture a more energy, for example when the signal is weak. For example, a hyperspectral sensor may sense in 3 narrow bands and 2 wide bands.

Shade Estimation

In some embodiments, the local optical properties are used for creating an esthetic restoration of dental elements. Relevant parameters which may be estimated include Hue (e.g. red, green, blue, etc.), Lightness (e.g. dark, light), Chroma (e.g. intense, dull), Translucency etc. The color in some cases is estimated according to CIE 1931 coordinates or Lab coordinates etc. In some embodiments, the color is estimated according to VITA Classical Shade Guide or VITA 3D Master Shade Guide. In some embodiments, the color parameters, such as shade are estimated locally, such that a 3D model or a 2D image of the scanned tooth or teeth are shown to the user with a map of the local shade in each location of the tooth.

In some embodiments, the prepared tooth or teeth is scanned before preparation to get the optical properties that will be used for prosthetic. In some embodiments, neighboring objects such as a tooth and/or teeth neighboring the prepared tooth or teeth are scanned. Optionally, a prosthetic (e.g. a crown) is generated with shading the fits the prepared tooth and/or neighboring teeth. In some embodiments, the shade estimation or stored for further use or is compared to previously stored shade estimation in order to detect changes over time of the colors that might indicate on a clinical problem or a user behavioral problem, for example bad cleaning habits, that should be fixed.

In some embodiments, the optical properties of the prepared tooth or teeth are scanned after preparation of the tooth and/or the prosthetic. Data from the scan may be used for better estimation of the final prosthetic visual look (e.g. color, shade, translucency, etc.). The effect of the neighboring teeth and/or prepared tooth on the appearance of the prosthetic may be accounted for when shading the prosthetic. The design of the prosthetic may account for the effect of a bonding layer (for example which bonds prosthetics to prepared tooth) on the light in and around the prosthetic. For example, the optical properties (e.g. $\mu_s'$, $\mu_a$, $R_\lambda$, index of refraction, florescence etc.) of the bonding material and/or the prosthetic material (e.g. Zirconia) may be considered and/or matched to achieve a desired visual look to the installed prosthetic.

In some embodiments, the effects of specular reflections from the measured area may be reduced, for example in order to achieve accurate measurement and classification of teeth shade. FIG. 24 schematically shows a typical BSDF (bidirectional scattering distribution function) diagram of a tooth to explain the problem. In some embodiments, as schematically shown for example in FIG. 25A, a light source 2503 is placed at a high enough angle from the camera (e.g. >20° or >40°), for instance on the IOS handle, so that the measurement is done away from the specular reflection angle. In some embodiments, light source 2503 is set angularly far enough from the image sensor and/or other light sources with smaller illumination angle (such as ambient light) are blocked, for instance by IOS body. In some embodiments a polarizer and/or a pair of crossed polarizers between illumination and image sensor can be used to reduce specular reflection effect. A set of specific distance, angle and location on tooth (or a partial set of them) can allow a better shade model for calibration and measurement. A reference set is defined at calibration. For instance, the VITA Classical Shade Guide.

In some embodiments, for instance IOS 2501 includes an elongate object 2502 for example, as shown in FIG. 25A. Optionally, when the shade of a tooth is needed, the user touches with elongate body 2502 the location that should be measures or slightly below that location. The elongate body 2502 may be used as a measuring device to fix the distance between IOS 2501 and/or measured tooth. The accurate measurement may, in some embodiments, facilitate a more accurate reconstruction of the tooth shade. For example, when all of the measurements are at the same difference, calibration errors may be avoided and/or the need to compensate for a different distance may be avoided.

In some embodiments, for instance as shown at FIGS. 25A-25C a mechanical standoff can similarly limit the distance between IOS and tooth during shade measurement. In some embodiments, said mechanical standoff, as shown for example, in FIGS. 25B-25C, may set the tooth angle relative to IOS. For example, an apparatus physical size and/or structure may be designed so that a correct measurement is done when the apparatus is connected to the device and/or is flush with the measured tooth. In some embodiments, verification that the standoff is attached to the measured tooth can be done by getting the measured tooth at a small distance (e.g. <50 um) from said standoff distal end. In some embodiments, when the distance is correct shade measurement may automatically be taken.

In some embodiments the standoff apparatus can be a permanent part of the device or an adaptor which can be connected to IOS. In some embodiments the distance can be mechanically set by using the probe 2502 of known length, for example as shown in FIG. 25A. Optionally the probe 2502 is attached to the device body 2501 and or can be used as a measure of the correct distance. For example, a measurement may be taken when the probe 2502 is touching the measured tooth.

In some embodiments, the apparatus includes an open frame 2505 shown for example in FIG. 25B attached to the device. For example attachment may be by a non-obstructing handle 2504. The handle's length optionally sets the correct distance and/or the frame's attachment angle sets the correct angle. For example, the angle and/or distance may be set when the frame is flushed with the tooth. Alternatively or additionally, the frame can be used as a guide to the user to mark the measurement location on the tooth. Alternatively or additionally, a sleeve 2506 can be added to the frame, as shown for example in FIG. 25C to block ambient light and control the illumination of the measured section.

In some embodiments, when the shade of a tooth is measured, (e.g. IOS move to shade measurement mode) the IOS provides an indication to the user when achieving the desired distance and/or angle and/or position over the tooth. For example the 3D teeth data may be used to determine the desired position and/or to indicate to the user when the desired position has been reached.

In some embodiments, the probe 2502 of FIG. 25A or 2506 of FIG. 2C is optionally hollow, enabling measurement of light through the probe. This potentially reduces effects of potential ambient light and potentially directs the measurement to a specific area of interest on the tooth.

In some embodiments the standoff distance is fixed for example as shown at FIGS. 25A-C. Optionally, the IOS provides an indication to the user when the desired angle for shade measurement has been achieved, for example, when the user touches a standoff to a tooth. For example, in the shade measurement mode fixing the position may remove the need for compensating the angle effect of the shade measurement.

In some embodiments the IOS provides an indication to the user when a desired location on the tooth is being measured. For example, the tooth center, for shade measurement when the user touches with a standoff a tooth in shade measurement mode in the desired location (e.g. tooth center). This may help measure a desired position on an object with shade variations.

In some embodiments the user scans the tooth for mapping shade. For example, scanning may be performed while touching the scanned tooth with a standoff. The IOS optionally builds a 3D map of tooth with accurate shade at each location.

Reference is now made to FIG. 25D, which is a schematic illustration of a 3D intra-oral scanner system, according to some embodiments of the disclosure.

In some embodiments, the probe 2502 of FIG. 25A or 2506 of FIG. 2C is optionally hollow, enabling measurement of light through the probe. This potentially reduces effects of potential ambient light and potentially directs the measurement to a specific area of interest on the tooth. FIG. 25D shows a non-limiting example embodiment of a hollow probe 2509 in context of an IOS system 200 as described above with reference to FIG. 2.

The example embodiment includes an IOS 202, shaped and/or sized for insertion into the mouth for scanning an intra-oral scene 217. In some embodiments, the IOS 202 includes a hand piece 204 and a head portion 208. In some embodiments, an oral-facing surface 210 of the head portion 208 includes a light emitter, pattern projector 216, and an optical aperture of a camera or imager 260. In some embodiments the hollow probe 2509 encloses the light path between the light emitter, pattern projector 216, the intra-oral scene 217 (a tooth in the non-limiting example of FIG. 25D), and the camera or imager 260, so that incident light is prevented from affecting measurements.

In some embodiments, the pattern projector 216 and/or a different light projector is configured for projecting a pattern 219 onto the chosen surface, for example onto a surface of tooth 220. In some embodiments, pattern 219 comprises an arrangement of recurrent parallel stripes 221. In some embodiments, each stripe 221 is composed of a different wavelength or wavelength range. In some embodiments, the IOS comprises one or more folding mirrors positioned to redefine the baseline by forming virtual aperture locations.

In some embodiments, imager 260 comprises one or more filters for selectively detecting the different wavelengths of pattern 219. Optionally, the filters are narrowband filters. In some embodiments, the probe is optionally positioned touching a tooth, or positioned very close to the tooth, such that light from the projector optionally does not reach the teeth. The light that goes into the hollow probe 2509 and towards the camera is light coming out of the teeth after passing through the teeth, as described with reference to FIGS. 20A-D. In such embodiments light noise coming from ambient room light and/or reflections of light inside the mouth is potentially reduced.

In some embodiments, a uniform light source is used to illuminate through the hollow probe 2509, so that the camera sees reflected light from the teeth without interference from ambient room light and/or reflections from the mouth. Such embodiments potentially provide more accurate shade measurement. In some embodiments, the uniform light is reflected from multiple areas within a field of view provided by the hollow probe 2509, yet a resulting image potentially includes less specular reflections that would damage light measurement, by virtue of being protected from reflections of light originating from outside the hollow probe 2509.

FIG. 26 illustrates a process of measuring a shade in accordance with an embodiment of the current disclosure. In some embodiments some or all of the process is applied, 1. Color images are taken of teeth/reference 2601. In different embodiments the color images will be taken either using a wide band illumination (e.g. white LED), a colored patterned projector or a spectral or hyperspectral source.
   a. Optionally color data shall be collected at the reference distance. Optionally, or additionally, color data shall be collected at a range of reference distances. The range of reference distances is optionally described either by a minimum and maximum allowed distance, or by a nominal distance and a tolerance above and below the nominal distance. An indication is optionally given to a user that the IOS is within an acceptable distance to collect color data, i.e. by an audio signal.
   b. Optionally color data shall be collected only at a predetermined reference angle. Optionally, or additionally, color data shall be collected at a range of reference angles. The range of reference angles is optionally described either by a minimum and maximum allowed angle, or by a nominal angle and a tolerance above and below the nominal angle. An indication is optionally given to a user that the IOS is within an acceptable angle to collect color data, i.e. by an audio signal.
   c. Optionally the effect of ambient light will be removed and/or the image color the data is processed is used to calibrate the device.
2. The color data is optionally separated spatially according to its location on the tooth 2602. For example, a color measured at the blade of the tooth may be classified separately from a color measured at the base of the tooth.
3. In some embodiments the color data is processed 2603. For example—noise may be reduced, average data calculated and/or color distribution may be used. In some embodiments RBG color convention may be used. Alternatively or additionally, other color conventions may be used, for example HSV, YCbCr, or others.
4. Calibration:
   a. The collected and processed data of known shade (for example VITA classical shade guide or from teeth classified by several professionals) is optionally collected from several measurements. If distance or angle or illumination is not set, these measurements may be corrected to reflect the possible different scenarios.
   b. A model is optionally built 2607 based on the data. For example the model may use the collected and processed data and/or the known shade 2606 to characterize different shades, based on their color data.
   c. The model parameters and results are optionally stored 2608.
5. Classification:
   a. Data collected from measurements is optionally processed using stored model parameters. For example, processing may consider on color data, location on tooth and other relevant information.
   b. Optionally model used to determine 2604 shade and/or results are presented 2605. In one embodiment a single result is presented. In other embodiment a few closest matches are identified and presented.
   c. Data is optionally displayed either by prompting from user on a specific location on the tooth or collected and added to a 3D model as a shade map.

Projector

Projector Configurations

In some embodiments, a projector of a wavelength coded pattern comprises a plurality of light sources. For example, each light source may be configured to illuminate a scene and/or a portion thereof with a waveband of the pattern. Optionally, there may be a gap between light sources. The gap may not emit light to produce a black referential area in the projected pattern. Optionally, by focusing illumination on illuminated areas of the pattern and/or illuminating each area with a light source tuned to the color of illumination in that area, an illumination source may be made more efficient. For example, the source may create a referential color pattern by illuminating the whole area and then blocking the illumination in the black referential areas.

Optionally, for example as shown in FIG. 6C, a set of interference filters 606 attached to a transparent substance 608 are illuminated by light source 602. For example, light source 602 may emit a wide spectrum light. In some embodiments, the filters are not adjacent. Optionally there are light absorbing areas in between. For example, the light absorbing areas may produce black referential areas in the projected pattern. In some embodiments, the light absorbing areas in between filters are produced by adding a transparent blocking mask (e.g. chrome coated glass) on top of the filter substrate and/or by attaching an adjacent mask to a lower resolution color filter pattern. An optional advantage of such embodiments that high resolution chrome masks (e.g. <1 um resolution) can be produced at relative low cost and can provide the needed resolution while the color filters, which are more difficult to produce with high resolution, can have a lower resolution. Optionally, the combination will have high resolution and achieve spectral specificity at a relatively low cost.

Figure 6G:
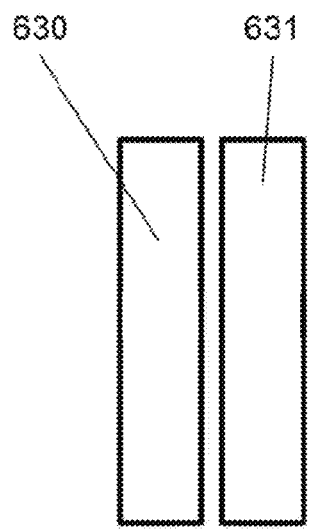

In some embodiments, for example as shown in FIG. 6G a large area light source 630 is used in conjunction with one or more fluorescent (e.g. phosphor) materials 631 that changes the light source wavelength to another wavelength, for example as the phosphors used in LEDs.

Figure 6H:
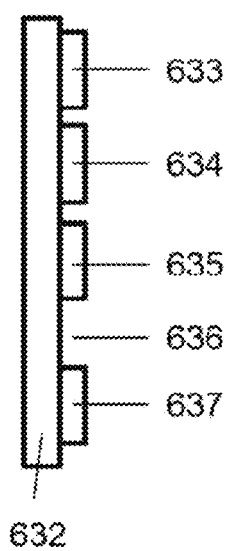

In some embodiments, for example as illustrated in FIG. 6H, a large area light source 632 is used with transparent, opaque and/or fluorescent phosphors are used to produce regions with the color of the light source, dark areas and/or other colored areas. For example a blue LED 632 may be used with transparent stripes 636 (e.g. to produce a blue pattern object) and/or green 634 and/or red 633 phosphors (to produce other colored pattern objects) and/or opaque regions 636 (to produce dark pattern objects).

In some embodiments, instead of the LED phosphors the wavelength change is done by nano particles or quantum dots (for example as used in displays). Optionally nano particles or quantum dots are used to produce narrower spectral bands illumination and/or reduced crosstalk.

Transparent/blocking masks (e.g. chrome coated glass) as described above may be used with any of the above projector technologies. For example masks may produce high resolution dark pattern objects without requiring configuring dark areas in the projector itself.

In some embodiments, for example as described above some of the light is blocked to create a referential pattern illumination.

In some embodiments, a novel light source produces a colored referential pattern much more efficiently. The improvement of referential pattern projector efficiency may facilitate miniaturization of an IOS and/or a pattern projector. Optionally, the miniaturized IOS will facilitate high speed scanning (e.g. 100-5000 frames per second), large working distance (e.g. 30-50 mm) and/or large depth of field (e.g. 5-50 mm). To achieve some or all of these, the device may include a high F/# (e.g. 4-6). For example, the device may include a high intensity illumination source which takes up a small volume. In some embodiments, this may create also heat dissipation challenge. In some embodiments, improving the projector efficiency may reduce the heat dissipation problem.

Figure 6I:
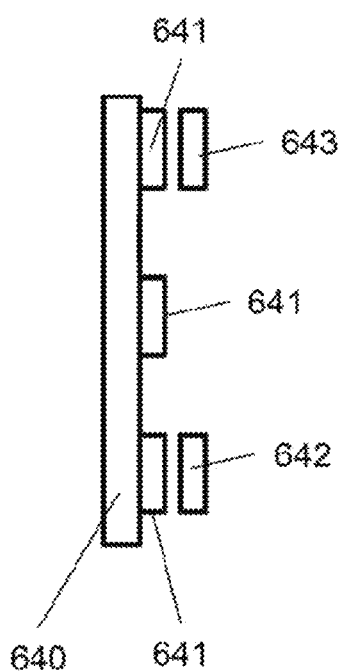

In some embodiments, for example, as shown in FIG. 6I, the plurality of LEDs 641 are not adjacent, but optionally have a gap between them, which does not emit light and produce the black referential areas in the projected pattern. Optionally, LEDs used for display technologies such as AMOLEDs are used. In some embodiments, said LEDs are independently operable and arranged in a dense matrix, such that by turning off some of the LEDs said non-emitting areas are dynamically created. Optionally, AMOLEDs formed as thin elongated blocks are used.

Figure 6J:
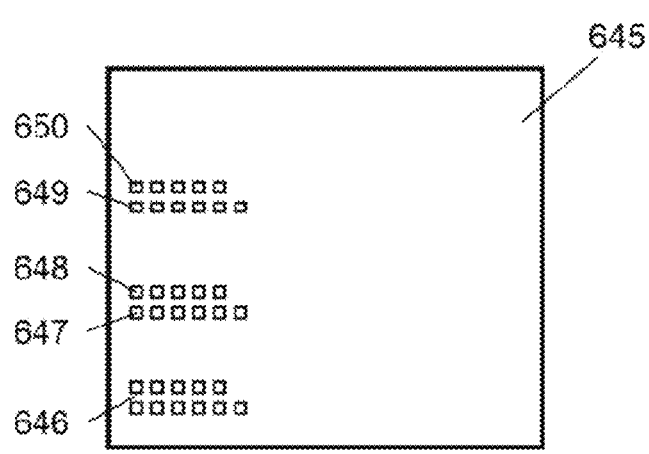

In some embodiments micro LEDs are placed on the illuminated area of a substrate and/or to black referential areas are left without the LEDs to form the pattern with high efficiency. For example, in FIG. 6J a portion of a two dimensional substrate 645 is shown schematically. For example, a 2×2 mm substrate is covered by 30 stripes of 20 um width by 2 mm length with 40 um width gap in between. Each line is optionally composed of a mixture of micro LEDs of different colors. For example, bottom line is a green stripe made of 2 rows of 10×10 um green micro LEDs 646. Next row is a yellow stripe made by mixing red micro LEDs 647 with green micro LEDs 648 in interleaved order. Next row is a magenta stripe made by mixing red micro LEDs 649 with blue micro LEDs 650 in interleaved order. In some embodiments, the red micro LEDs 647 and the green micro LEDs 648 are not placed in different rows but in different columns or in another spatial arrangement inside the line. In some embodiments uneven number of blue and red micro LEDs is used to create a line with different hue.

In some embodiments a full color micro LEDs display is used for illuminating the pattern. For example, only the LED located on the illuminated portion of the pattern is illuminated and/or the rest of the LEDs are turned off. For instance, a 2×2 mm micro LED display may have 10 um RGB LEDs displaying 30 stripes of 20 um width by 2 mm length (2×2000LEDs). Optionally in between illuminated LED's there may be a gap (for example of 40 um width) of turned off LEDS. Each line is optionally composed of a mixture of micro LEDs of different colors. LED arrangement over micro LED display can be standard such as RGGB, or customized such as RGBW.

In some embodiments, some of the micro LEDs in the array transmit light in the NIR range for example at a wavelength of 850 nm or 1300 nm or 1550 nm or other NIR wavelength. For example, in RGGB, a green stripe made of 2 rows of interlaced 10×10 um green micro LEDs. A yellow stripe made, for example, by mixing red micro LEDs with green micro LEDs in interleaved order. A magenta stripe made, for example, by mixing red micro LEDs with blue micro LEDs in interleaved order. A white stripe made, for example, by turning on all 2×2000 LEDs of the 2 rows.

In some embodiments wavelength conversion is combined with monochrome LEDs strips or micro LEDs to get the colored areas efficiently. For example, FIG. 6I, said blue LED can be formed as blue LED stripes 641 placed on a substrate 640. Optionally gaps in between the LEDs produce black referential areas, by not illuminating the referential areas. Some of the stripes can be covered with wavelength conversion masks (e.g. Quantum Dots, phosphor etc.) for instance, to convert blue to green 642, or to red 643 or kept clear to produce blue. Additional colors can be produced such as green, red, magenta, yellow, cyan, white, etc.

In some embodiments, similar stripes patterned light source can be obtained with VCSELS. For instance, some or all of light sources 646, 647, 648, and/or 649 of FIG. 6J may include VCELs and/or the substrate 645 may include a VCSELs chip. For example blue VCSEL emitters may be arranged in lines or strips in similar dimensions. For instance multi emitter VCSEL source can be arranged in rows of adjacent 10 um VCSEL emitters with a distance of 50 um between them. In some embodiments some of the emitters may be covered by wavelength conversion materials (e.g. QD, phosphor etc.) to convert the blue wavelength to other colors (e.g. green, red, magenta, yellow, cyan, white). In some embodiments the blue VCSELs stripes are converted to white (e.g. using white phosphor) and/or covered by an additional filters layer, for example as described before.

In some embodiments, a hyper spectral detector is used in conjunction with a one or narrower waveband projectors. The detector optionally measures the optical properties for each projector wavelength band. From the differing properties and positions of the images of the different wavelength bands, the wavelength dependency of the optical properties can be derived.

Figure 6K:
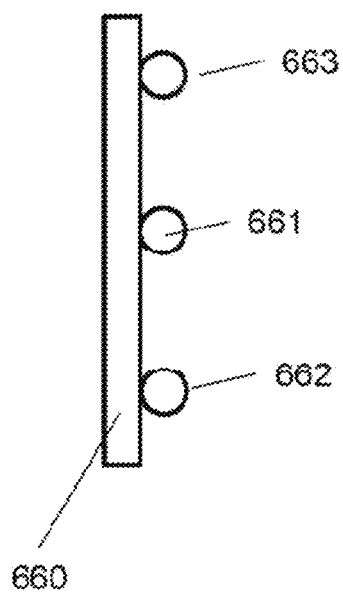
Figure 6M:
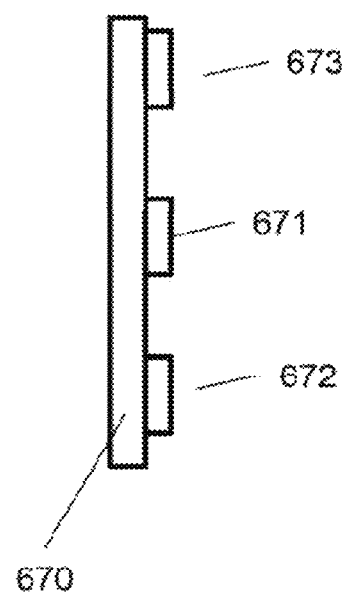

In some embodiments, patterned light source are obtained using fibers. For example fibers are arranged in stripes where the end of the fiber is pointing forward. For example, fibers may be used in place of micro LEDs in FIG. 6J. For example some fibers 650 may be lit by a green lights source for example green LED or Laser Diode. In some embodiments, the fibers of a given color can be bundled together at the light source side in a shape that increases light collection (e.g. according to the light source shape, for instance, circular or rectangular bundle for a circular or rectangular LED). In some embodiments, light comes out from the side of a fiber using an edge emitting fiber, as shown by fibers 661-663, each in a different color as shown for example in the cut of light source 660 in FIG. 6K and/or light source 655 of FIG. 6O. In some embodiments, similar pattern light source can be obtained with light pipes instead of fibers, as shown for example in FIG. 6M, wherein side illuminated light pipes 671-673 at disposed over glass substrate 670. The light pipes are optionally side illuminated directly by a light source, such as LED and/or laser diode and/or through fibers with different colors. In some embodiments, similar patterned light source can be obtained with optical waveguides for example polymer on glass or silicon on insulator (SOI) waveguides. In some embodiments, similar patterned light source may include semitransparent mirrors 660 that reflect one wavelength that is hitting them from one side and/or transfer another wavelength that is hitting them from another side as seen for example in FIG. 6P Optionally a mirror is covered with a monochrome mask 661 (e.g. chrome on glass) placed in a way that each mirror is illuminated with different wavelength, for example Blue Red and Green. The mirrors are optionally placed one behind the other so that the final result is a colored pattern for example including stripes. In some embodiments, instead of the monochromatic mask that just obscure the light and convert it to heat, strips of mirrors 665 are placed in a way so that all the light from the source for example is hitting a semitransparent mirror but dark areas are formed in the spaces between the mirrors for example as illustrated in FIG. 6Q. This may be more efficient than using a mask to absorb light in dark areas and turn it to heat. This method is optionally done for the relevant wavelengths, for example, Red Green and Blue, to create a color pattern for example as described above in FIG. 6P.

Figure 6N:
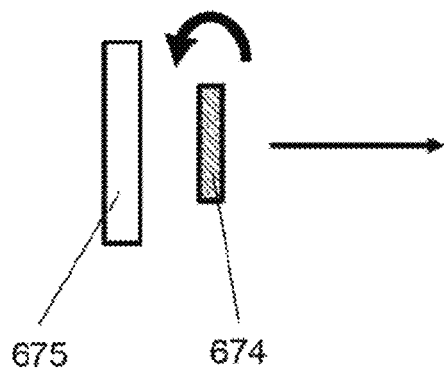

In some embodiments, as shown in FIG. 6N, a variable wavelength source 675 is used. For example, a tunable laser is used with a 1D scanning mirror 674 (such as a MEMS mirror).

In some embodiments, an optical element focuses the light source light as a strip over the tooth scanned by mirror. Additionally, or alternatively, other optical components suitable for directing or re-directing light are used. To get the high efficiency, at the black referential areas, said light source is not emitting light.

In some embodiments, at least one source is used. For instance, 3 red green blue LEDs may be used. To get the high efficiency, at the black referential areas, a light source is not emitting light. At the lines areas any combination of the 3 is illuminating the tooth to get the required color. If the disparity between the LEDs is perpendicular to the scanning axis, such the LEDs illumination is delayed according to the mirror rotation speed, such that they illuminate the same strip or FOV over the target at the same time.

Projectors Optics

In some embodiments a colored lines pattern is projected onto a measured object, such as a tooth, gums and other intraoral feature. For example a projector may include a projection lens. In some embodiments the aperture of the projection lens is non circular (e.g. elliptical aperture). For example, the aperture may have a larger size parallel to the direction of lines in the pattern and/or a smaller size in a direction that is perpendicular to the lines pattern. Optionally, the line pattern may have a lower DOF (depth of filed) over the direction of the lines and/or a higher DOF in the direction that is perpendicular to the lines. In some embodiments, increasing the DOF perpendicular to the lines may improve contrast between lines. Alternatively or additionally, the projection lens may provide higher illumination than a regular circular aperture lens with the same DOF performance. A similar concept can be applied to other patterns that include non-isotropic patterns, for example, when the spatial frequency of the information on one (e.g. x axis) direction significantly differs from the other direction (e.g. y axis). Optionally the direction with the lower frequency can be more smeared over focus variations of different distances and can have a larger aperture dimension.

Reference is now made to FIG. 27, which is a simplified illustration of a light projector which includes a non-circular aperture according to an example embodiment of the invention.

FIG. 27 shows a stripes projector with a non-limiting example of an elliptical aperture in an exploded view.

FIG. 27 shows a light source 2701, for shining light through a transparency 2702 pattern, optionally a colored stripes pattern with dark stripes between colored stripes. In some embodiments the light source 2701 and/or the transparency 2702 can be replaced by any other of the light source configurations suggested by the instant document and/or by PCT application number PCT/IL2017/051150.

FIG. 27 shows the transparency 2702 projected via a simplified schematic illustration of an optical system that includes two optical elements or sets of optical elements, schematically shown as optical elements 2703 and 2705, and showing an optical aperture 2704 between the optical elements 2703 and 2705.

In imaging systems an aperture is sometimes called also an aperture stop or a stop. The aperture typically affects an optic rays cone angle and/or brightness at an image point. The optic rays cone angle typically determines the Depth Of Field (DOF). A narrower cone corresponds to a higher F-number (F#), and a larger DOF.

In some embodiments, the aperture 2704 is optionally implemented as a ring, as some other mechanical shape, or as a special element such as a diaphragm, optionally with an elliptic hole or as a reflecting, e.g. chrome-coated, glass with a transparent shape (such as an ellipse) placed in the optical path.

In case of a non-circular aperture, the optic rays cone will potentially take on a shape of the non-circular aperture. For example, an elliptical aperture with aspect ratio of 5 between the short and long axes of the ellipse will produce an optic rays cone with a cross section having a similar aspect ratio.

In the case schematically shown in FIG. 27 the transparency 2702 includes a colored stripes pattern aligned parallel to a long axis of the elliptic aperture 2704. In this example, the projected pattern is aligned to have lower spatial frequencies at a direction of a long axis of the elliptic aperture 2704. Therefore, if the pattern image is smeared along a direction of the lines, the smearing effect on the resulting image contrast will be negligible, while if pattern image is smeared perpendicular to the direction of the lines, the resulting image contrast will be decreased.

In the example shown by FIG. 27, the dimensions of the elliptic aperture 2704 are optionally optimized to provide a different effective F-number along the major axis of the elliptic aperture 2704, to control Depth-Of-Field (DOF) and/or power loss of the projected pattern. The short axis of the elliptic aperture 2704 provides a higher effective F number, a lower angle of the optic rays cone, and a higher DOF, so a potential smear of the projected pattern along the direction of the short axis will be smaller, in case of object distance variations. The minor axis has a smaller length, so it potentially transmits less light.

The major axis of the elliptic aperture 2704 provides a lower effective F number, a potentially larger angle of the optic rays cone, and a lower DOF, therefore a potential smear of the projected pattern along the direction of the long axis may be larger upon potential object distance variations. Since the major axis is the same direction of the stripes, the smear effect on the image contrast is reduced. Because of its larger length, the major axis potentially transmits more light and potentially improves an overall optical system efficiency.

In some embodiments the effective F number along the major (longer) axis of the non-circular aperture is optionally between 2.5 and 6 and the effective F number along the minor (shorter) axis of the non-circular aperture is optionally between 0.5 and 2.5.

In some embodiments the effective F number along the major (longer) axis of the non-circular aperture is 5 and the effective F number along the minor (shorter) axis of the non-circular aperture is 1, so an aspect ratio of the non-circular aperture is 5, and the non-circular aperture transmits 5 times more light comparable to a projector with a similar DOF performance. In some embodiments smaller or higher effective F number are optionally used.

In some embodiments the non-circular aperture shape may be oval or rectangular or rectangular with rounded corners, etc.

In some embodiments, a hyper spectral detector is used in conjunction with one or more narrow waveband projectors. The detector optionally measures the optical properties for each projector wavelength band. From the differing properties and positions of the images of the different wavelength bands, the wavelength dependency of the optical properties can be derived.

In some embodiments, where the hyper spectral CMOS can detect each wavelength by itself and when we have specific wavelengths in our light sources, for example, VCSELs, micro LEDs or QD, we can create a different wavelength by arranging the light sources in a way that two or more wavelengths will be transmitted from a close place, for example as seen in FIG. 6A, and also create a smear in the optical elements of the projection lens, projecting the light from the light sources to the tooth such that on the tooth the wavelength that will fall on the tooth is different than the light sources. In some embodiments, the smear in the optical elements is done only in the direction of the line so the lines focus on the teeth is not or less effected by the optical smear The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this disclosure may be presented in a range format. It should be understood that the description in range format is merely for convenience and brevity and should not be construed as an inflexible limitation on the scope of the various embodiments of the inventions disclosed herein. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the various inventions disclosed herein, which are, for clarity, described in the context of separate embodiments, may also be provided in combination in a single embodiment. Conversely, various features of the various inventions disclosed herein, which are, for brevity, described in the context of a single embodiment, may also be provided separately or in any suitable subcombination or as suitable in any other described embodiment. Certain features described in the context of various embodiments are not to be considered essential features of those embodiments, unless the embodiment is inoperative without those elements.

Although inventions disclosed herein have been described in conjunction with particular embodiments thereof, it is evident that many alternatives, modifications and variations will be apparent to those skilled in the art. Accordingly, it is intended to embrace all such alternatives, modifications and variations that fall within the spirit and broad scope of claims supported by the present disclosure.

Embodiments of the various embodiments disclosed herein may also be patentable over the prior art by specifically lacking one and/or another structure, step, and/or functionality; in other words, claims directed to such embodiments can include negative limitations to distinguish them from the prior art.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the inventions disclosed herein. To the extent that section headings are used, they should not be construed as necessarily limiting.

In addition, any priority document(s) of this application is/are hereby incorporated herein by reference in its/their entirety.

What is claimed is:

1. A structured light based 3D measurement system comprising:
   at least one imager,
   at least one pattern projector; and
   a processing unit to determine 3D information from image information obtained by said imager of a pattern projected on scene by said pattern projector, wherein said pattern projector comprises a non-circular aperture stop having a longer axis and a shorter axis;
   which pattern projected on said scene is aligned to have lower spatial frequencies along a direction of the longer axis of said non-circular aperture stop.

2. The system of claim 1, wherein said projected pattern comprises a colored stripes pattern, and the direction along the stripes is aligned along the longer axis of said non-circular aperture stop.

3. The system of claim 1, wherein dimensions of said non-circular aperture stop are configured for providing a different effective F number along different respective main axes of said non-circular aperture stop to differentially control Depth-Of-Field (DOF) and power loss along corresponding axes of said projected pattern.

4. The system of claim 3, wherein the main axes of the non-circular aperture stop comprise a major axis and a minor axis, and said effective F number along the major axis of said non-circular aperture stop is between 2.5 and 6 and said effective F number along the minor axis of said non-circular aperture stop is between 0.5 and 2.5.

5. The system of claim 1, wherein the non-circular aperture stop comprises an oval shape, or a rounded corner, or a rectangle with rounded corners shape, or an ellipse shape.

6. The system of claim 1, wherein the pattern projector comprises a transparency including colored stripes, the non-circular aperture stop has a longer axis and a shorter axis, and the colored stripes are aligned parallel to a long axis of the non-circular aperture stop.

7. The system of claim 6, wherein the pattern projector comprises a light source oriented to shine light through the transparency and then through the non-circular aperture stop.

8. The system of claim 7, wherein the transparency and the non-circular aperture stop are separated by optical elements through which the light source also shines light.

9. The system of claim 2, wherein individual stripes of the colored stripes pattern are separated from one another by dark stripes.

10. The system of claim 3, wherein DOF is relatively increased in the projected pattern along a direction parallel to a shorter of the main axes of the non-circular aperture stop, compared to a direction parallel to the major axis, along which power loss is correspondingly relatively decreased.

11. The system of claim 2, wherein wavelengths of the colored stripes comprise wavelengths from between 400-500 nm.

12. The system of claim 2, wherein the colored stripes comprise different wavelengths selected by a plurality of different respective narrowband filters.

13. The system of claim 12, wherein the narrowband filters have pass bands of 10 nm or less.

14. The system of claim 12, wherein the imager comprises a hyperspectral imager configured to differentiate between said different wavelengths selected by said plurality of different respective narrowband filters.

15. A structured light based 3D measurement system comprising:
  at least one imager,
  at least one pattern projector; and
  a processing unit to determine 3D information from image information obtained by said imager of a pattern projected on scene by said pattern projector, wherein said pattern projector comprises a non-circular aperture stop;
  wherein dimensions of said non-circular aperture stop are configured for providing a different effective F number along different respective main axes of said non-circular aperture stop to differentially control Depth-Of-Field (DOF) and power loss along corresponding axes of said projected pattern.

16. The system of claim 15, wherein said projected pattern comprises a colored stripes pattern, and the direction along the stripes is aligned along the longer axis of said non-circular aperture stop.

17. The system of claim 15, wherein the main axes of the non-circular aperture stop comprise a major axis and a minor axis, and said effective F number along the major axis of said non-circular aperture stop is between 2.5 and 6 and said effective F number along the minor axis of said non-circular aperture stop is between 0.5 and 2.5.

18. The system of claim 15, wherein the non-circular aperture stop comprises an oval shape, or a rounded corner, or a rectangle with rounded corners shape, or an ellipse shape.

19. The system of claim 15, wherein the pattern projector comprises a transparency including colored stripes, the non-circular aperture stop has a longer axis and a shorter axis, and the colored stripes are aligned parallel to a long axis of the non-circular aperture stop.

20. The system of claim 19, wherein the pattern projector comprises a light source oriented to shine light through the transparency and then through the non-circular aperture stop.

21. The system of claim 20, wherein the transparency and the non-circular aperture stop are separated by optical elements through which the light source also shines light.

22. The system of claim 16, wherein individual stripes of the colored stripes pattern are separated from one another by dark stripes.

23. The system of claim 15, wherein DOF is relatively increased in the projected pattern along a direction parallel to a shorter of the main axes of the non-circular aperture stop, compared to a direction parallel to the major axis, along which power loss is correspondingly relatively decreased.

24. The system of claim 16, wherein wavelengths of the colored stripes comprise wavelengths from between 400-500 nm.

25. The system of claim 16, wherein the colored stripes comprise different wavelengths selected by a plurality of different respective narrowband filters.

26. The system of claim 25, wherein the narrowband filters have pass bands of 10 nm or less.

27. The system of claim 25, wherein the imager comprises a hyperspectral imager configured to between said different wavelengths selected by said plurality of different respective narrowband filters.

28. A structured light based 3D measurement system comprising:
  at least one imager,
  at least one pattern projector; and
  a processing unit to determine 3D information from image information obtained by said imager of a pattern projected on scene by said pattern projector, wherein said pattern projector comprises: a non-circular aperture stop, a transparency including colored stripes, the non-circular aperture stop having a longer axis and a shorter axis, where the colored stripes are aligned parallel to a long axis of the non-circular aperture stop.

29. The system of claim 28, wherein said projected pattern comprises a colored stripes pattern, and the direction along the stripes is aligned along the longer axis of said non-circular aperture stop.

30. The system of claim 28, wherein the non-circular aperture stop comprises an oval shape, or a rounded corner, or a rectangle with rounded corners shape, or an ellipse shape.

31. The system of claim 28, wherein the pattern projector comprises a light source oriented to shine light through the transparency and then through the non-circular aperture stop.

32. The system of claim 31, wherein the transparency and the non-circular aperture stop are separated by optical elements through which the light source also shines light.

33. The system of claim 29, wherein individual stripes of the colored stripes pattern are separated from one another by dark stripes.

34. The system of claim 28, wherein wavelengths of the colored stripes comprise wavelengths from between 400-500 nm.

35. The system of claim 29, wherein the colored stripes comprise different wavelengths selected by a plurality of different respective narrowband filters.

36. The system of claim 35, wherein the narrowband filters have pass bands of 10 nm or less.

37. The system of claim 35, wherein the imager comprises a hyperspectral imager configured to differentiate between said different wavelengths selected by said plurality of different respective narrowband filters.

* * * * *